(12) United States Patent
Shanley et al.

(10) Patent No.: US 12,329,953 B2
(45) Date of Patent: Jun. 17, 2025

(54) SYSTEM AND METHOD FOR MULTIPLE SITE INJECTION

(71) Applicant: CREDENCE MEDSYSTEMS, INC., Menlo Park, CA (US)

(72) Inventors: Conor Edward Shanley, Emerald Hills, CA (US); Alan E. Shluzas, San Carlos, CA (US); Mina M. Leung, Mountain View, CA (US); Stephen H. Diaz, Palo Alto, CA (US)

(73) Assignee: Credence MedSystems, Inc., Menlo Park, CA (US)

( * ) Notice: Subject to any disclaimer, the term of this patent is extended or adjusted under 35 U.S.C. 154(b) by 829 days.

(21) Appl. No.: 17/574,279

(22) Filed: Jan. 12, 2022

(65) Prior Publication Data

US 2022/0134021 A1 May 5, 2022

Related U.S. Application Data

(63) Continuation of application No. 16/683,157, filed on Nov. 13, 2019, now Pat. No. 11,759,577.
(Continued)

(51) Int. Cl.
*A61M 5/00* (2006.01)
*A61M 5/31* (2006.01)
(Continued)

(52) U.S. Cl.
CPC ........ *A61M 5/3221* (2013.01); *A61M 5/3146* (2013.01); *A61M 5/3148* (2013.01);
(Continued)

(58) Field of Classification Search
CPC ...... A61M 2005/3139; A61M 5/31595; A61M 5/31555; A61M 5/3158; A61M 5/322;
(Continued)

(56) References Cited

U.S. PATENT DOCUMENTS

| 827,693 A | 7/1906 | Korb |
|---|---|---|
| 2,648,334 A | 8/1953 | Brown et al. |

(Continued)

FOREIGN PATENT DOCUMENTS

| EP | 0074842 | 3/1983 |
|---|---|---|
| EP | 0904792 | 3/1999 |

(Continued)

OTHER PUBLICATIONS

Non-Final Office Action for U.S. Appln. No. 16/683,157 dated Jan. 10, 2022.
(Continued)

*Primary Examiner* — William R Carpenter
(74) *Attorney, Agent, or Firm* — Vista IP Law Group LLP

(57) ABSTRACT

A system for injecting includes a syringe body having proximal and distal ends, a syringe interior, and a syringe flange at the proximal end thereof. The system also includes an injectable fluid disposed in the syringe interior. The system further includes a finger flange coupled to the syringe flange. Moreover, the system includes a stopper member disposed in the syringe interior. In addition, the system includes a plunger ratchet member coupled to the stopper member. The system also includes a plunger tube disposed coaxially around at least a portion of the plunger ratchet member and operatively coupled thereto.

15 Claims, 55 Drawing Sheets

Related U.S. Application Data

(60) Provisional application No. 62/760,273, filed on Nov. 13, 2018.

(51) Int. Cl.
    *A61M 5/315*      (2006.01)
    *A61M 5/32*      (2006.01)
    *A61M 5/34*      (2006.01)

(52) U.S. Cl.
    CPC ...... *A61M 5/31526* (2013.01); *A61M 5/3158* (2013.01); *A61M 5/31581* (2013.01); *A61M 5/31595* (2013.01); *A61M 5/347* (2013.01); *A61M 2005/3128* (2013.01); *A61M 2005/3132* (2013.01); *A61M 2005/3152* (2013.01); *A61M 2005/3201* (2013.01); *A61M 2005/3231* (2013.01); *A61M 2005/3241* (2013.01)

(58) Field of Classification Search
    CPC ........ A61M 5/3234; A61M 2005/3239; A61M 2005/3242
    See application file for complete search history.

(56) References Cited

U.S. PATENT DOCUMENTS

| | | | |
|---|---|---|---|
| 2,771,217 | A | 11/1956 | Brown et al. |
| 2,933,087 | A | 4/1960 | Hamilton |
| 3,153,496 | A | 10/1964 | Johnson |
| 3,216,616 | A | 11/1965 | Blankenship, Jr. |
| 3,770,026 | A | 11/1973 | Isenberg |
| 3,815,785 | A * | 6/1974 | Gilmont ............ A61M 3/00 D24/114 |
| 3,921,864 | A | 11/1975 | Dawes |
| 3,923,207 | A | 12/1975 | Kyogoku |
| 4,073,321 | A | 2/1978 | Moskowitz |
| 4,194,505 | A | 3/1980 | Schmitz |
| 4,370,982 | A | 2/1983 | Reilly |
| 4,384,581 | A | 5/1983 | Conway |
| 4,563,178 | A | 1/1986 | Santeramo |
| 4,955,870 | A * | 9/1990 | Ridderheim ....... A61M 5/3234 604/198 |
| 4,973,318 | A * | 11/1990 | Holm ............... A61M 5/24 604/218 |
| 5,304,152 | A | 4/1994 | Sams |
| 5,407,436 | A * | 4/1995 | Toft ............... A61M 5/3234 604/110 |
| 5,667,495 | A | 9/1997 | Bitdinger et al. |
| 5,743,889 | A | 4/1998 | Sams |
| 5,833,669 | A | 11/1998 | Wyrick |
| 5,961,495 | A | 10/1999 | Walters et al. |
| 6,126,644 | A | 10/2000 | Naganuma et al. |
| 6,419,656 | B1 | 7/2002 | Vetter et al. |
| 7,329,241 | B2 | 2/2008 | Horvath et al. |
| 7,678,084 | B2 | 3/2010 | Judson et al. |
| 8,361,036 | B2 | 1/2013 | Moller et al. |
| 8,529,521 | B2 | 9/2013 | Erickson et al. |
| 8,920,384 | B2 * | 12/2014 | Cronenberg ...... A61M 5/31541 604/209 |
| 9,220,631 | B2 | 12/2015 | Sigg et al. |
| 9,345,842 | B2 | 5/2016 | Chanoch et al. |
| 9,566,387 | B2 | 2/2017 | Verhoeven et al. |
| 9,707,354 | B2 | 7/2017 | Madsen et al. |
| 2006/0129108 | A1 | 6/2006 | Vetter et al. |
| 2006/0200077 | A1 | 9/2006 | Righi et al. |
| 2008/0262435 | A1 | 10/2008 | Erickson et al. |
| 2010/0175779 | A1 | 7/2010 | Ogawa et al. |
| 2011/0046559 | A1 | 2/2011 | Lum et al. |
| 2012/0232480 | A1 * | 9/2012 | Caizza ............ A61M 5/3234 604/110 |
| 2013/0006193 | A1 * | 1/2013 | Veasey ........... A61M 5/31555 604/211 |
| 2016/0206834 | A1 | 7/2016 | Shluzas et al. |
| 2016/0180480 | A1 | 8/2016 | Gross et al. |
| 2016/0220761 | A1 | 8/2016 | Shetty et al. |
| 2016/0263329 | A1 | 9/2016 | Young et al. |
| 2017/0216524 | A1 | 8/2017 | Haider et al. |
| 2018/0126085 | A1 | 5/2018 | Bowman et al. |
| 2018/0243508 | A1 | 8/2018 | Berg et al. |
| 2018/0250474 | A1 | 9/2018 | Wei |
| 2020/0306453 | A1 * | 10/2020 | Langley ............ A61M 5/31558 |

FOREIGN PATENT DOCUMENTS

| | | | |
|---|---|---|---|
| EP | 1260241 | 11/2002 | |
| EP | 2328639 B1 | 6/2011 | |
| EP | 2397173 A2 | 12/2011 | |
| JP | H08-294533 | 11/1996 | |
| JP | 2006-506166 | 2/2006 | |
| WO | WO-9300950 A1 * | 1/1993 | .......... A61M 5/3234 |
| WO | WO 96/26754 | 9/1996 | |
| WO | WO 2012/149040 A2 | 11/2012 | |
| WO | WO 2015/073991 A1 | 5/2015 | |
| WO | WO 2017/062304 A1 | 4/2017 | |
| WO | WO 2017/168287 | 10/2017 | |
| WO | WO 2017/180480 | 10/2017 | |
| WO | WO 2017/204787 | 11/2017 | |
| WO | WO 2018146589 | 8/2018 | |

OTHER PUBLICATIONS

PCT International Search Report and Written Opinion for International Appln. No. PCT/US2019/061313 dated Jun. 26, 2020.

"Mechanical Advantage", Merriam-Webster, accessed online at http://web.archive.org/web/20090422005334/https://www.merriam-webster.com/dictionary/mechanical%20advantage. Apr. 22, 2009.

Non-Final Office Action for U.S. Appl. No. 16/011,453 dated Oct. 1, 2020.

Amendment Response to NFOA for U.S. Appl. No. 16/011,453 dated Jan. 4, 2021.

PCT International Search Report and Written Opinion for PCT/US2018/038098, Applicant: Credence Medsystems, Inc., Form PCT/ISA/210 and 220, dated Nov. 6, 2018 (20 pages).

PCT International Search Report and Written Opinion for International Appln. No. PCT/US2019/061310 dated Jun. 22, 2020.

PCT International Search Report for PCT/US2021/037946, Applicant Credence Medsystems Inc., dated Oct. 6, 2021.

Foreign OA for JP Patent Appln. No. 2019-569308 dated Jul. 20, 2021.

Notice of Allowance for U.S. Appl. No. 16/011,453 dated Apr. 14, 2021.

Non-Final Office Action for U.S. Appln. No. 16/683,126 dated Jul. 27, 2021.

Amendment Response to NFOA for U.S. Appl. No. 16/683,126 dated Oct. 27, 2021.

Final Office Action for U.S. Appl. No. 16/683,157 dated Oct. 14, 2022.

Advisory Action for U.S. Appln. No. 16/683,157 dated Dec. 29, 2022.

Notice of Allowance for U.S. Appl. No. 16/683,157 dated May 4, 2023.

Foreign Examination Report for EP Patent Appln. No. 19817856 dated May 10, 2024.

Foreign Response to Examination Report for EP Patent Appln. No. 19817856 dated Nov. 11, 2024.

Foreign Amendment A Canadian application No. 3119455 dated Nov. 10, 2023.

Foreign Amendment B Canadian application No. 3119455 dated Dec. 21, 2023.

Foreign Notice of Allowance Canadian application No. 3119455 dated Nov. 25, 2024.

Foreign First Office Action Japanese application No. 2021-525107 dated Nov. 7, 2023.

Foreign Response to First Office Action Japanese application No. 2021-525107 dated Feb. 5, 2024.

Foreign Second Office Action Japanese application No. 2021-525107 dated May 14, 2024.

(56) References Cited

OTHER PUBLICATIONS

Foreign Response to Second Office Action Japanese application No. 2021-525107 dated Oct. 10, 2024.
Foreign Notice of Allowance Japanese application No. 2021-525107 dated Dec. 17, 2024.

* cited by examiner

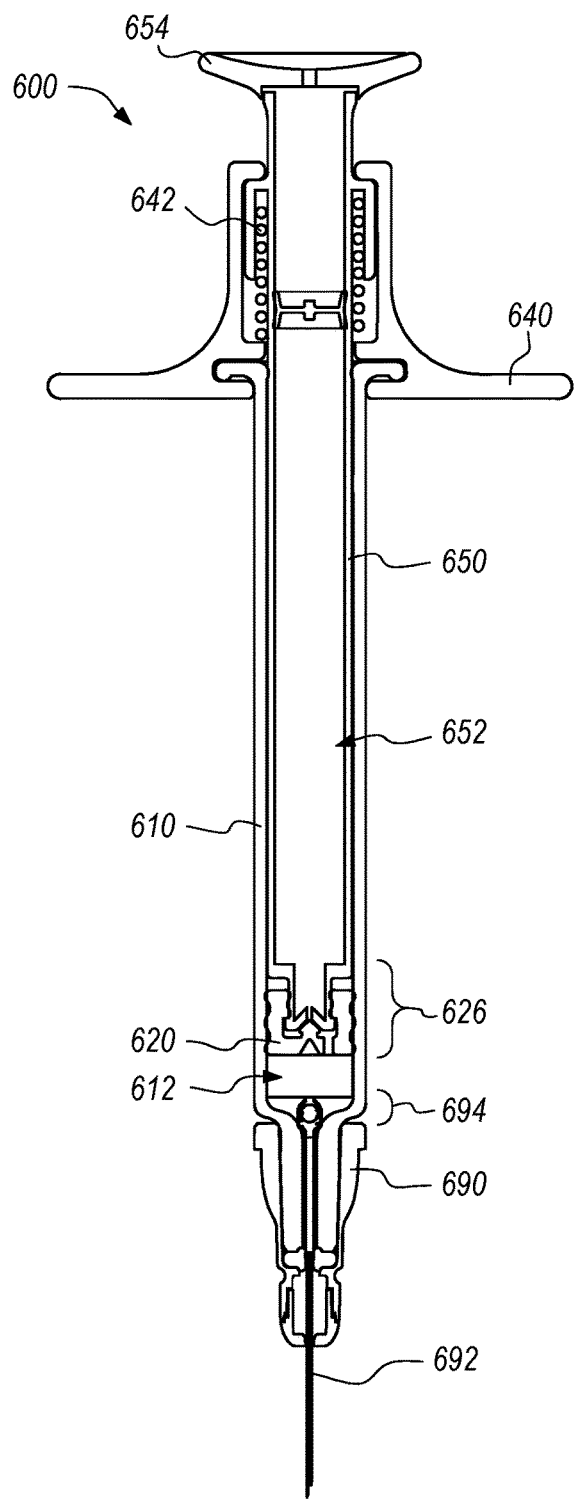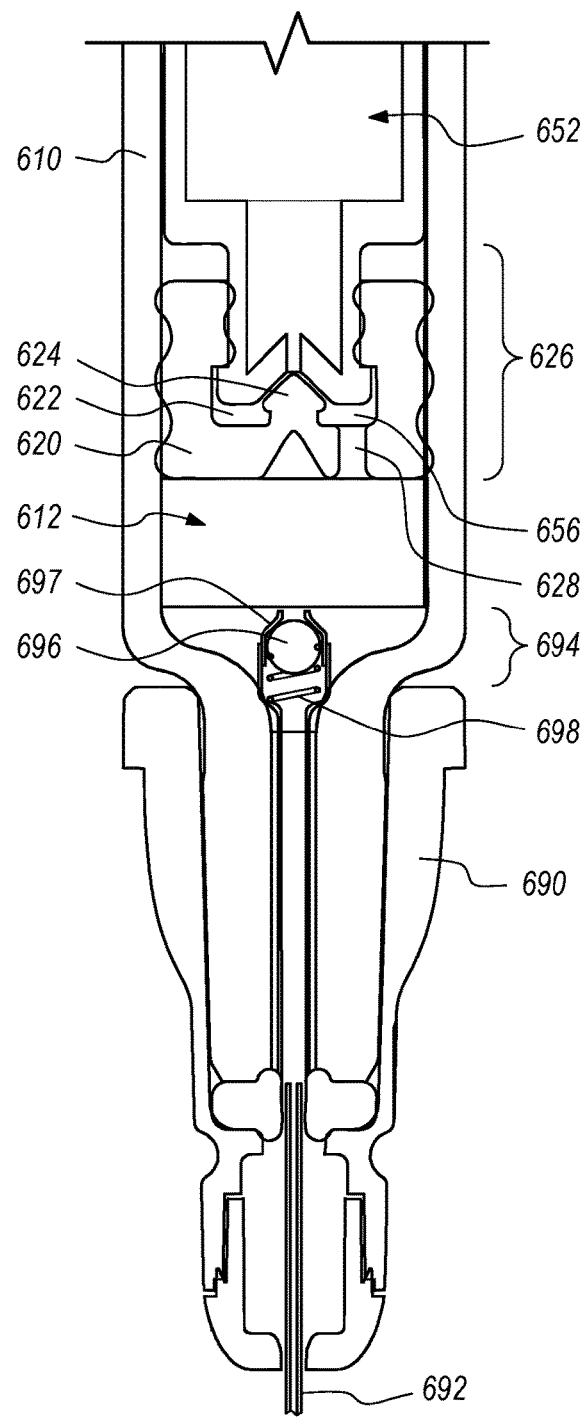
*FIG. 71*      *FIG. 72*

SYSTEM AND METHOD FOR MULTIPLE SITE INJECTION

The present application is a continuation of (1) U.S. patent application Ser. No. 16/683,157 filed on Nov. 13, 2019 entitled "SYSTEM AND METHOD FOR MULTIPLE SITE INJECTION," which claims priority to (2) U.S. Provisional Patent Application Ser. No. 62/760,273, filed on Nov. 13, 2018, and entitled "SYSTEM AND METHOD FOR SAFETY SYRINGE." This application also includes subject matter similar to the subject matter described in the following co-owned U.S. patent applications: (3) Ser. No. 14/696,342, filed Apr. 24, 2015, and entitled "SYSTEM AND METHOD FOR SAFETY SYRINGE"; (4) Ser. No. 14/543,787, filed Nov. 17, 2014, and entitled "SYSTEM AND METHOD FOR DRUG DELIVERY WITH A SAFETY SYRINGE"; (5) Ser. No. 14/321,706, filed Jul. 1, 2014, and entitled "SAFETY SYRINGE"; and (6) Ser. No. 62/416,102, filed Nov. 1, 2016, and entitled "SYSTEM AND METHOD FOR SAFETY SYRINGE"; (7) Ser. No. 62/431,382, filed Dec. 7, 2016, and entitled "SYSTEM AND METHOD FOR SAFETY SYRINGE"; (8) Ser. No. 62/480,276, filed Mar. 31, 2017, and entitled "SYSTEM AND METHOD FOR SAFETY SYRINGE; (9) Ser. No. 62/508,508, filed May 19, 2017, and entitled "SYSTEM AND METHOD FOR COLLECTING INJECTION INFORMATION"; (10) Ser. No. 62/542,230, filed Aug. 7, 2017, and entitled "CARTRIDGE SAFETY INJECTION SYSTEM AND METHODS"; (11) Ser. No. 15/801,239, filed Nov. 1, 2017, and entitled "SYSTEM AND METHOD FOR SAFETY SYRINGE"; (12) Ser. No. 15/801,259, filed Nov. 1, 2017, and entitled "SYSTEM AND METHOD FOR SAFETY SYRINGE"; (13) Ser. No. 15/801,281, filed Nov. 1, 2017, and entitled "CARTRIDGE SAFETY INJECTION SYSTEM AND METHODS"; (14) Ser. No. 15/801,304, filed Nov. 1, 2017, and entitled "SYSTEM AND METHOD FOR SAFETY SYRINGE"; (15) Ser. No. 16/011,453, filed Jun. 18, 2018, and entitled "SYSTEM AND METHOD FOR SAFETY SYRINGE"; (16) Ser. No. 15/985,354, filed May 21, 2018, and entitled "SYSTEM AND METHOD FOR COLLECTING INJECTION INFORMATION"; and "(17) Ser. No. 16/683,126, filed Nov. 13, 2019, and entitled "SYSTEM AND METHOD FOR MICRODOSE INJECTION". The contents of the above-mentioned applications are fully incorporated herein by reference as though set forth in full.

FIELD OF THE INVENTION

The present invention relates generally to injection systems, devices, and processes for facilitating various levels of control over fluid infusion, and more particularly to systems and methods related to syringes for delivery microliter range doses of fluids in healthcare environments.

BACKGROUND

Millions of syringes, such as that depicted in FIG. 1A 2, are consumed in healthcare environments every day. A typical syringe 2 includes a tubular body 4, a plunger 6, and an injection needle 8. As shown in FIG. 1B, such a syringe 2 may be utilized not only to inject fluid into a patient, but also to withdraw or expel fluid out of or into a container such as a medicine bottle, vial, bag, or other drug containment system 10. Indeed, due to regulatory constraints in some countries such as the United States as well as sterility maintenance concerns, upon use of a medicine bottle 10 with a syringe 2 as shown in a particular patient's environment, such medicine bottle may only be utilized with a single patient and then must be disposed of—causing significant medical waste from bottle and remaining medicine disposal, and even contributing to periodic shortages of certain critical drugs.

Referring to FIG. 2A, three Luer-type syringes 12 are depicted, each having a Luer fitting geometry 14 disposed distally, so that they may be coupled with other devices having similar mating geometry, such as the Luer manifold assembly 16 depicted in FIG. 2B. The Luer manifold assembly of FIG. 2B may be used to administer liquid drugs to the patient intravenously with or without the use of an intravenous infusion bag. The Luer fittings 14 of the syringes of FIG. 2A may be termed the "male" Luer fittings, while those of FIG. 2B 18 may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting 14 which are configured to engage a flange on the female fitting 18 and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during the loading to provide a Luer coupling. The use of needle injection configurations, on the other hand, carries with it the risk of a sharp needle contacting or poking a person or structure that is not desired. For this reason, so called "safety syringes" have been developed.

One embodiment of a safety syringe 20 is shown in FIG. 3, wherein a tubular shield member 22 is spring biased to cover the needle 8 when released from a locked position relative to the syringe body 4. Another embodiment of a safety syringe 24 is shown in FIGS. 4A-4B. With such a configuration, after full insertion of the plunger 6 relative to the syringe body 4, the retractable needle 26 is configured to retract 28, 26 back to a safe position within the tubular body 4, as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for pre-filled syringe assemblies such as those depicted in FIGS. 5A and 5B, which generally include a syringe body, or "drug enclosure containment delivery system", 34, a plunger tip, plug, or stopper 36, and a distal seal or cap 35 which may be fitted over a Luer type interface (FIG. 5A shows the cap 35 in place; FIG. 5B has the cap removed to illustrate the Luer interface 14. Liquid medicine may reside in the volume, or medicine reservoir, 40 between the distal seal 35 and the distal end 37 of the stopper member 36. The stopper member 36 may include a standard butyl rubber material and may be coated, such as with a biocompatible lubricious coating (e.g., polytetrafluoroethylene ("PTFE")), to facilitate preferred sealing and relative motion characteristics against the associated syringe body 34 structure and material. The proximal end of the syringe body 34 in FIG. 5B includes a conventional integral syringe flange 38), which is formed integral to the material of the syringe body 34. The flange 38 is configured to extend radially from the syringe body 34 and may be configured to be a full circumference, or a partial circumference around the syringe body 34. A partial flange is known as a "clipped flange" while the other is known as a "full flange." The flange is used to grasp the syringe with the fingers to provide support for pushing on the plunger to give the injection. The syringe body 34 preferably includes a translucent material such as a glass or polymer. To form a contained volume within the medicine chamber or reservoir 40, and to assist with expulsion of the associated fluid through the needle, a stopper member 36 may be positioned within the syringe body 34. The syringe body may define a substantially cylindrical shape (i.e., so that a plunger tip 36 having a circular cross sectional shape may establish a seal against the syringe body), or be configured to have other cross sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that 41 featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

Some medications are delivered to multiple sites in a patient during a single treatment. At the same time, after a treatment, a needle may remain exposed, increasing the probability of inadvertent needle sticks.

There is a need for injection systems which address shortcomings of currently-available configurations. In particular, there is a need for injection systems that inject fluids in multiple sites in one patient. Further, there is a need for safe injection systems that function with such multi-site injection systems. It is also desirable that such syringe assemblies may utilize the existing and relatively well-controlled supply chain of conventionally delivered pre-filled cartridges and other off-the-shelf components, and the corresponding assembly machinery and personnel.

SUMMARY

Embodiments are directed to injection systems. In particular, the embodiments are directed to microliter range injection systems that include at least some off-the-shelf syringe components.

In one embodiment, a system for injecting includes a syringe body having proximal and distal ends, a syringe interior, and a syringe flange at the proximal end thereof. The system also includes an injectable fluid disposed in the syringe interior. The system further includes a finger flange coupled to the syringe flange. Moreover, the system includes a stopper member disposed in the syringe interior. In addition, the system includes a plunger ratchet member coupled to the stopper member. The system also includes a plunger tube disposed coaxially around at least a portion of the plunger ratchet member and operatively coupled thereto.

In one or more embodiments, the system also includes a needle hub assembly coupled to the syringe body at the distal end, the needle assembly including: a non-retractable needle and a luer hub. The needle may be selected from the group consisting of 30 g needles, 32 g needles, 34 g needles, and sub 34 g needles.

In one or more embodiments, the plunger ratchet member includes needle retention feature disposed in a plunger interior, an energy-storage member disposed in the plunger interior, and an energy-storage member latching member disposed in the plunger interior. The system may also include a needle hub assembly coupled to the syringe body at its distal end. The needle assembly may include a needle having a needle proximal end feature, a hub, and a needle latching member configured to selectively prevent the needle from moving proximally relative to the hub. The needle may be at least partially retractable into the plunger interior upon manipulation of the plunger tube to transform the energy-storage member latching member from a latched state to an unlatched state. The needle may be configured to pierce entirely through the stopper member to be at least partially retracted into the plunger interior. The energy-storage member may be intercoupled between an interior surface of the plunger ratchet member and the needle retention feature. The plunger ratchet member may include a plurality of teeth disposed on an outside surface thereof. A distal end of the plunger tube may include a reduced diameter portion configured to interfere with each tooth of the plurality to prevent proximal movement of the plunger tube relative to the plunger ratchet member. The energy-storage member latching member may be configured to transform from a latched state to an unlatched state after the reduced diameter portion of the plunger tube moves distally past a proximal-most tooth of the plurality. The needle may be selected from the group consisting of 30 g needles, 32 g needles, 34 g needles, and sub 34 g needles.

In one or more embodiments, the system also includes a thumbpad coupled to a proximal end of the plunger tube. The plunger ratchet member may include a plurality of teeth disposed on an outside surface thereof. A distal end of the plunger tube may include a reduced diameter portion configured to interfere with each tooth of the plurality to prevent proximal movement of the plunger tube relative to the plunger ratchet member.

In one or more embodiments, the system also includes a ratchet retention member having a latch configured to interfere with the plurality of teeth on the plunger ratchet member to limit proximal movement of the plunger ratchet member relative to the ratchet retention member. The ratchet retention member may include a pair of elastic latches disposed on opposite sides thereof. The ratchet retention member may be formed from a sheet of metal. The finger flange may define a space sized and shaped to hold the ratchet retention member. The finger flange may also define a side opening leading into the space. The pitch of the teeth may be sized to provide a consistent injection dose per tooth. The plurality of teeth may consist of 10 teeth. The reduced diameter portion may include a plurality of leaves directed toward a longitudinal axis of the plunger tube. The plurality of leaves may consist of four leaves.

In one or more embodiments, moving the plunger tube from its proximal position to its distal position ejects a fixed volume of the fluid from the syringe interior. The finger flange may include a distal stopping surface configured to limit distal movement of the plunger tube beyond its distal position, thereby prevents ejection of more than the fixed volume of fluid from the syringe interior. The fixed volume may be approximately 0.1 ml. The stopper member may be an off the shelf stopper member. The syringe body may be an off the shelf syringe body. The plunger ratchet member may define a drive recess at a proximal end thereof.

In one or more embodiments, the finger flange includes a proximally extending tube disposed coaxially around a portion of the plunger tube, and a return spring configured to bias the plunger tube from a distal position to a proximal position. The plunger tube may include a proximal flange configured to limit distal movement of the plunger tube relative to the proximally extending tube of the finger flange. The plunger tube may include a plurality of tabs directed away from a longitudinal axis of the plunger tube. The proximally extending tube of the finger flange may define a corresponding plurality of windows configured to interfere with the plurality of tabs to limit proximal movement of the plunger tube relative to the proximally extending tube of the finger flange. The plunger tube may be disposed coaxially within the syringe body. The system may also include a priming screw configured to advance the plunger ratchet member to remove air from the syringe interior and eject a portion of the injectable fluid from the syringe interior.

In one or more embodiments, the finger flange includes a lever, the plunger ratchet member is operatively coupled to the lever, and the plunger tube is operatively coupled to the lever. The plunger tube may be disposed coaxially within the syringe body. The finger flange may also include a link coupling the plunger tube to the lever. The finger flange may also include a spring operatively coupled to the lever. The lever may have a proximal position and a distal position. The spring may bias the lever in the proximal position.

In one or more embodiments, the plunger tube has a proximal position corresponding to the proximal position of the lever and a distal position corresponding to the distal position of the lever. The spring may bias the plunger tube in the proximal position. Moving the plunger tube from its proximal position to its distal position may move the lever from its proximal position to its distal position and may move the plunger ratchet member distally relative to the finger flange. The finger flange may include a distal stopping surface configured to limit distal movement of the plunger tube beyond its distal position, thereby prevents ejection of more than the fixed volume of fluid from the syringe interior.

In one or more embodiments, moving the plunger tube from its proximal position to its distal position by a first distance moves the plunger ratchet member distally relative to the finger flange by a second distance, thereby dispensing the injectable fluid from the syringe body. A ratio of the first distance to the second distance may be in the range of 1 to 5. The ratio of the first distance to the second distance may be approximately 2.5.

In one or more embodiments, applying a first force to the plunger tube applies a second force to the plunger ratchet member, wherein a ratio of the second force to the first force is a force ratio. The force ratio may be in the range of 1 to 5. The force ratio may be approximately 2.5. The force ratio may reduce the amount of force applied to the plunger tube to inject viscous medicine through a needle. The plunger tube and the plunger ratchet member may define a space at a proximal end of the plunger tube when the plunger tube is in its proximal position.

In one or more embodiments, the plunger ratchet member has a smooth exterior surface, and the plunger tube includes a pair of inwardly biased members configured to allow distal movement of the plunger ratchet member relative to the plunger tube, while preventing proximal movement of the plunger ratchet member relative to the plunger tube. The pair of inwardly biased members may be configured to deform a surface of the plunger ratchet member.

In another embodiment, a method for assembling a system for injecting includes mounting a finger flange to a pre-filled syringe. The pre-filled syringe includes a syringe body defining a syringe interior, an injectable fluid disposed in the syringe interior, and a stopper member disposed in the syringe interior and retaining the injectable fluid in the syringe interior. The finger flange includes a plunger tube have a proximal opening therein. The method also includes inserting a plunger ratchet member through the proximal opening into the plunger tube. The method further includes coupling the plunger ratchet member to the stopper member in the syringe interior.

In one or more embodiments, the method also includes capping the proximal opening in the plunger tube with a thumb pad. The plunger ratchet member may include a plurality of teeth disposed on an outside surface thereof. A distal end of the plunger tube may include a reduced diameter portion configured to interfere with each tooth of the plurality to prevent proximal movement of the plunger tube relative to the plunger ratchet member. The method may also include inserting a plunger ratchet member through the proximal opening into the plunger tube until a distal most tooth of the plurality of teeth moves distally past the reduced diameter portion to thereby limit proximal movement of the plunger ratchet member relative to the plunger tube and finger flange.

In one or more embodiments, the finger flange includes a proximally extending tube disposed coaxially, and a return spring configured to bias the plunger tube from a distal position to a proximal position. The method may also include inserting the plunger tube into the proximally extending tube thereby compressing the return spring. The finger flange may include a lever, and a link operatively coupled to the lever. The method may also include inserting the plunger tube into the finger flange thereby operatively coupling the plunger tube to the lever via the link.

In still another embodiment, a system for injecting includes a syringe body having proximal and distal ends, a syringe interior, and a syringe flange at the proximal end thereof. The system also includes a finger flange coupled to the syringe flange, the finger flange including a plunger return spring. The system further includes a stopper member disposed in the syringe interior. Moreover, the system includes a plunger member coupled to the stopper member and operatively coupled to the plunger spring. The plunger member has a proximal position and a distal position. The plunger spring biases the plunger member in the proximal position.

In one or more embodiments, when the plunger member is in the proximal position, the stopper member and the syringe body define a distal chamber. The plunger member may have a proximal chamber. The stopper member and a distal end of the plunger member may form a proximal one-way valve configured to fluidly couple the proximal and distal chambers when the plunger member is in the proximal position, and to fluidly isolate the proximal chamber from the distal chamber when the plunger member is in the distal position. The system may also include a distal one-way valve configured to fluidly couple the distal chamber and an opening at the distal end of the syringe body when the plunger member is in the distal position, and to fluidly isolate the distal chamber from the opening when the plunger member is in the proximal position. The stopper member may define a space. The distal end of the plunger member may be movably disposed in the space to movably couple the plunger member to the stopper member. The distal one-way valve may include a spherical member and a valve spring biasing the spherical member in a proximal position to close the distal one-way valve. Moving the plunger member from the distal position to the proximal position may close the distal one-way valve and opens the proximal one-way valve to allow a fluid in the proximal chamber to flow into the distal chamber.

In one or more embodiments, moving the plunger member from the proximal position to the distal position closes the proximal one-way valve and opens the distal one-way valve to allow a fluid in the distal chamber to flow out of the distal opening of the syringe body. Moving the plunger member from the proximal position to the distal position may eject a fixed volume of fluid from the distal chamber out of the distal opening of the syringe body. The fixed volume may be approximately 0.1 ml. The needle may be selected from the group consisting of 30 g needles, 32 g needles, 34 g needles, and sub 34 g needles. The system may also include a thumbpad coupled to a proximal end of the plunger member. The syringe body may be an off the shelf syringe body.

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein:

FIGS. 6-15C illustrate various aspects of a multiple site injection system and a multiple site injection method according to some embodiments.

FIGS. 68-74 illustrate various aspects of a multiple site injection system and a multiple site injection method according to some embodiments.

Figure 1A:
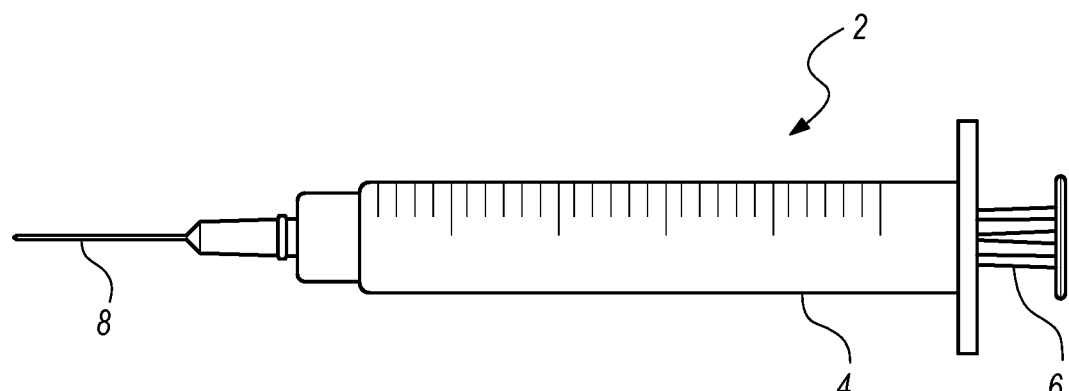
FIGS. 1A-5C illustrate various aspects of conventional injection syringe configurations.
Figure 1B:
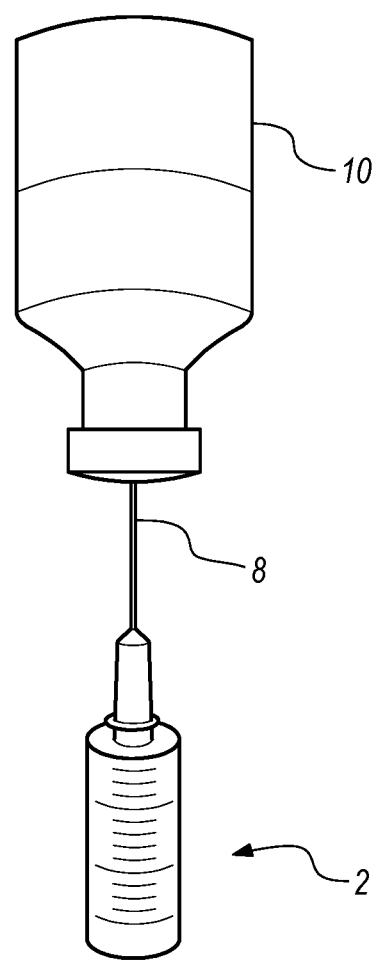
Figure 2A:
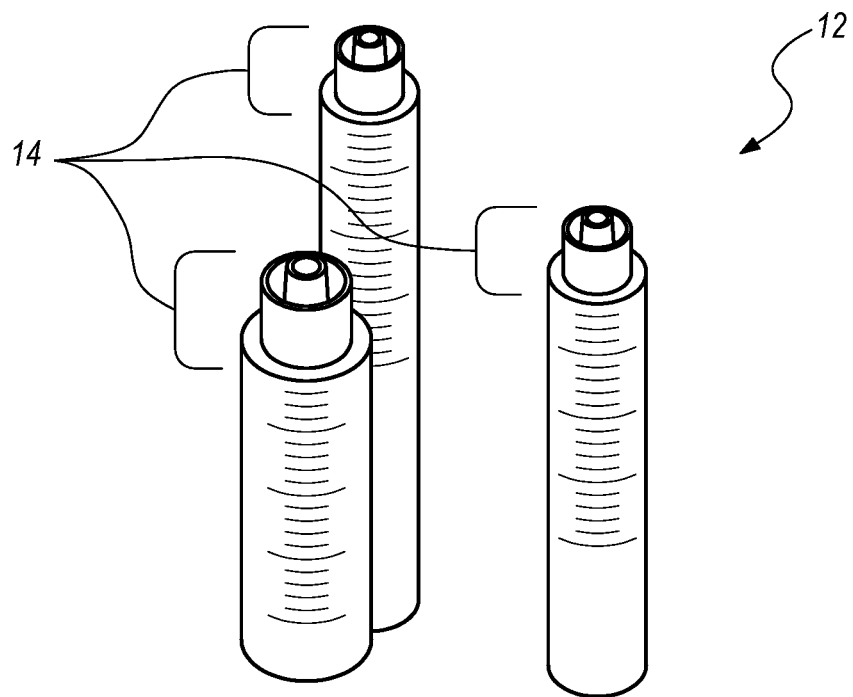
Figure 2B:
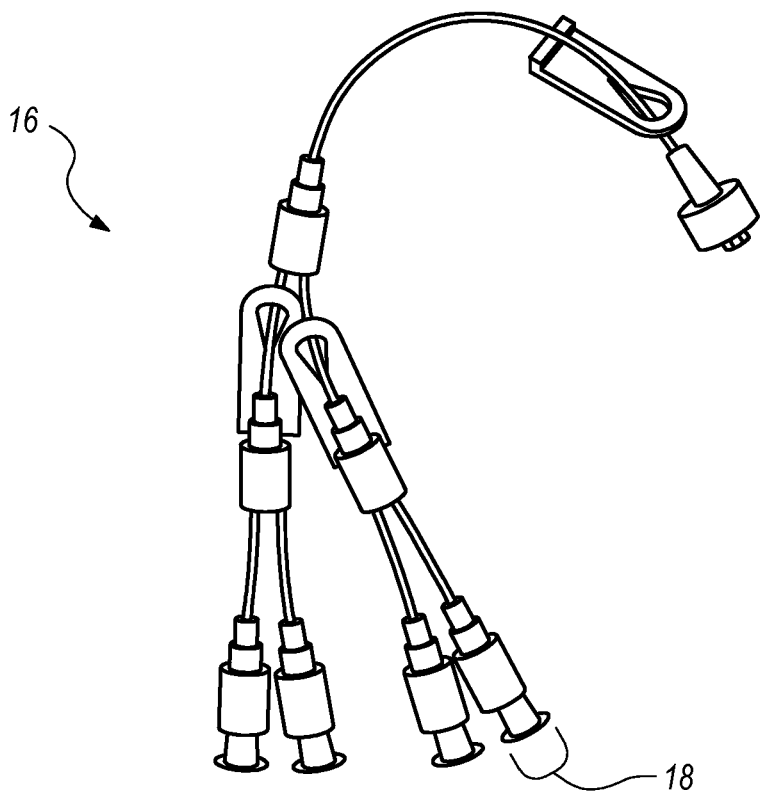
Figure 3:
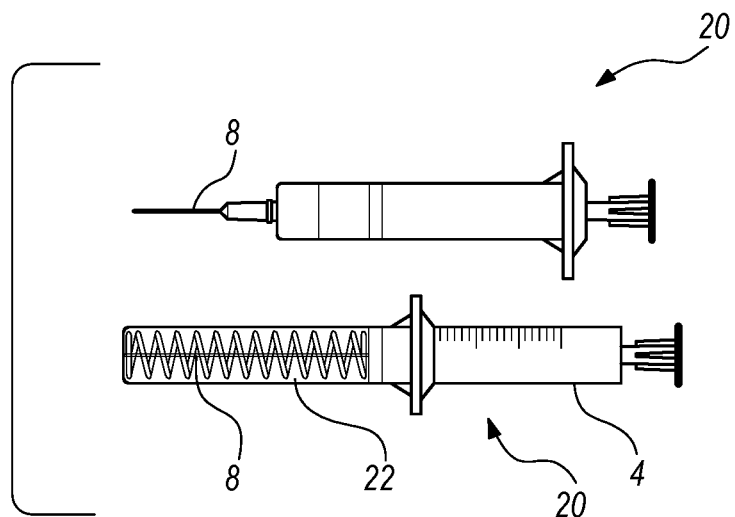
Figure 4A:
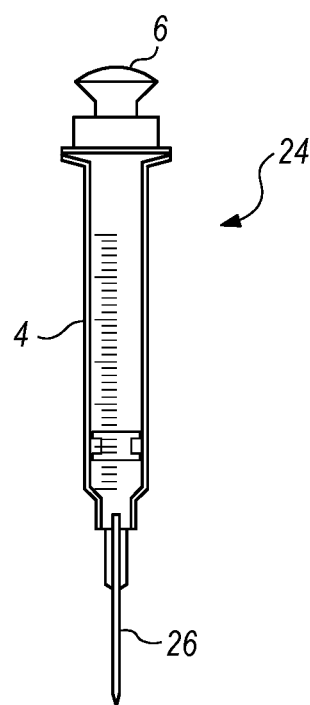
Figure 4B:
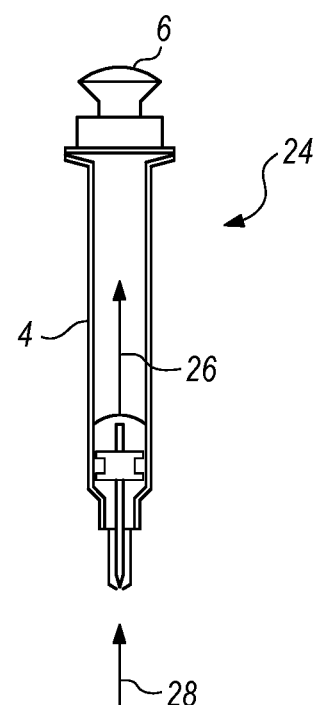
Figure 5A:
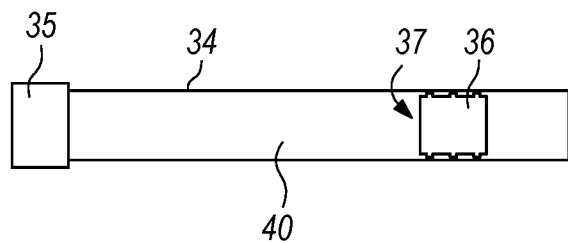
Figure 5B:
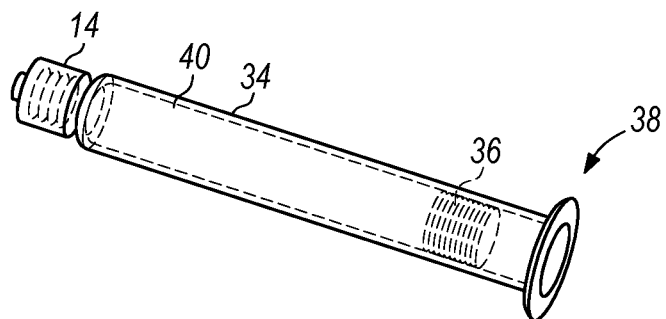
Figure 5C:
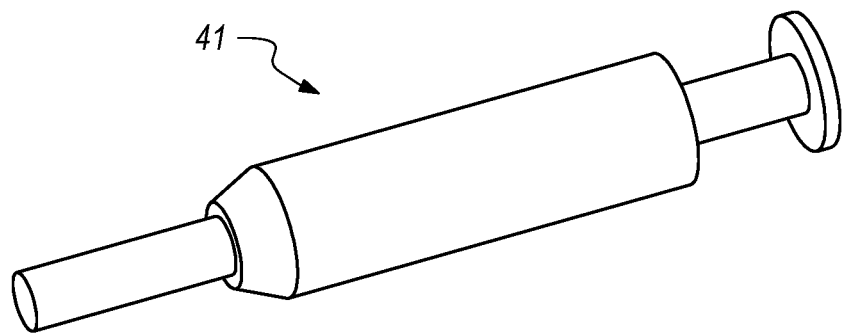

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Multiple Site Injection Systems

Many injectable medications can be administered to multiple injection sites on the same patient. Some medical procedures involve injection of fixed volumes (e.g., 0.1 ml and/or microdose volumes) of medications (e.g., botulinum toxin or "Botox") at multiple injection sites on a patient. Currently, many medicines are drawn into an injection system from a vial, which increases procedure time and exposure of a needle for unintended punctures. Further, some medications are delivered in a viscous solution, and therefore require a larger diameter (e.g., lower gauge: 25 g) needle to be used to draw the viscous medication into the injection system and a smaller diameter (e.g., higher gauge: 30 g, 32 g, 34 g, sub-34 g) needle to be use for the injection. This exchange of needles results in increased procedure time and risk of unintended punctures. The multiple site injection system described herein addresses these issues of current systems.

Figure 6:
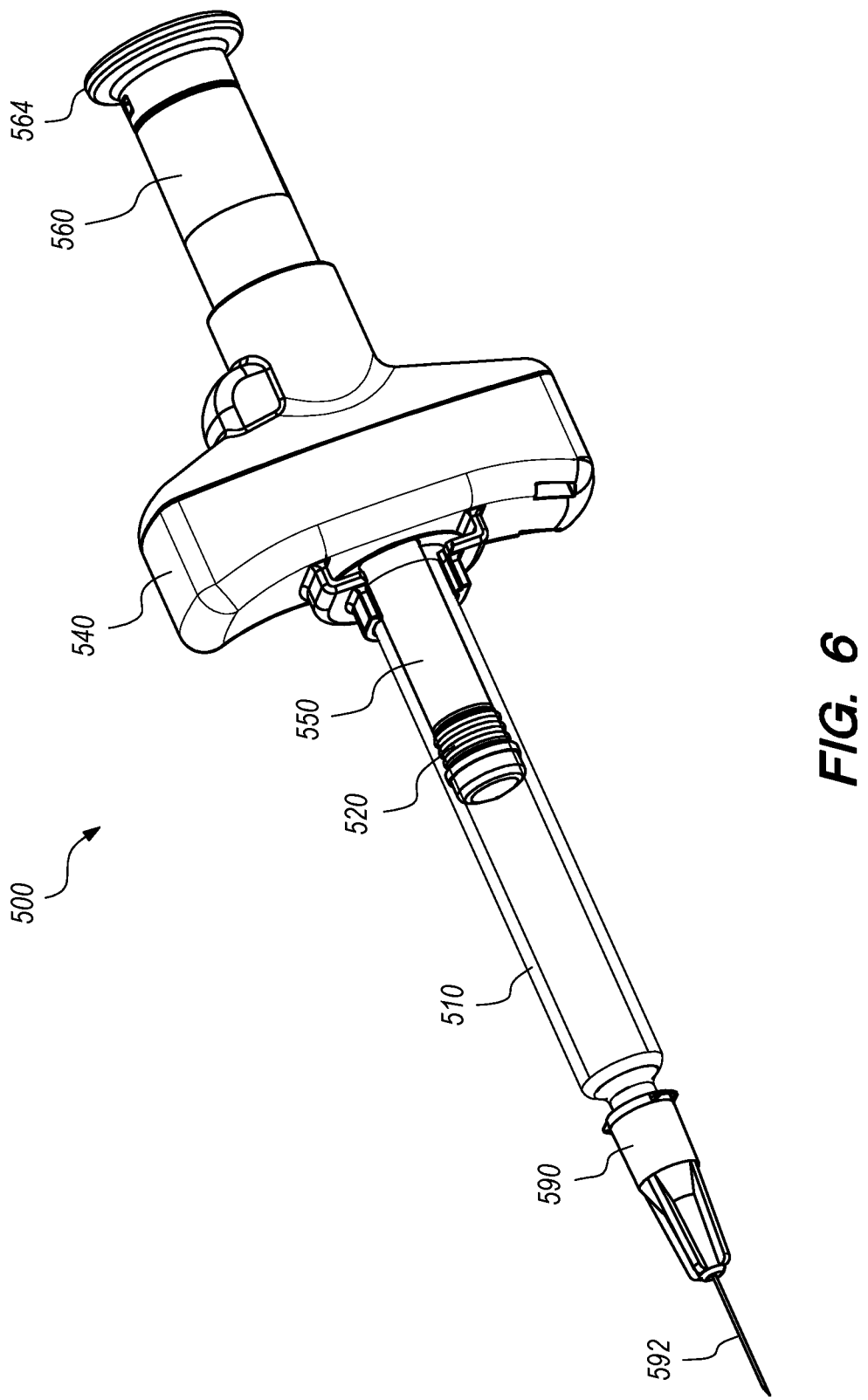

FIGS. 6-15C depict a multiple site injection system 500 according to some embodiments. As shown in FIG. 6, the system 500 can be prefilled with an injectable medication. The system 500 includes a syringe body 510, a needle assembly 590, a stopper member 520, a plunger member 550, and a finger flange 540. Many of these system components (e.g., the syringe body 510, the stopper member 520, and needle member 590) may be off-the-shelf components to utilize the existing and relatively well-controlled supply chain, and the corresponding assembly machinery and personnel. The syringe body 510 may be glass, metal, or polymeric materials such as COC, COP, polypropylene, polyethylene, or other syringe material. The stopper member 520 may be rubber such as butyl, chlorobutyl, bromobutyl, or a polymeric material such as a thermoplastic elastomer. The stopper member 520 may be covered in a protective and/or lubricious coating such as PTFE or other polymer. The stopper member 520 being off-the-shelf refers to a commercially available stopper member, which has a generally smooth distally facing surface which contains no projections or recesses for coupling to a needle. The system 500 also includes a plunger tube 560 configured to apply distally directed force to the plunger member 550 and the stopper member 520 coupled thereto.

Figure 7:
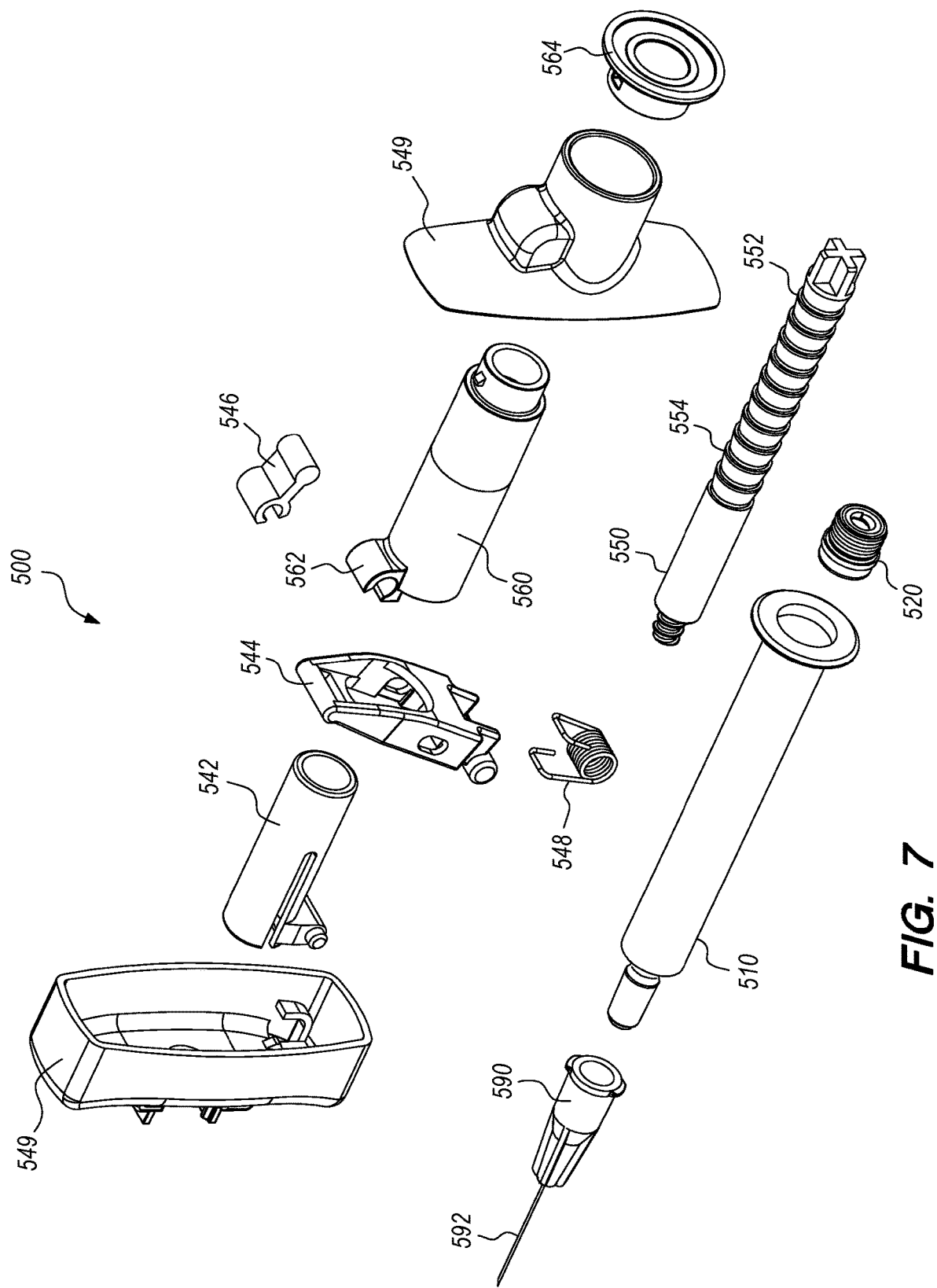
Figure 8:
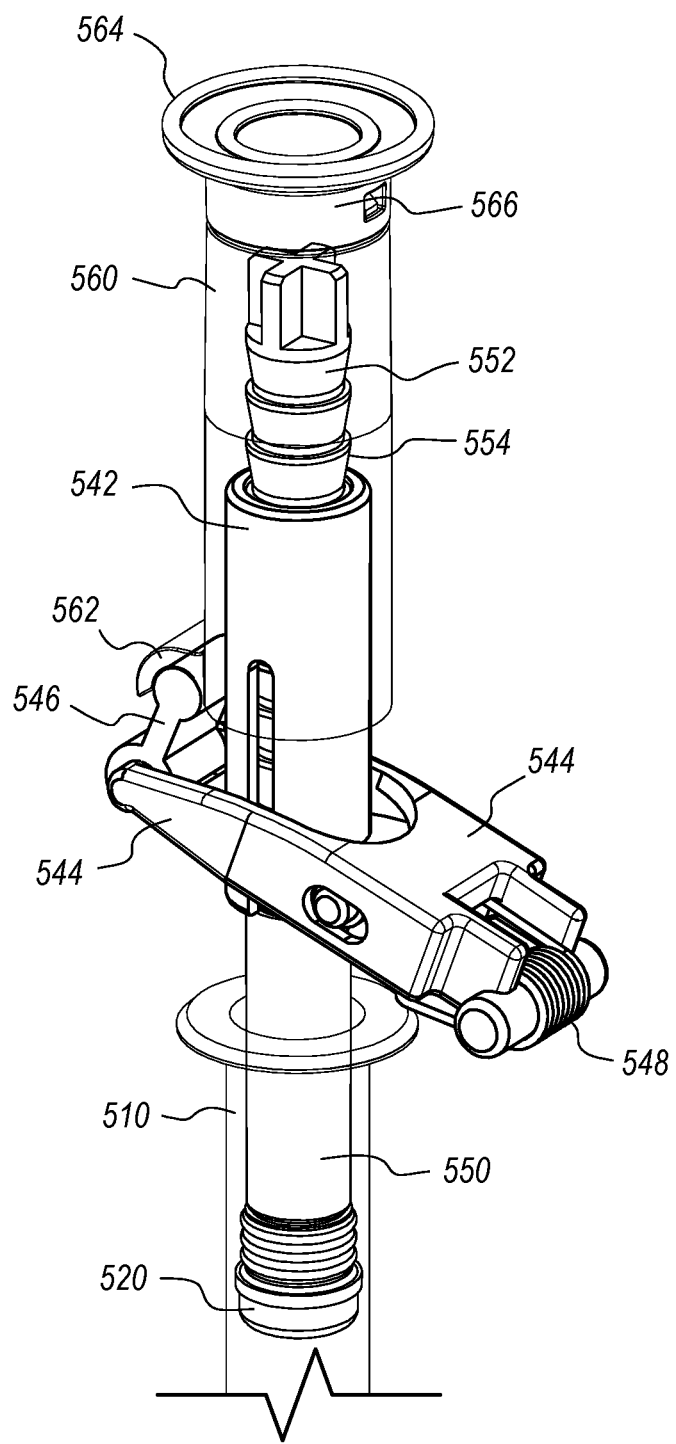
Figure 9:
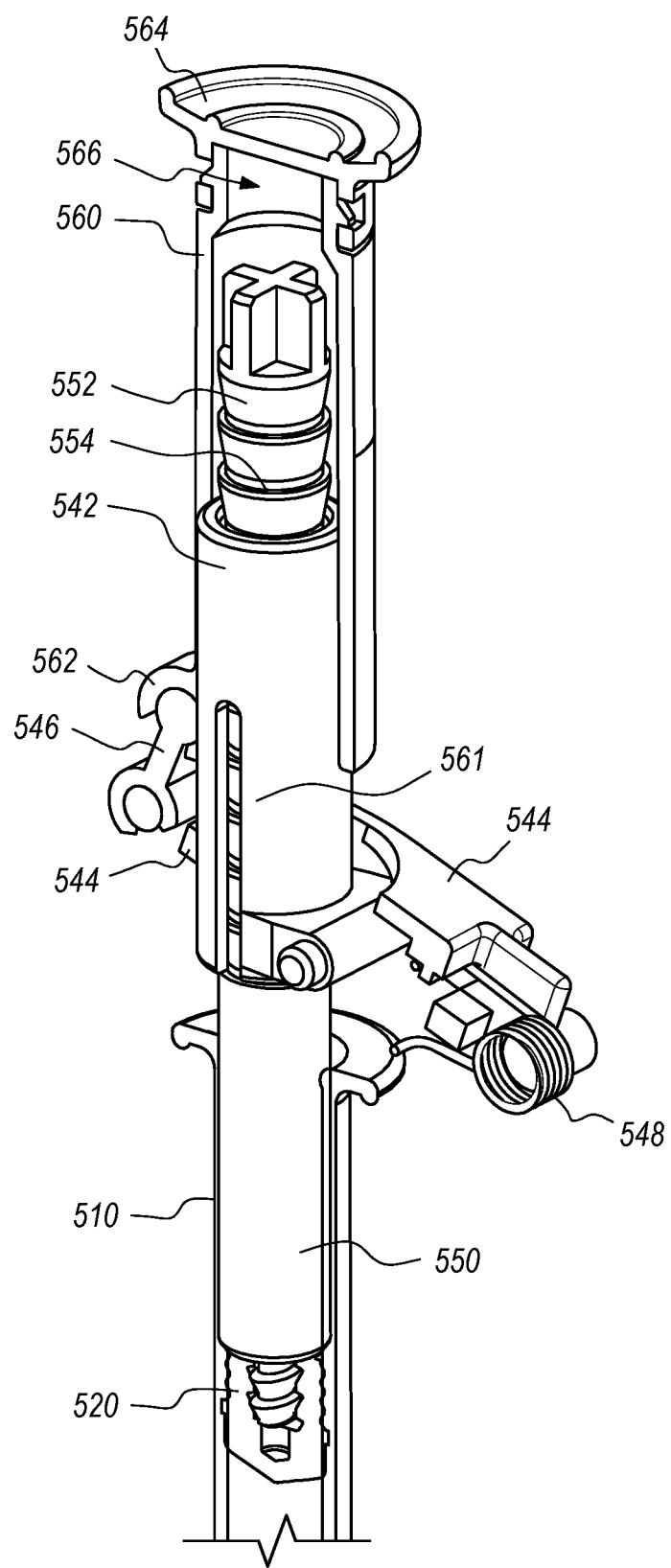
Figure 10:
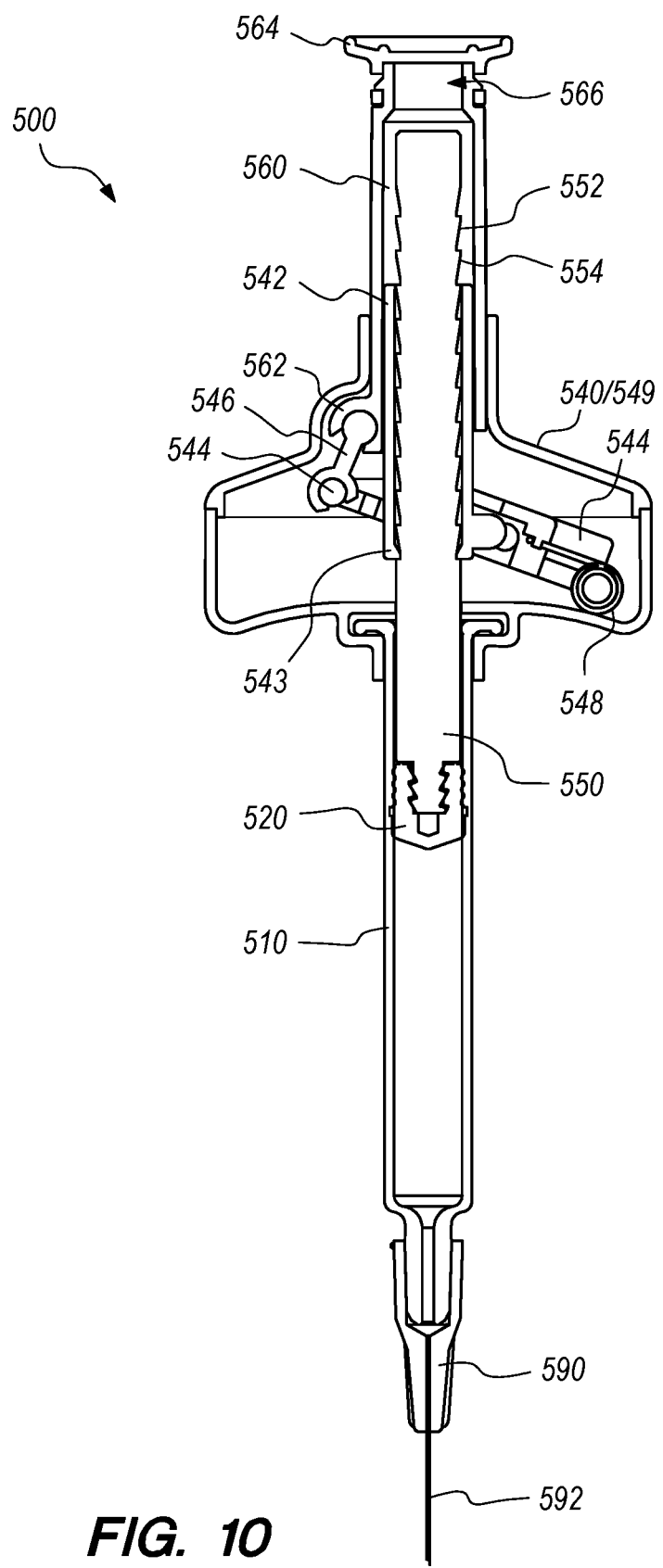
Figure 11:
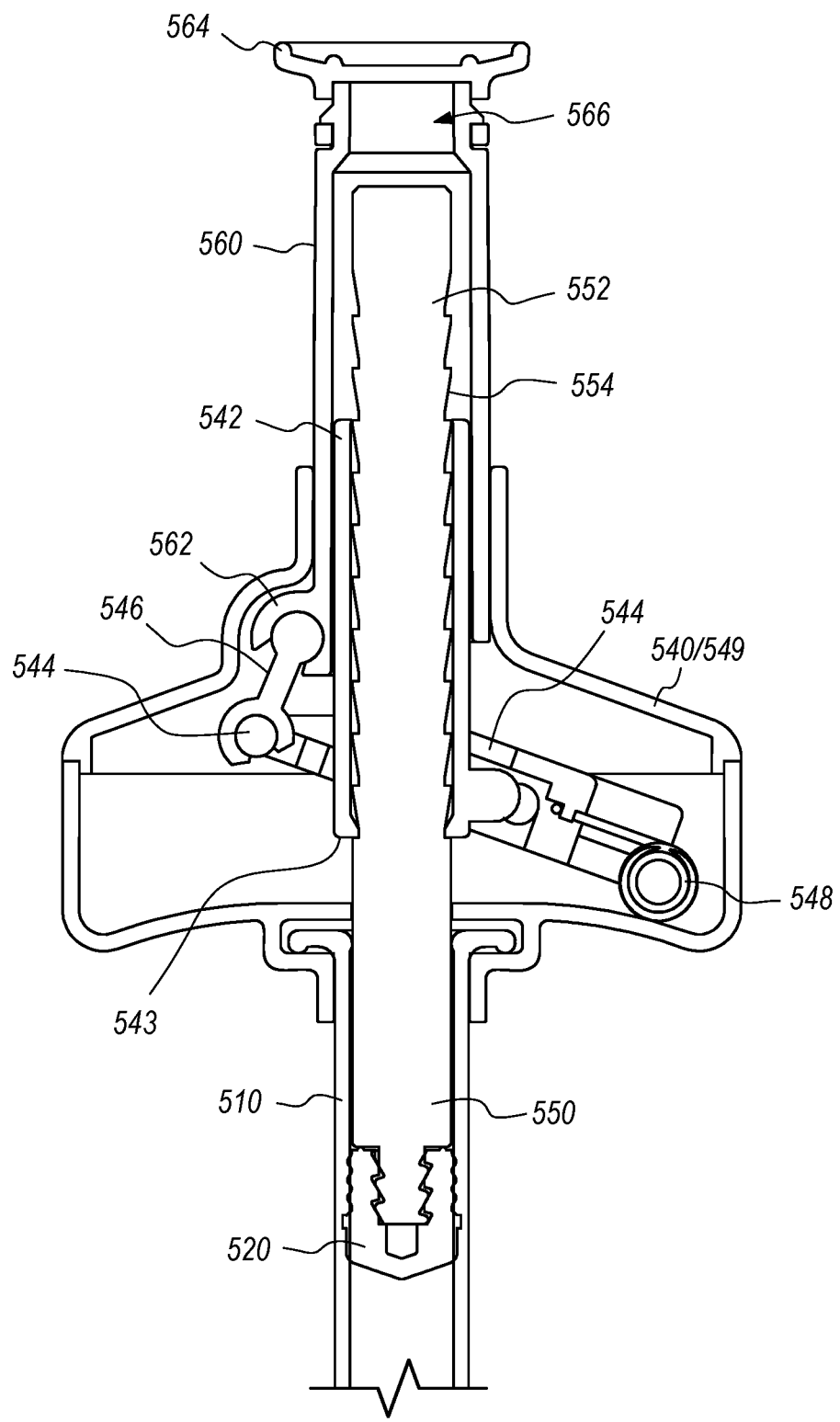

FIG. 7 is an exploded view, FIGS. 8 and 9 are detailed perspective views, FIGS. 10 and 11 are detailed partial longitudinal cross-section views, all showing various internal components of the multiple site injection system 500 according to some embodiments. The finger flange 540 includes a ratchet pawl 542, a lever arm 544, a link 546, and a return spring 548, which are all contained in a flange housing 549. The plunger tube 560 includes an arm 562 and a thumb pad 564. The plunger member 550 includes a ratchet surface 552 having a plurality of teeth 554.

When assembled as shown in FIGS. 8-11, the thumb pad 564 is operatively coupled to the ratchet pawl 542 through the plunger tube 560, the arm 562, the link 546, and the lever arm 544. As such, when distally directed force is applied to the thumb pad 564, the lever arm 544 increases and transmits the distally directed force to the ratchet pawl 542. Depending on the relative dimensions of the lever arm 544, the ratio of the distances traveled by the plunger tube 560 and the plunger member 550 may be anywhere from about one to about five. In one embodiment, the distance ratio is approximately 2.5:1. Similarly, the force ratio of the force applied to the thumb pad 564 and the force exerted on the ratchet pawl 542 may be anywhere from about one to about five. In one embodiment, the force ratio is approximately 2.5:1.

The return spring 548 biases the lever in the proximal direction. Accordingly, after a user presses the thumb pad 564 to move the plunger tube 560 distally, releasing the pressure on the thumb pad 564 allows the thumb pad 564 and the plunger two 562 return to a proximal position. As shown in FIGS. 10 and 11, the ratchet pawl 542 includes a reduced diameter section 543 at a distal end thereof. This reduced diameter section 543 interferes with the teeth 554 on the ratchet surface 552 of the plunger member 550, which allows the ratchet pawl 542 to move proximally, but not distally, relative to the plunger member 550. In the distal direction, the ratchet pawl 542 can apply the force to the plunger member 550. As shown in FIG. 9, the ratchet pawl 542 further includes a plurality of slots 561 configured to allow the reduced diameter section 543 to expand radially upon return of the plunger tube 560 to allow the ratchet pawl 542 to engage the next adjacent plunger member 550 ratchet tooth 554. When the return spring 548 moves the ratchet pawl 542 proximally, the reduced diameter section 543 and the slots 561 are configured to allow the ratchet pawl 542 to move proximally over the plunger member 550. The lever arm 544 is configured such that moving the ratchet pawl 542 from a distal position to a proximal position moves the reduced diameter section 543 thereof from one tooth 554 to the next tooth 554 in a proximal direction. This moves the plunger member 550 distally by a distance of one tooth 554. The various components of the system 500 can be configured such that moving the plunger member 550 distally by a distance of one tooth 554 ejects a predetermined volume (e.g., 0.1 ml, microdose) of fluid from an interior of the syringe body 510. The spacing between ribs/teeth 554 may be constant along the length of the plunger member 550 to deliver constant doses per injection or may be variable along the length of the plunger member 550 to deliver different doses per injection. Consequently, a user can serially advance the plunger member 550 in the syringe body 510 and eject a predetermined volume of fluid by alternately depressing and releasing the thumb pad 564.

Figure 12:
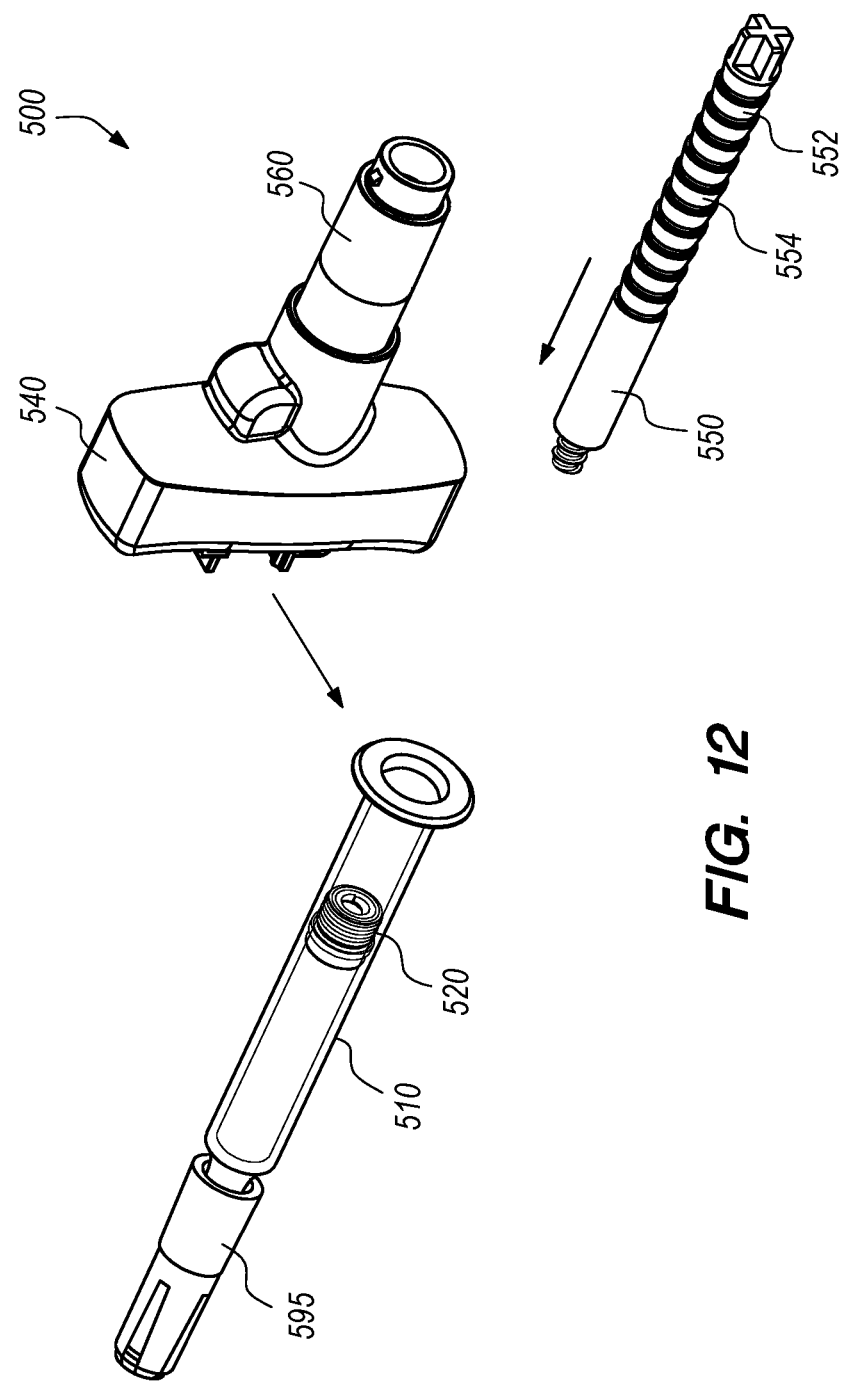
Figure 13:
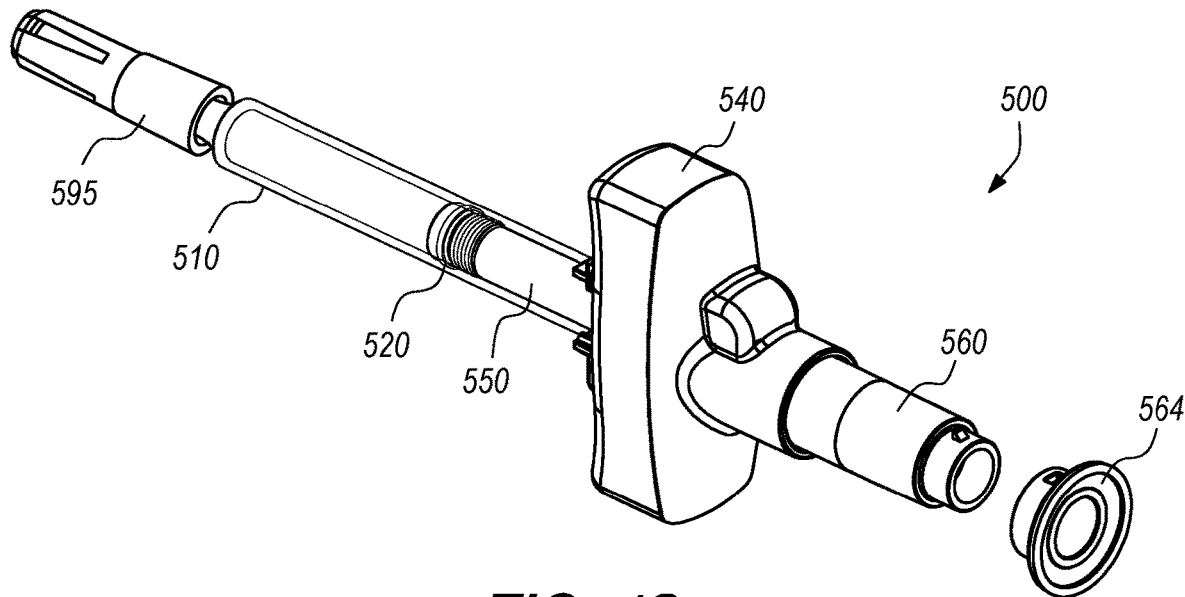
Figure 14:
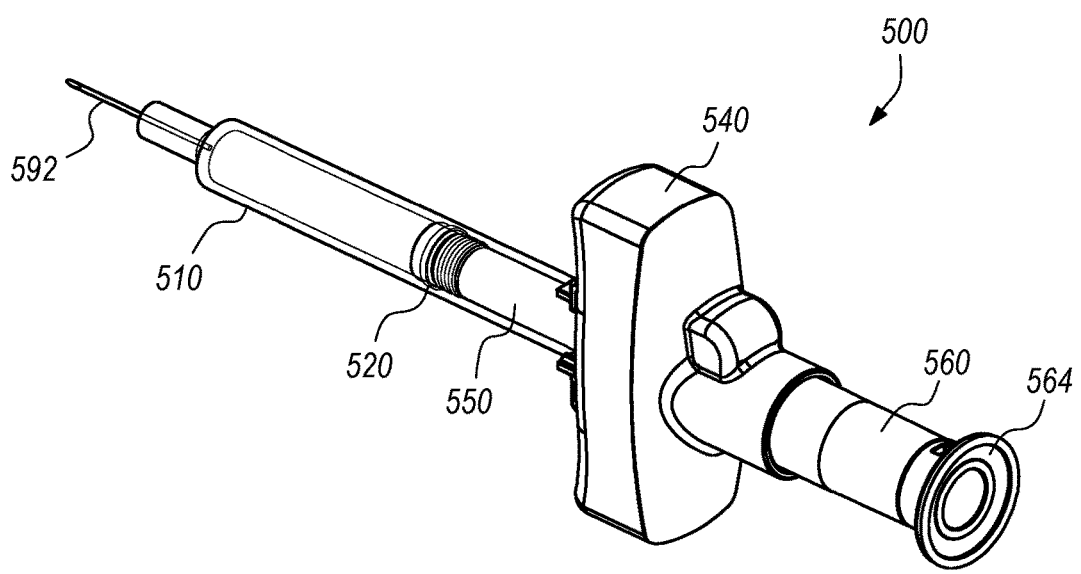
Figure 15:
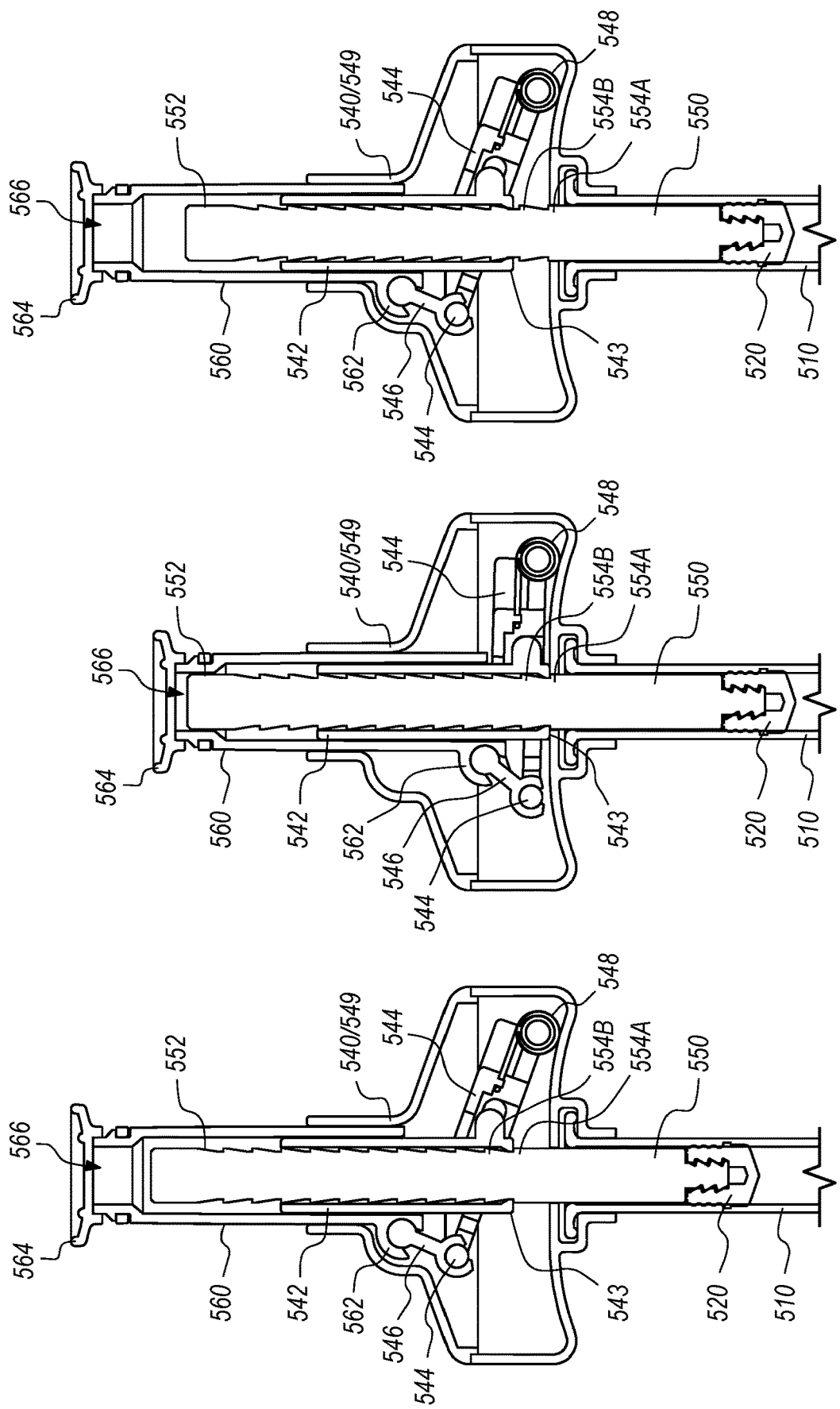
Figure 16:
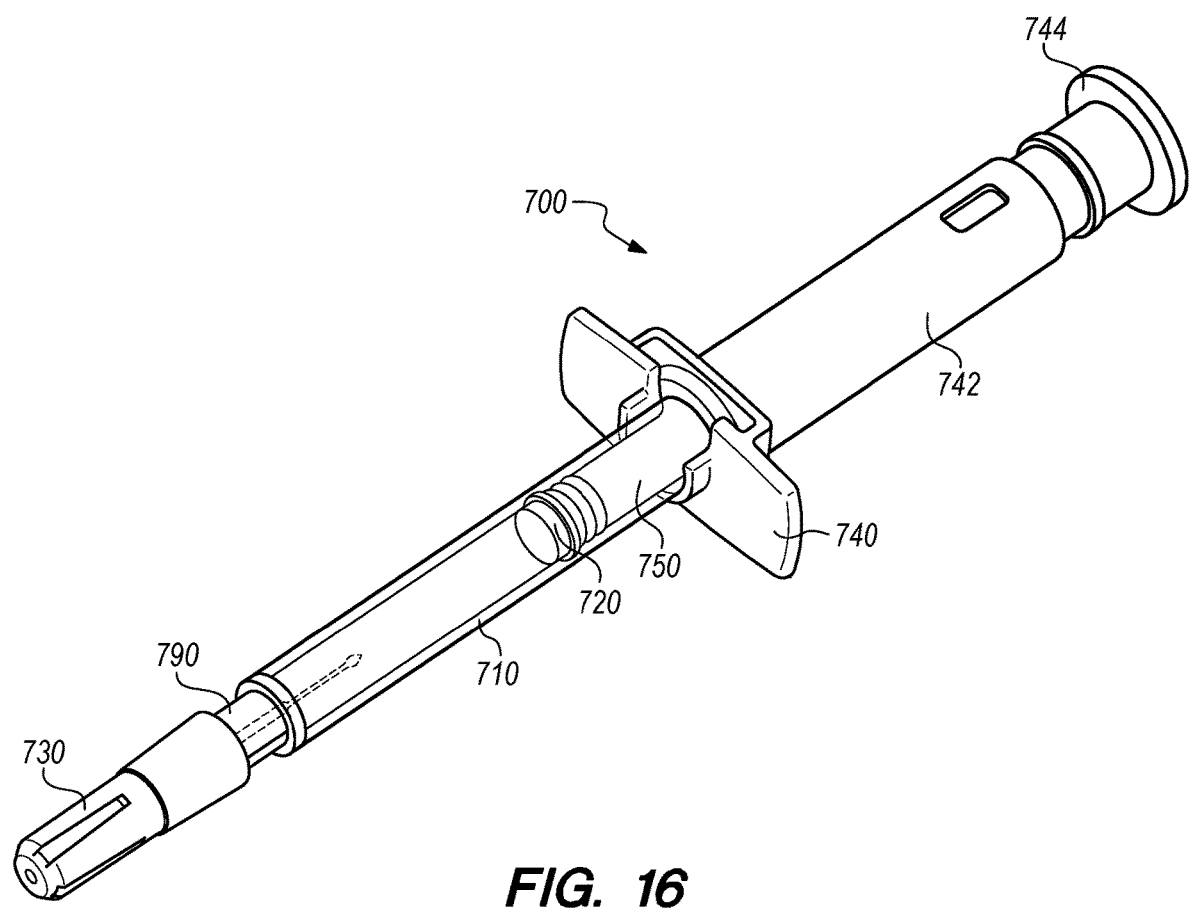
FIGS. 16-28 illustrate various aspects of a multiple site injection system and a multiple site injection method according to some embodiments.
Figure 17:
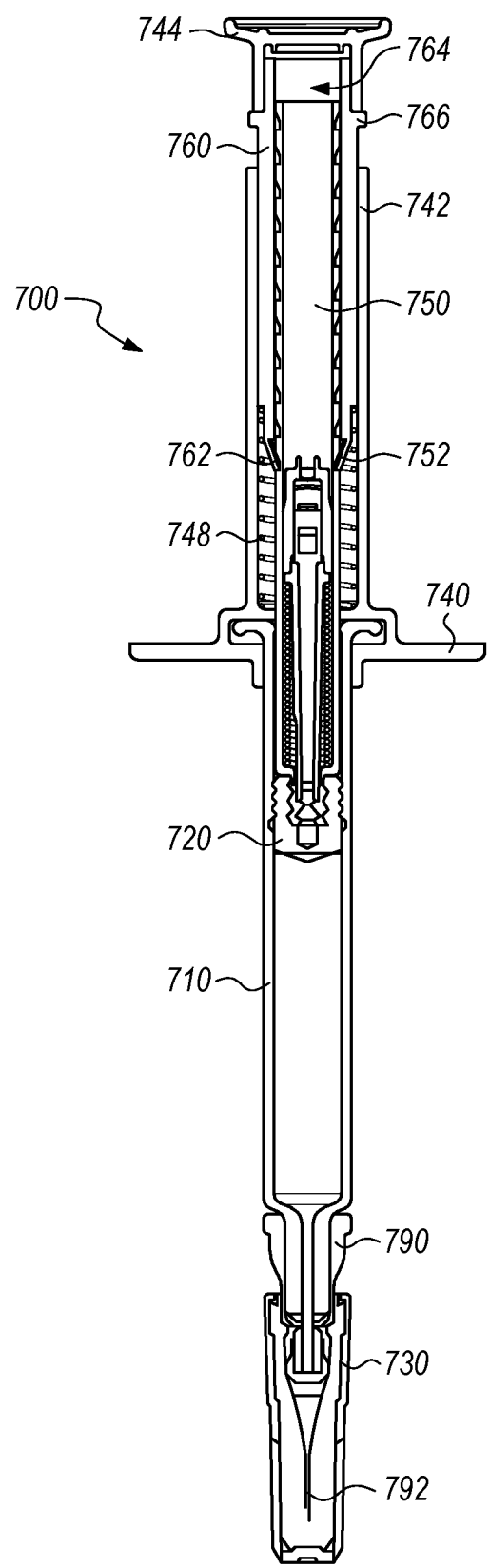

FIGS. 12-14 depict assembly of a multiple site injection system 500 according to some embodiments. In FIG. 12, plunger tube 560 has been inserted coaxially around the ratchet pawl 542 and into the finger flange 500 until the arm 562 on the plunger tube 560 engages and the link 546 attached to the lever arm 544. The finger flange 540 is snapped onto a prefilled and pre-stoppered syringe 510. The plunger rod 550 is then inserted into the finger flange 540 through the plunger tube 560 and coupled (e.g., screwed or pressed into) to the stopper member 520. The thumbpad 564 may then be snapped onto the plunger tube 560 to complete the assembly. The system 500 depicted in FIGS. 12-14 include a pre-attached staked needle 592. The needle 592 is provided to the end user covered in a needle shield 595. The needle shield 595 may be constructed of a rubber internal needle contacting component and a plastic outer covering. Alternate needles may be of the user attached luer type, or pre-attached retractable safety needles.

In FIG. 13, a lateral opening in the finger flange 540 is slid over the glass flange of the syringe body 510 to removably couple the finger flange 540 to the syringe body 510. The plunger member 550 is inserted through the finger flange 540, the plunger tube 560, and the ratchet pawl 542 until the reduced diameter section 543 of the ratchet pawl 542 engages the distal most tooth 554 on the plunger member 550. This engagement can be determined either by a distance, audio, and/or tactile indicator that the reduced diameter section 543 has moved over a distal most tooth 554 of the longer member 550.

In FIG. 14, the thumb pad 564 is coupled to a proximal end of the plunger tube 560 to complete the assembly. After the thumb pad 564 is coupled to the plunger tube 560, the multiple site injection system 500 is ready for use. The needle shield 595 has been removed to administer the injection FIGS. 15A-15C depict an injection of a first dose of a plurality of doses (e.g., microdoses) using the multiple site injection system 500 depicted in FIGS. 6-14. In FIG. 15A, the multiple site injection system 500 has been assembled and is ready for use. The return spring 548 is biasing the lever arm 542 in a proximal position. The plunger member 550 has been inserted until a distal most tooth 554A has moved distally past and is engaging the reduced diameter section 543 of the ratchet pawl 542.

FIG. 15B shows the result of a user applying a distally directed force to the thumb pad 564. The distally directed force is transmitted through the arm 562 at the distal end of the plunger tube 562 to the link 546 and onto the lever arm 544, which moves from its proximal position (see FIG. 15A) to its distal position (see FIG. 15B). As the lever arm 544 moves from its proximal to its distal position, the ratchet pawl 542 moves distally relative to the finger flange 540 and the syringe body 510 coupled thereto. An interference between the reduced diameter section 543 of the ratchet pawl 542 and the distal most tooth 554A causes the plunger member 550 to move distally along with the ratchet pawl 542. Because the ratchet pawl 542 and the plunger member 550 move distally a shorter distance than the plunger tube 560, there is a space 566 at the proximal end of the plunger tube 560 to accommodate the proximal end of the plunger member 550 can move as the plunger tube 560 moves distally over the plunger member 550. As the plunger member 550 to move distally relative to the syringe body 510, the stopper member 520 coupled thereto also moves distally relative to the syringe body 510, thereby ejecting a fixed dose volume of fluid from the syringe body 510 and out through the needle assembly 590.

FIG. 15C shows the result of the user releasing the distally directed force from the thumb pad 564. The return spring 548 moves the lever arm 544 from its distal position (see FIG. 15B) to its proximal position (see FIG. 15C). As the lever arm 544 moves proximally, it moves both the ratchet pawl 542 and the plunger tube 560 proximally. As the ratchet pawl 542 moves proximally, the elastic nature of the reduced diameter section 543 thereof allows it to expand and slide proximally over the slanted penultimate distal tooth 554B. The system 500 is configured such that each depression of the thumb pad 564 and plunger tube 560 moves the plunger member 550 distally by the distance of one tooth 554. Accordingly, after the lever arm 544 has returned to its proximal position, the reduced diameter section 543 of the ratchet pawl 542 is now engaged with the next tooth 554 in the distal direction (i.e., 554B) on the plunger member 550.

As such, the multiple site injection system 500 shown in FIG. 15C is ready for another injection. The injection process shown in FIGS. 15A-15C can be repeated to give a series of injections having a fixed volume (e.g., 0.1 ml, microdose) until the plunger member 550 has moved distally until the proximal most tooth 554 has move distally past and is no longer engaged with the reduced diameter section 543 of the ratchet pawl 542. Although not shown in the figures, after the multiple site injection system 500 has delivered its last injection, the needle 592 in the needle assembly 590 may be retracted proximally completely through the stopper member 520 and at least partially into the plunger member 550 so that the sharp end of the needle 592 is no longer exposed to minimize unintended needle punctures. Such needle retraction systems are shown in co-owned U.S. patent application Ser. Nos. 14/696,342, 14/543,787, 14/321,706, 62/416,102, 62/431,382, 62/480,276, 62/508,508, 62/542,230, 15/801,239, 15/801,259, 15/801,281, 15/801,304, the contents of which were previously fully incorporated herein by reference as though set forth in full.

FIGS. 16-28 depict a multiple site injection system 700 according to some embodiments. As shown in FIGS. 16-17 and 25-27, the system 700 includes a syringe body 710, a needle assembly 790, a needle cover 730, a stopper member 720, a plunger member 750, a finger flange 740, and a proximal tube 742. Many of these system components (e.g., the syringe body 710, the stopper member 720, and the needle cover 730) may be off-the-shelf components to utilize the existing and relatively well-controlled supply chain, and the corresponding assembly machinery and personnel. The syringe body 710 may be glass, metal, or polymeric materials such as COC, COP, polypropylene, polyethylene, or other syringe material. The stopper member 720 may be rubber such as butyl, chlorobutyl, bromobutyl, or a polymeric material such as a thermoplastic elastomer. The stopper may be covered in a protective and/or lubricious coating such as PTFE or other polymer. The stopper member 720 being off-the-shelf refers to a commercially available stopper member, which has a generally smooth distally facing surface that contains no projections or recesses for coupling to a needle. The proximal tube 742 includes a thumb pad 744, coupled to a proximal end thereof to facilitate user application of a distally directed force to the proximal tube 742, the plunger member 750, and the stopper member 720 coupled thereto. As explained below, the system 700 may also include an injectable fluid (e.g., medications) disposed in a the syringe body 710.

As shown in FIG. 17-20C, the finger flange 740 includes a ratcheting mechanism including the proximal tube 742, which extends proximally therefrom. The ratcheting mechanism also includes a ratchet tube 760 coaxially displaced inside of the proximal tube 742 and the plunger member 750. The plunger member 750 includes a plurality of sawtooth ribs/teeth 752 disposed serially along the longitudinal axis thereof (see FIGS. 20A-20C). The ratchet tube 760 includes a plurality (e.g., four) of the elastically deformable leaves 762 operatively coupled to the sawtooth ribs 752 on the plunger member 750. In an alternative embodiment, the ratchet tube 760 may include a single elastically deformable leaf 762. The ratcheting mechanism further includes a return spring 748, which biases the ratchet tube 760 in a proximal position in which a flange 766 on a proximal end of the ratchet tube 760 is spaced apart from a proximal end of the proximal tube 742 (see FIG. 17).

The leaves 762 interferes with the ribs/teeth 752 on the plunger member 750, which allows the ratchet tube 760 to move proximally, but not distally, relative to the plunger member 750. In the distal direction, the ratchet tube 760 can apply the force to the plunger member 750. When the return spring 748 moves the ratchet tube 760 proximally, the leaves 762 flex radially inward to allow the ratchet tube 760 to move proximally over the plunger member 750. The system 700 is configured such that moving the ratchet tube 760 from a distal position to a proximal position moves the leaves 762 thereof from one rib/tooth 752 to the next rib/tooth 752 in a proximal direction. This moves the plunger member 750 distally by a distance of one rib/tooth 752. The various components of the system 500 can be configured such that moving the plunger member 750 distally by a distance of one rib/tooth 752 ejects a predetermined volume (e.g., 0.1 ml, microdose) of fluid from an interior of the syringe body 710. Consequently, a user can serially advance the plunger member 750 in the syringe body 710 and eject a predetermined volume of fluid by alternately depressing and releasing the thumb pad 744.

Figure 18:
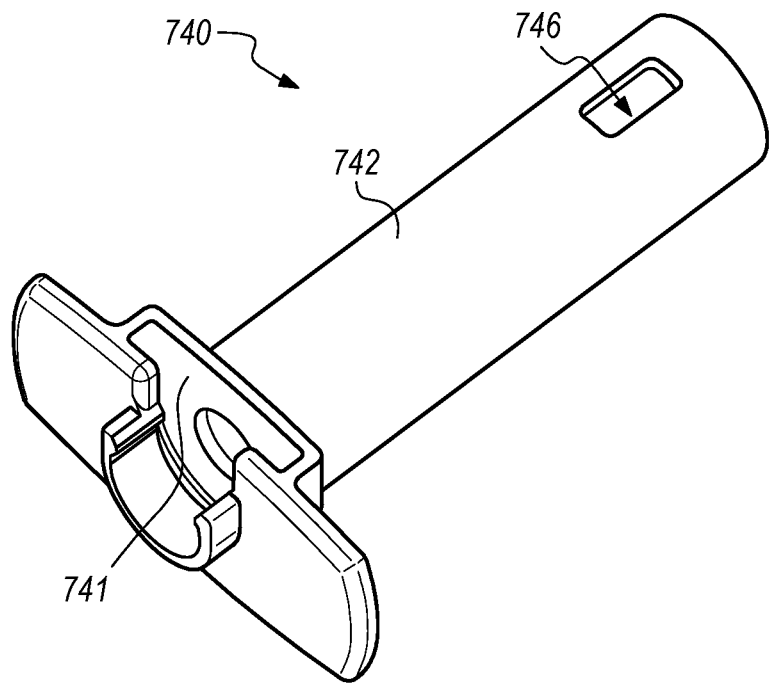

FIG. 18 depicts a finger flange 740 for use with the multiple site injection system 700. The proximal tube 742 aligns the ratchet tube 760 and the plunger member 750 of the ratcheting mechanism. The proximal tube 742 also has a proximal end 741, which provides a hard stop against the flange 766 on the proximal end of the ratchet tube 760. The distance between the proximal end of the proximal tube 742 and the flange 766 on the proximal end of the ratchet tube 760 defines the travel of the plunger member 750 per injection. The proximal tube 742 also includes a plurality (e.g., two) of windows 746 configured to interfere with anti-pullout tabs 768 on the ratchet tube 760.

Figure 19:
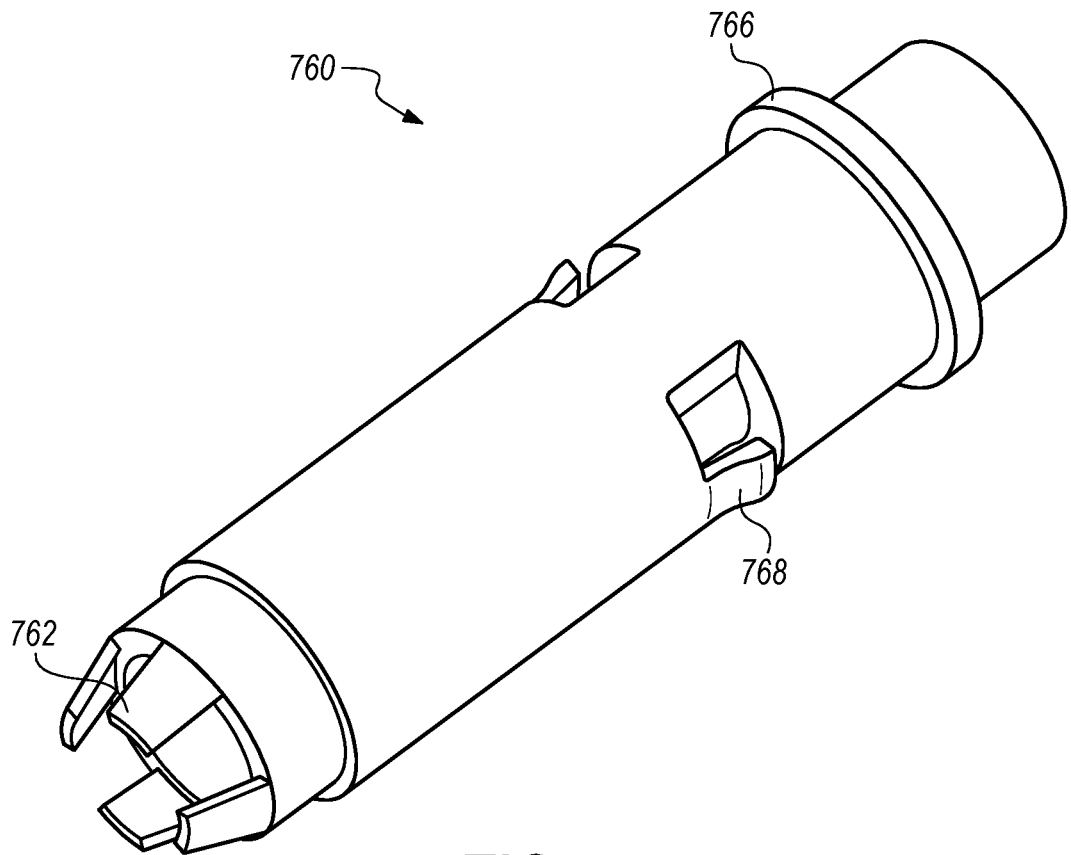

FIG. 19 depicts a ratchet tube 760 for use with the multiple site injection system 700. The ratchet tube 760 includes a plurality (e.g., four) of elastic leaves 762 configured to interfere with the ribs/teeth 752 on the plunger member 750. In an alternative embodiment, the ratchet tube 760 may include a single elastically deformable leaf 762. The ratchet tube 760 also includes a plurality (e.g., two) of anti-pullout tabs 768 configured to extend to interfere with the windows 746 and the proximal tube 742. In an alternative embodiment the ratchet tube 760 may include a single anti-pullout tab 768. The ratchet tube 760 further includes a flange 766 configured to interfere with the proximal end of the proximal tube 742 to define a single injection stroke.

Figure 20A:
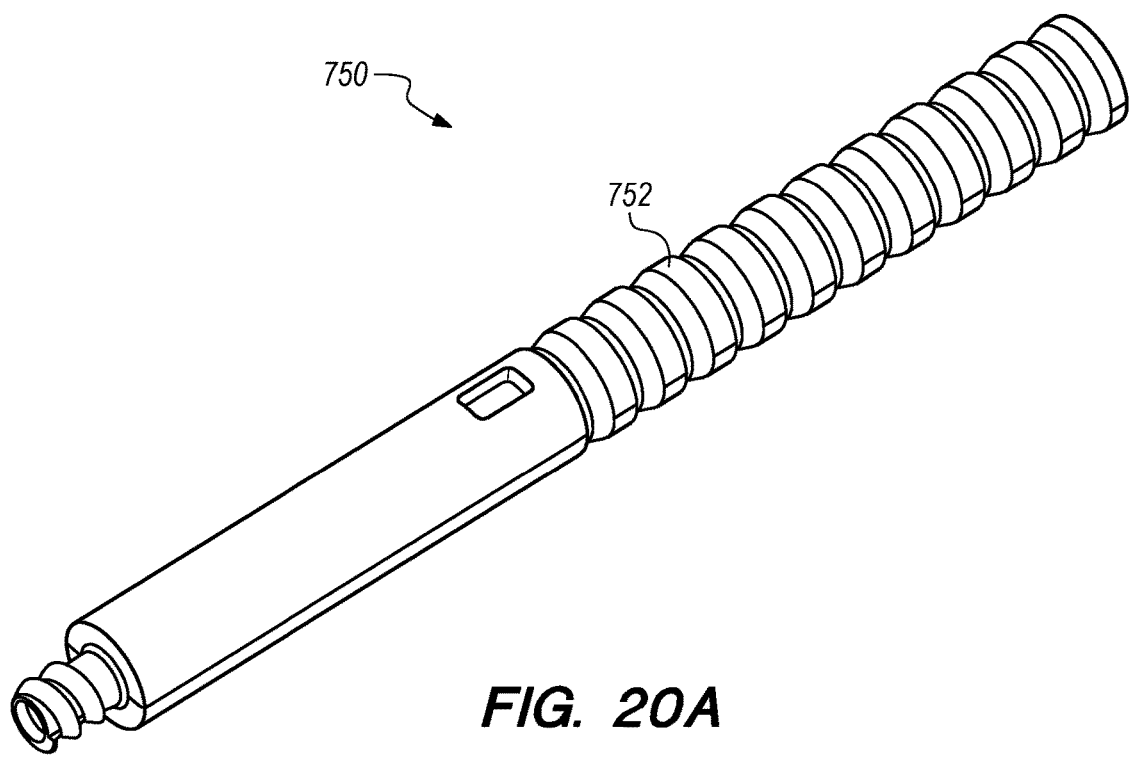
Figure 20B:
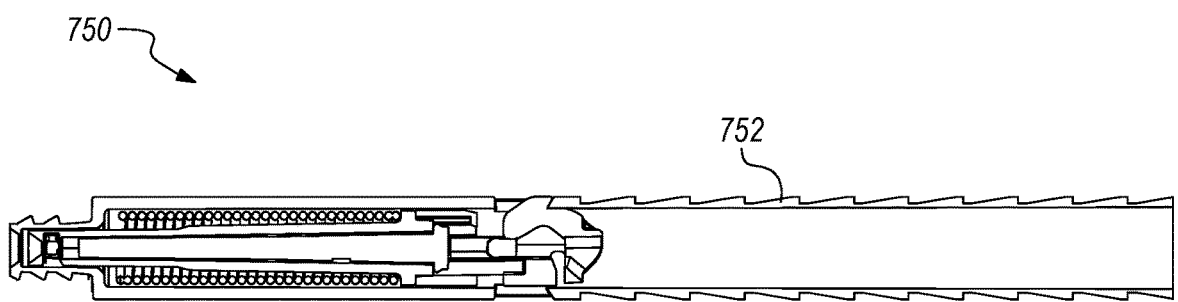
Figure 20C:
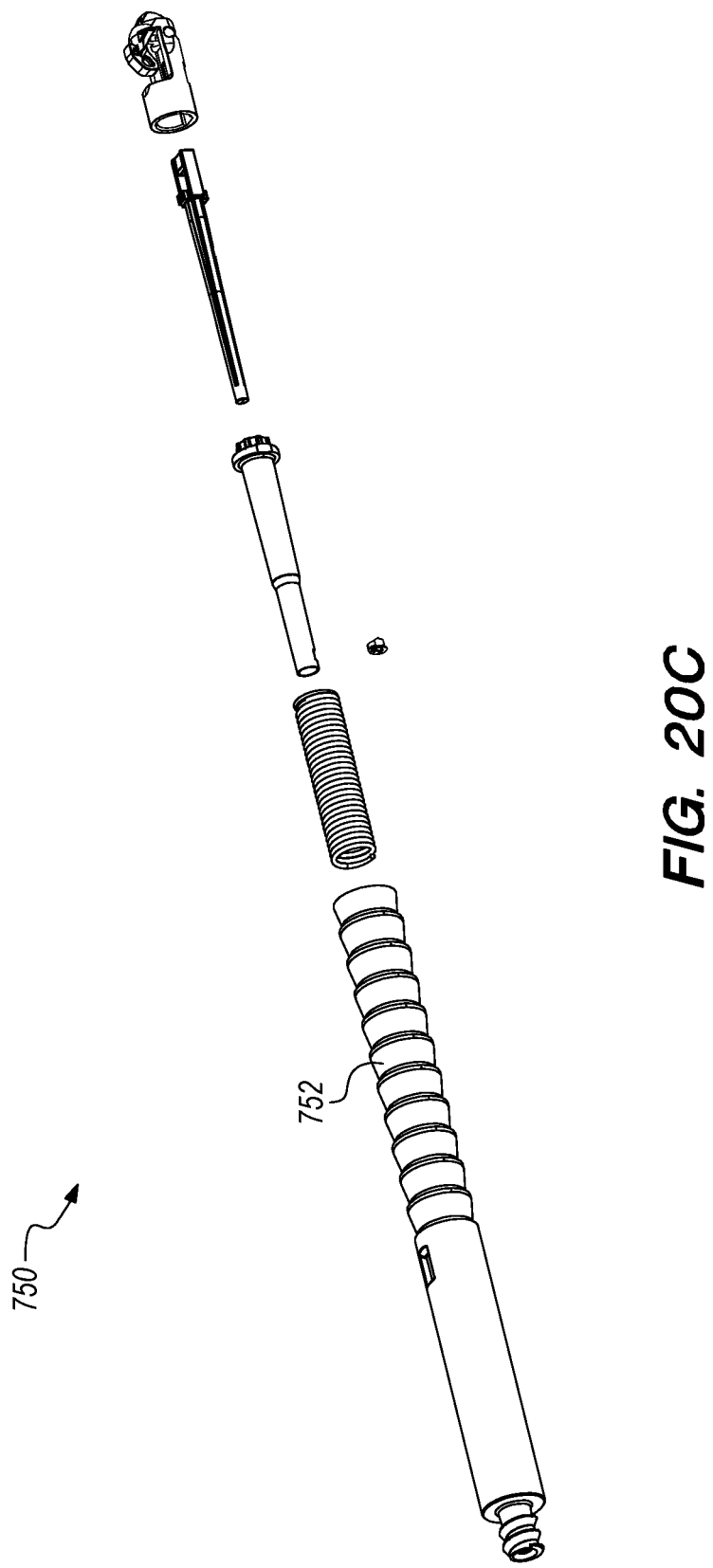

FIGS. 20A-20C depicts a plunger member 750 for use with the multiple site injection system 700. The plunger member 750 includes a pattern of serial sawtooth ribs/teeth 752 on external surfaces thereof. The spacing between the ribs/teeth 752 can be modified to adjust the dosage delivered by the multiple site injection system 700. The spacing between ribs/teeth 752 may be constant along the length of the plunger member 750 to deliver constant doses per injection or may be variable along the length of the plunger member 750 to deliver different doses per injection. The plunger member 750 also includes a needle retraction mechanism similar to the ones depicted and described in co-owned U.S. patent application Ser. Nos. 14/696,342, 14/543,787, 14/321,706, 62/416,102, 62/431,382, 62/480,276, 62/508,508, 62/542,230, 15/801,239, 15/801,259, 15/801,281, 15/801,304, the contents of which were previously fully incorporated herein by reference as though set forth in full.

Figure 21:
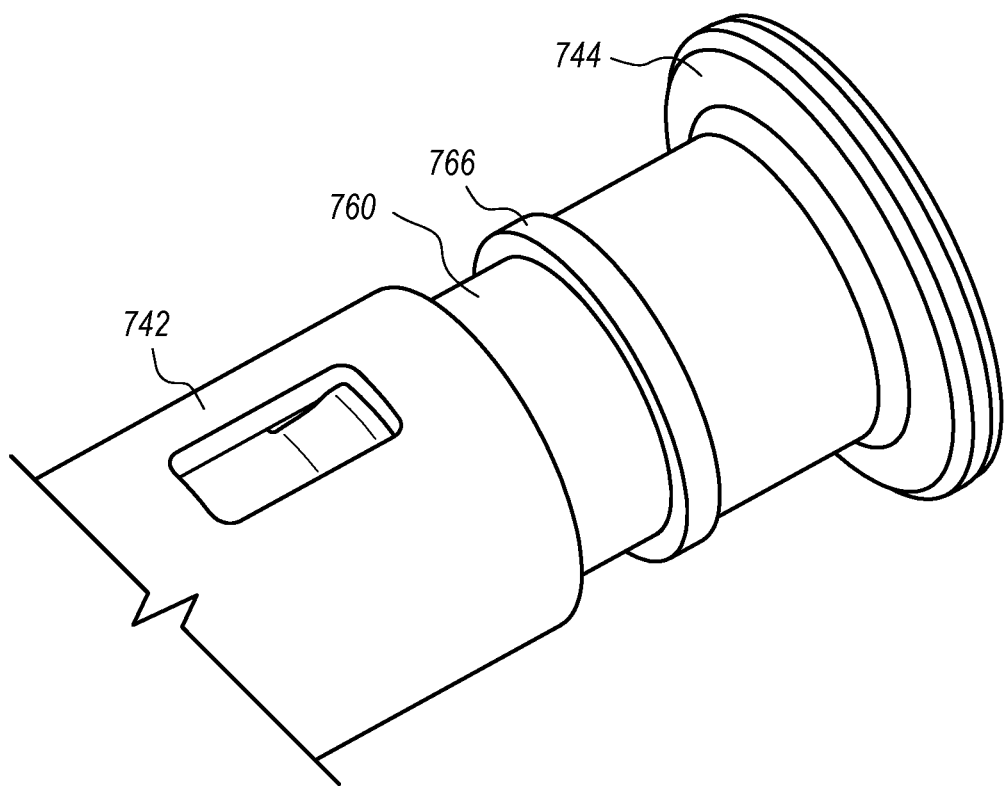
Figure 22:
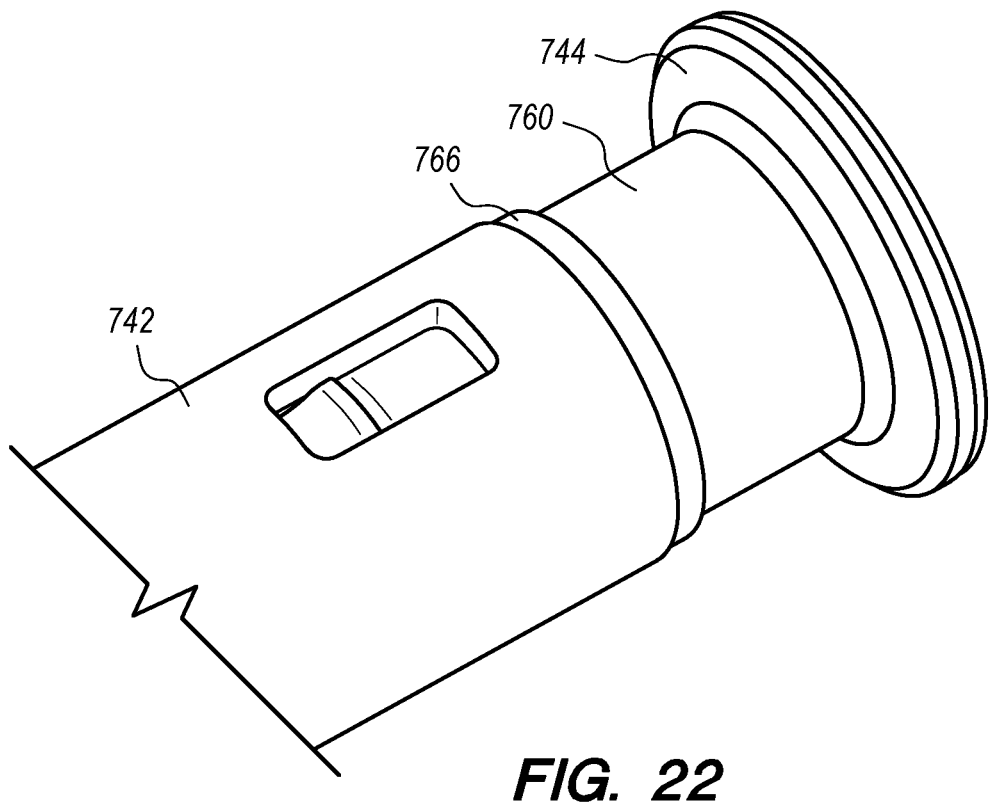

FIGS. 21 and 22 depict the proximal and distal positions of the ratchet tube 760 relative to the proximal tube 742 of the finger flange 740. In the proximal position depicted in FIG. 21, the return spring 748 pushes the ratchet tube 760 proximally until the anti-pullout tabs 768 on the ratchet tube 760 interfere with the windows 746 in the proximal tube 742. In the distal position depicted in FIG. 22, a user applies a distally directed force to the thumb pad 744 pushing the ratchet tube 760 distally until the flange 766 on the ratchet tube 760 interferes with the proximal end of the proximal tube 742. This mechanism defines the stroke length of the dose injection, thereby reducing overdose situations.

Figure 23A:
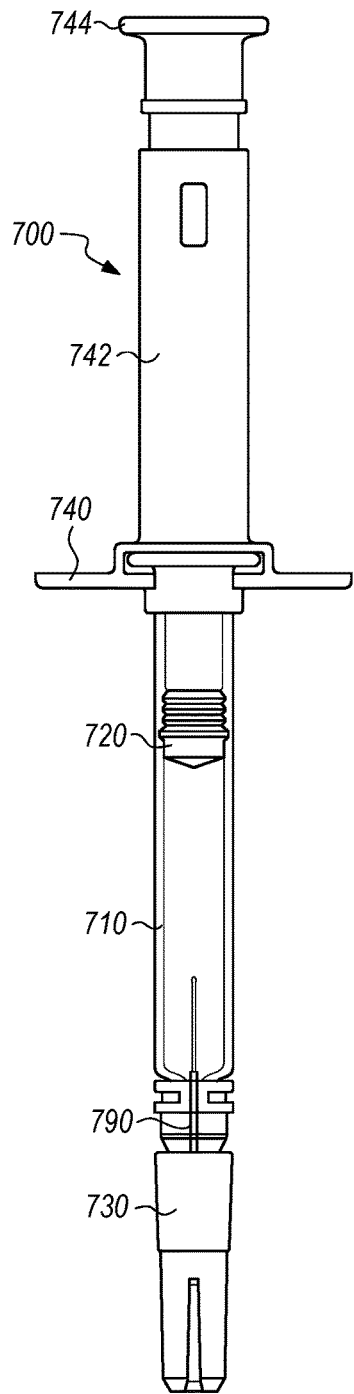
Figure 23B:
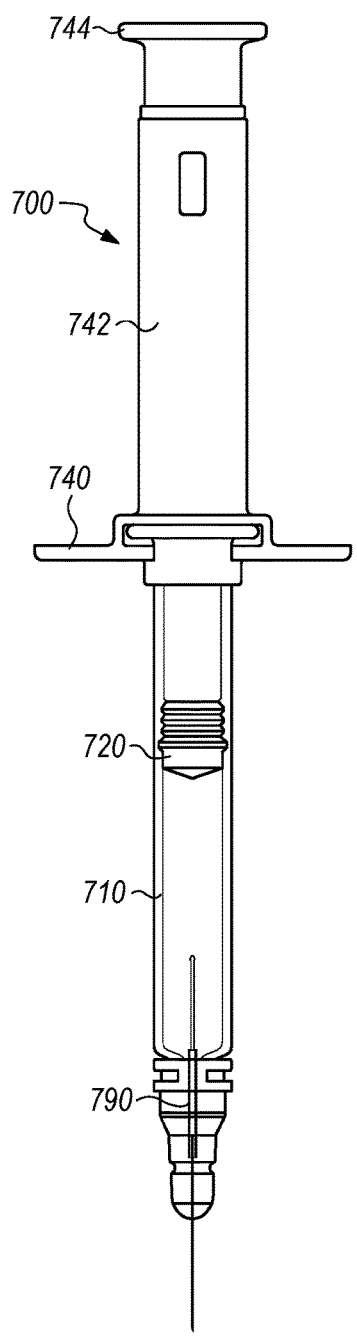
Figure 23C:
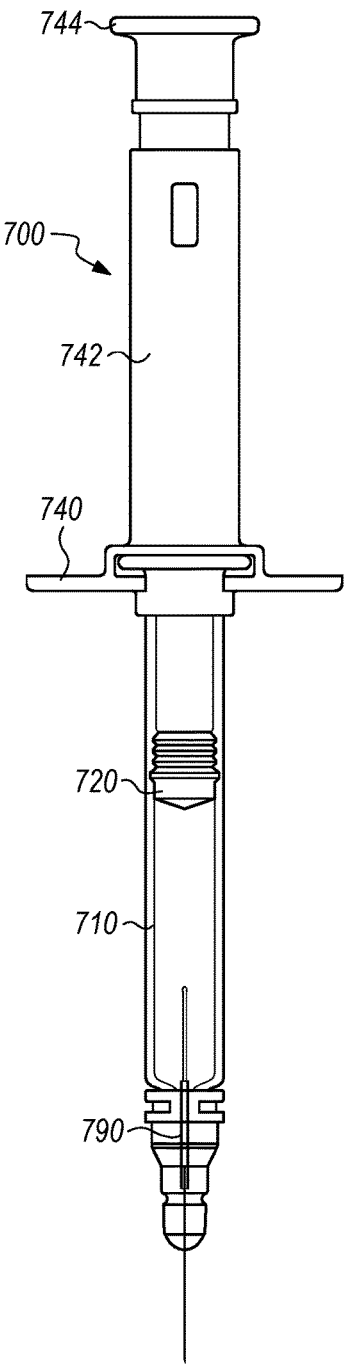
Figure 24A:
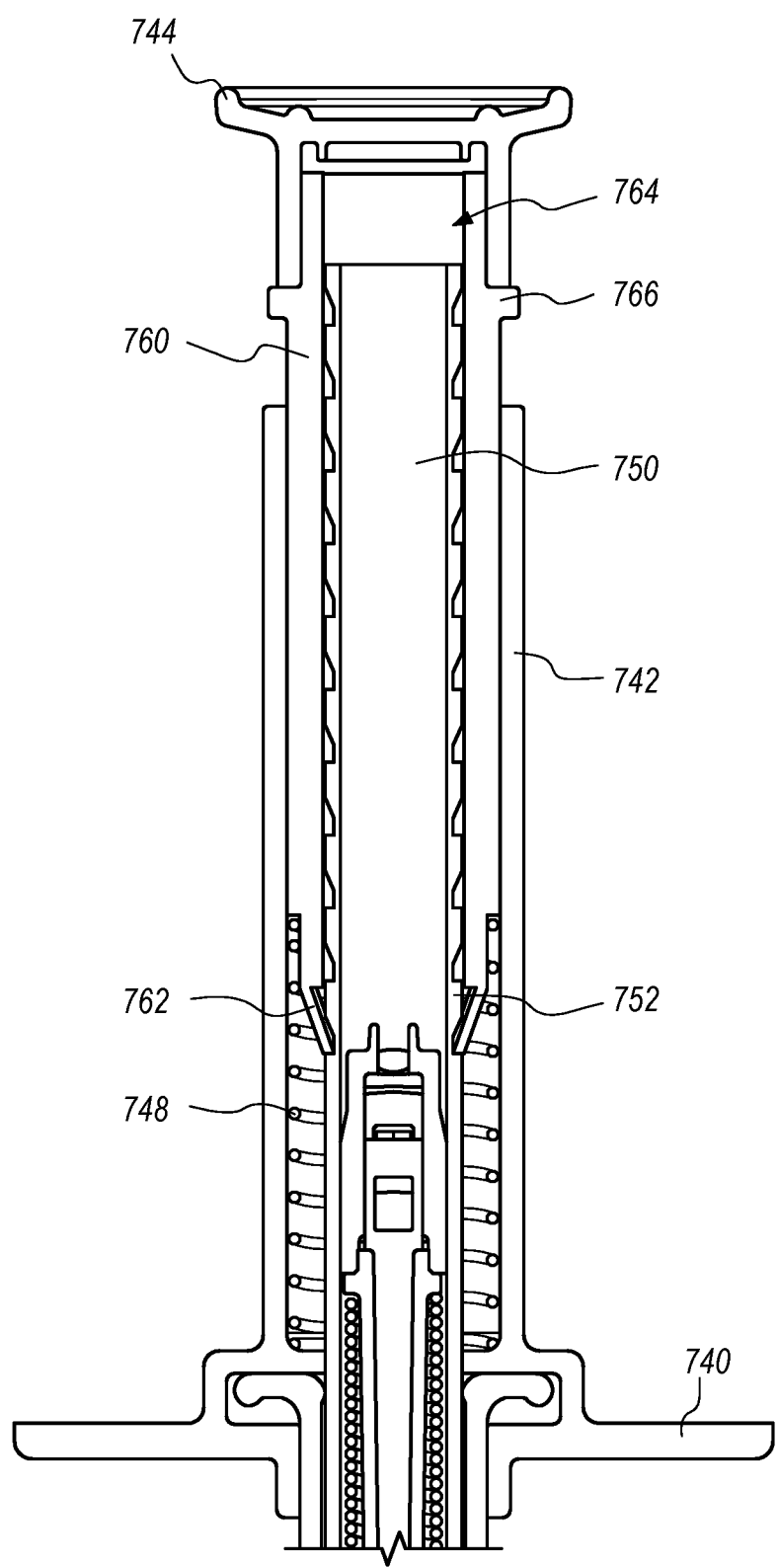

FIGS. 23A-C and 24A-C depict a single injection cycle using the multiple site injection system 700. In FIGS. 23A and 24A, the system 700 is ready for its first injection with the leaves 762 on the ratchet tube 760 engaged in the first sawtooth ribs/teeth 752 on the plunger member 750. As the user depresses the thumb pad 744, the leaves 762 transmits the distally directed force to the ribs/teeth 752, thereby advancing the plunger member 750 and the stopper member 720 coupled thereto by the distance of approximately one rib/tooth 752. Advancement of the stopper member 720 ejects a fixed volume (e.g., 0.1 ml, microdose) of fluid from an interior of the syringe body 710.

Figure 24B:
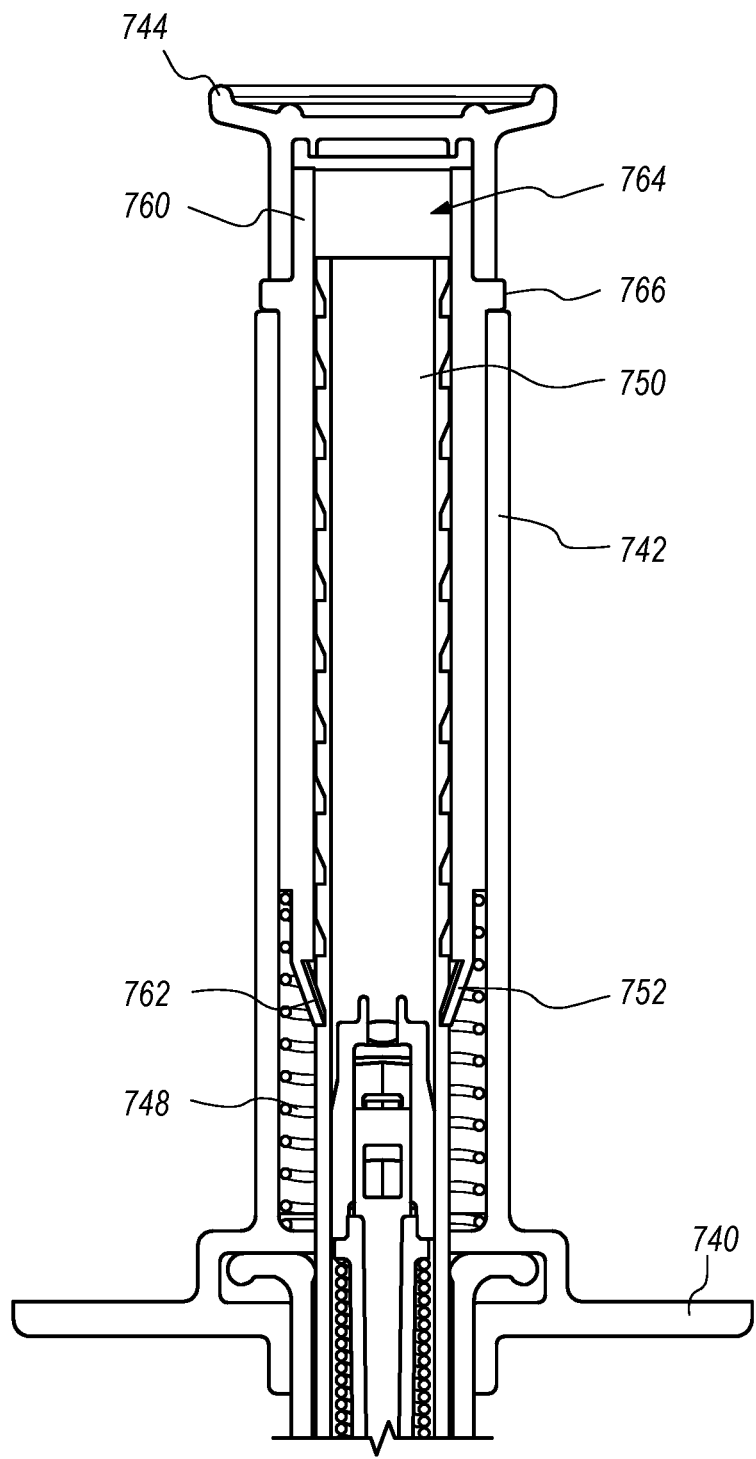

In FIGS. 23B and 24B, the user has depressed the thumb pad 744 as described above. Advancing the ratchet tube 760 also compresses the return spring 748. The interference between the flange 766 on the ratchet tube 760 and the proximal end of the proximal tube 742 defines to stroke length and reduces overdose situations. The ratchet tube 760 also includes a space 764 at a proximal end thereof to accommodate the proximal end of the plunger member 750 at the bottom of the first stroke.

Figure 24C:
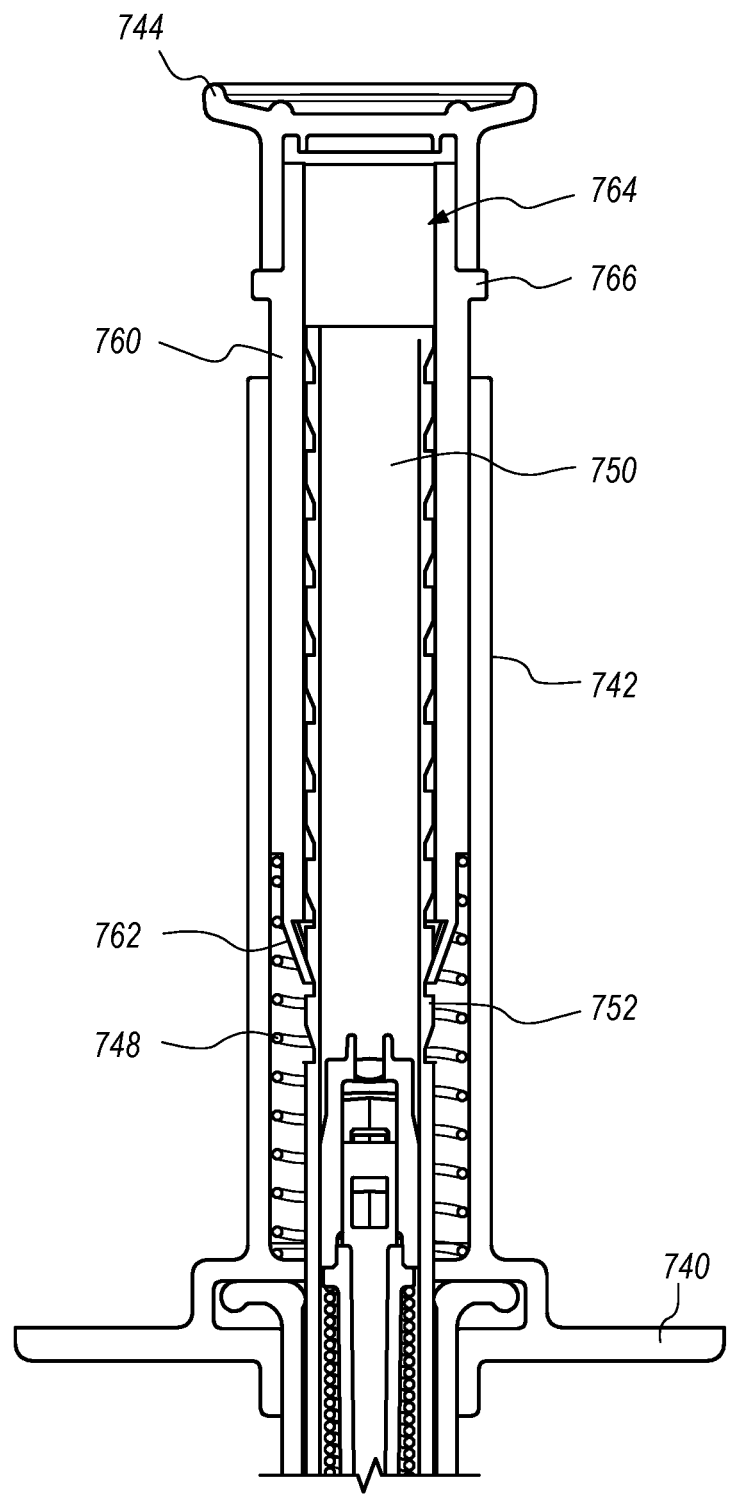
Figure 25:
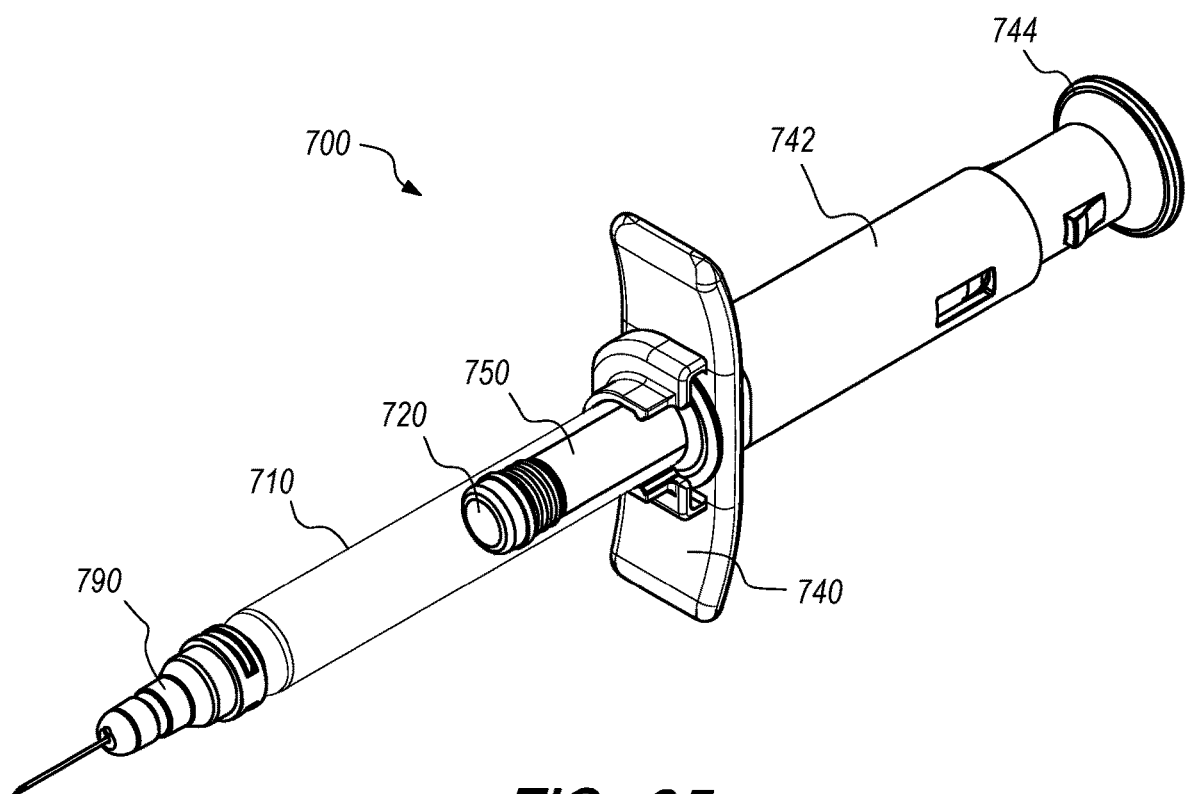
Figure 26:
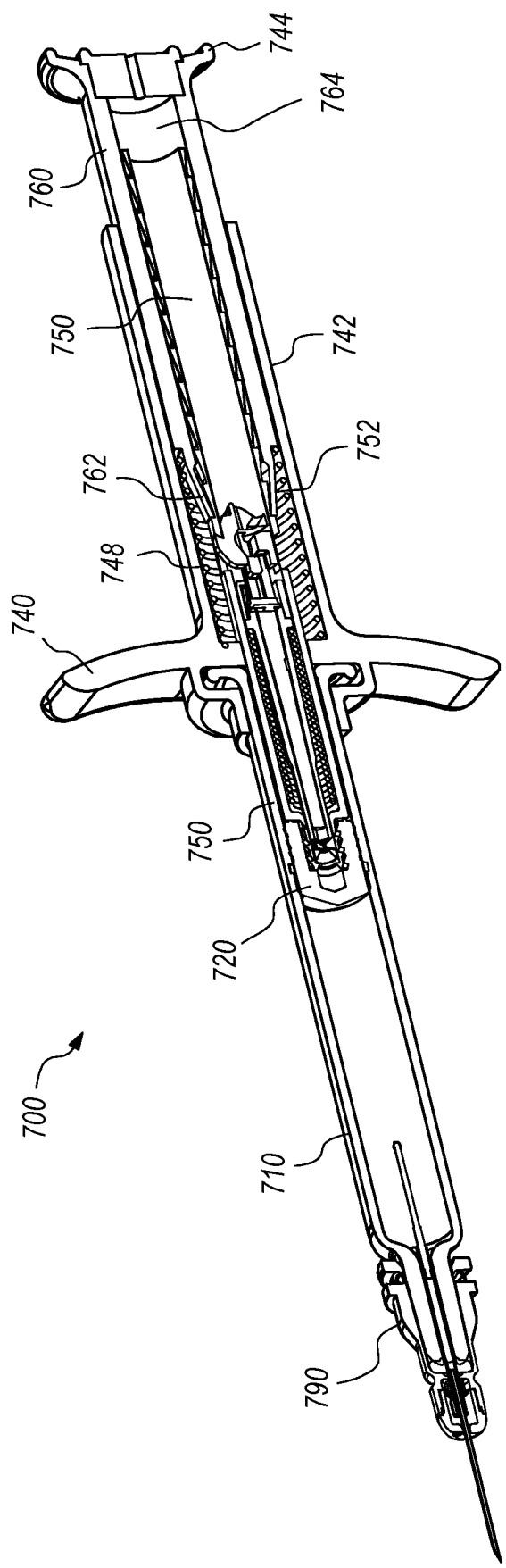

In FIGS. 23C and 24C, the user has released the thumb pad 744. The return spring 748 expands and moves the ratchet tube 760 proximally over the plunger member 750 which is held in place by friction between the stopper member 720 and the syringe body 710. As the tube 760 moves proximally, the elastically deformable leaves 762 glide over the sawtooth geometry of the ribs/teeth 752 and moves from the first rib/tooth 752 to the next proximal rib/tooth 752. Accordingly, the ratchet tube 760 and the thumb pad 744 returned to a ready position for the next injection while the plunger member 750 remains in position having advanced by a distance of one rib/tooth 752.

The injection process shown in FIGS. 23A-24C can be repeated to give a series of injections having a fixed volume (e.g., 0.1 ml, microdose) until the plunger member 750 has moved distally until the proximal most rib/tooth 752 has move distally past and is no longer engaged with the leaves 762 of the ratchet rube 760. As shown in FIGS. 17 and 23A-24C, after the multiple site injection system 700 has delivered its last dose injection, the needle 792 in the needle assembly 790 may be retracted proximally completely through the stopper member 720 and at least partially into the plunger member 750 so that the sharp end of the needle 792 is no longer exposed to minimize unintended needle punctures. Such needle retraction systems are shown in co-owned U.S. patent application Ser. Nos. 14/696,342, 14/543,787, 14/321,706, 62/416,102, 62/431,382, 62/480, 276, 62/508,508, 62/542,230, 15/801,239, 15/801,259, 15/801,281, 15/801,304, the contents of which were previously fully incorporated herein by reference as though set forth in full.

Figure 27:
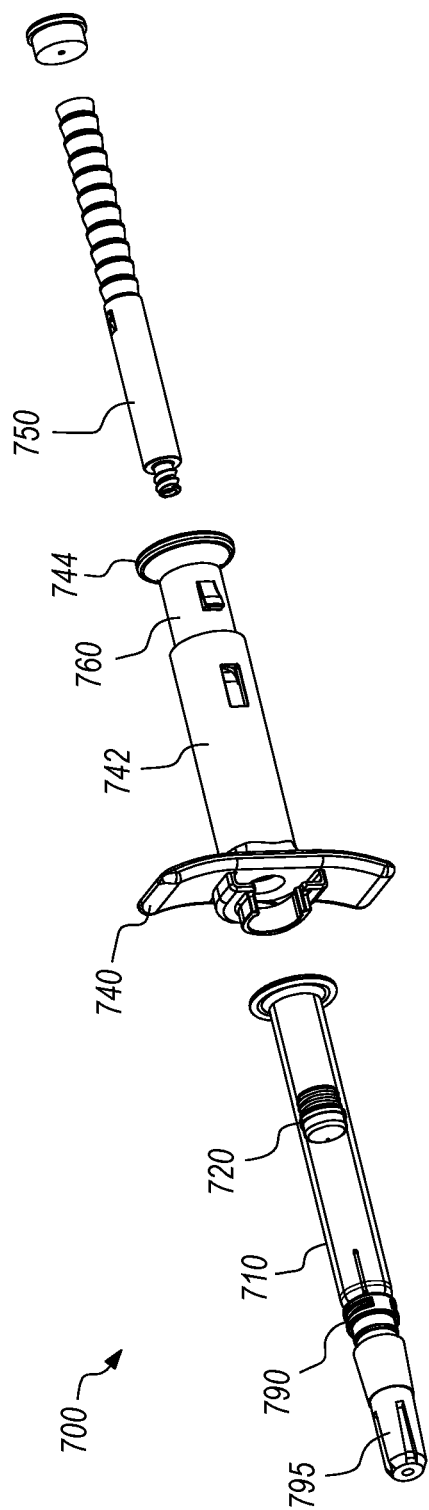

FIG. 27 depicts the assembly of the multiple site injection system 700 according to some embodiments. The syringe body 710 is coupled to a needle assembly (not shown; see 790 in FIG. 26) and capped with a needle shield 795 at a distal end thereof. The syringe body 710 is pre-filled with an injectable fluid (e.g., medicine) and pre-loaded with a stopper member 720. The finger flange 740 can then be coupled with (e.g., snapped onto) the syringe flange of the syringe body 710. Next, the plunger member 750 is inserted through a proximal opening in the ratchet tube 760 and coupled with (e.g., screwed into) the stopper member 720. Optionally, the proximal opening in the ratchet tube 760 can be sealed, resulting in an assembled multiple site injection system 700.

Figure 28:
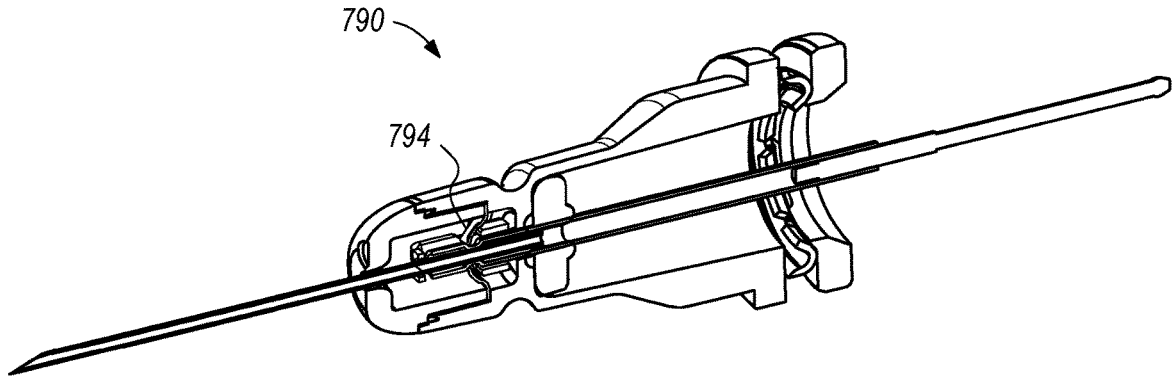
Figure 29:
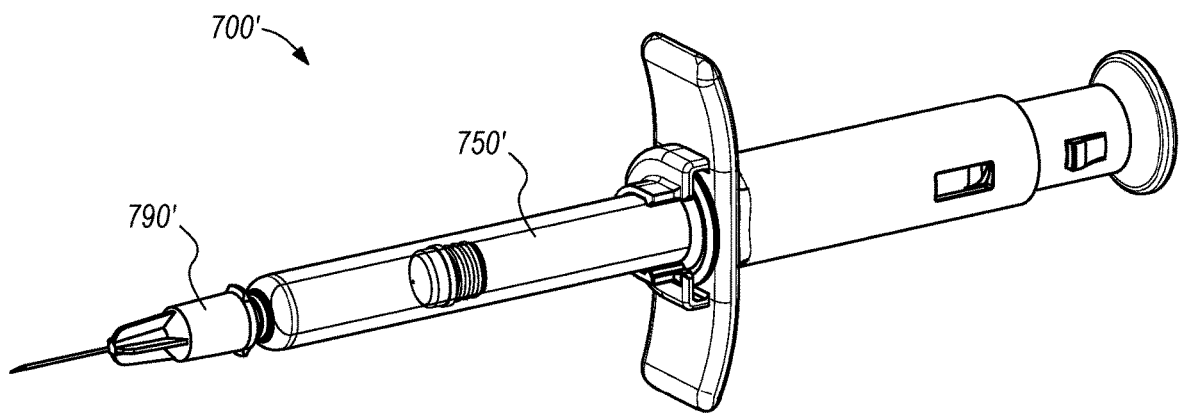
FIGS. 29-36 illustrate various aspects of a multiple site injection system and a multiple site injection method according to some embodiments.

FIG. 28 depicts a needle assembly 790 for use with the multiple site injection system 700 according to some embodiments. The needle assembly 790 includes a needle latch 792, such as the ones described in co-owned U.S. patent application Ser. Nos. 14/696,342, 14/543,787, 14/321,706, 62/416,102, 62/431,382, 62/480,276, 62/508, 508, 62/542,230, 15/801,239, 15/801,259, 15/801,281, 15/801,304, the contents of which were previously fully incorporated herein by reference as though set forth in full. The needle latch assembly 790 also includes a retaining ring 794, such as the ones described in co-owned U.S. patent application Ser. No. 62/827,767, the contents of which are fully incorporated herein by reference as though set forth in full.

Figure 30:
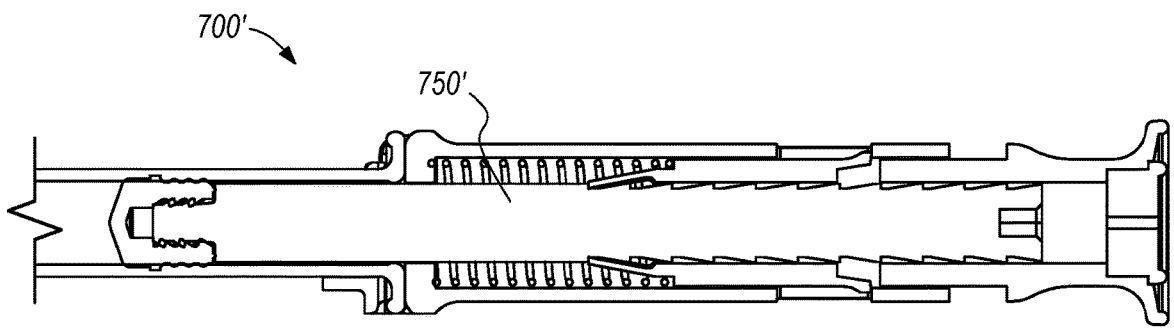
Figure 31:
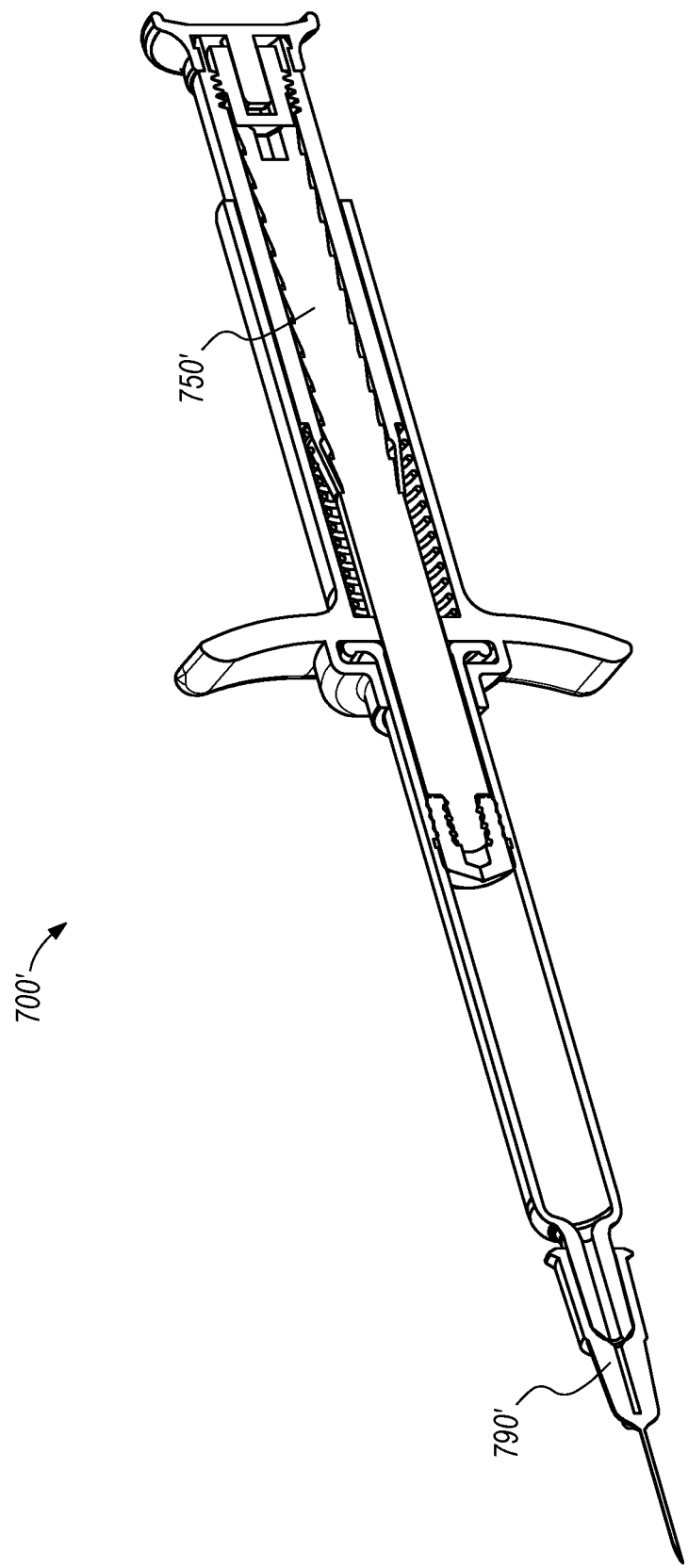

FIGS. 29-36 depict a multiple site injection system 700' according to some embodiments. The system 700' depicted in FIGS. 29-36 is similar to the system 700 depicted in FIGS. 16-28, and identical components are described above. The difference between the system 700' depicted in FIGS. 29-36 and the system 700 depicted in FIGS. 16-28 is that the system 700' depicted in FIGS. 29-36 includes a staked needle assembly 790' that is not retractable. As such, the plunger member 750' does not include needle retraction components. As shown in FIGS. 30 and 31, the plunger member 750' may be a solid body (e.g., polymer).

Figure 32:
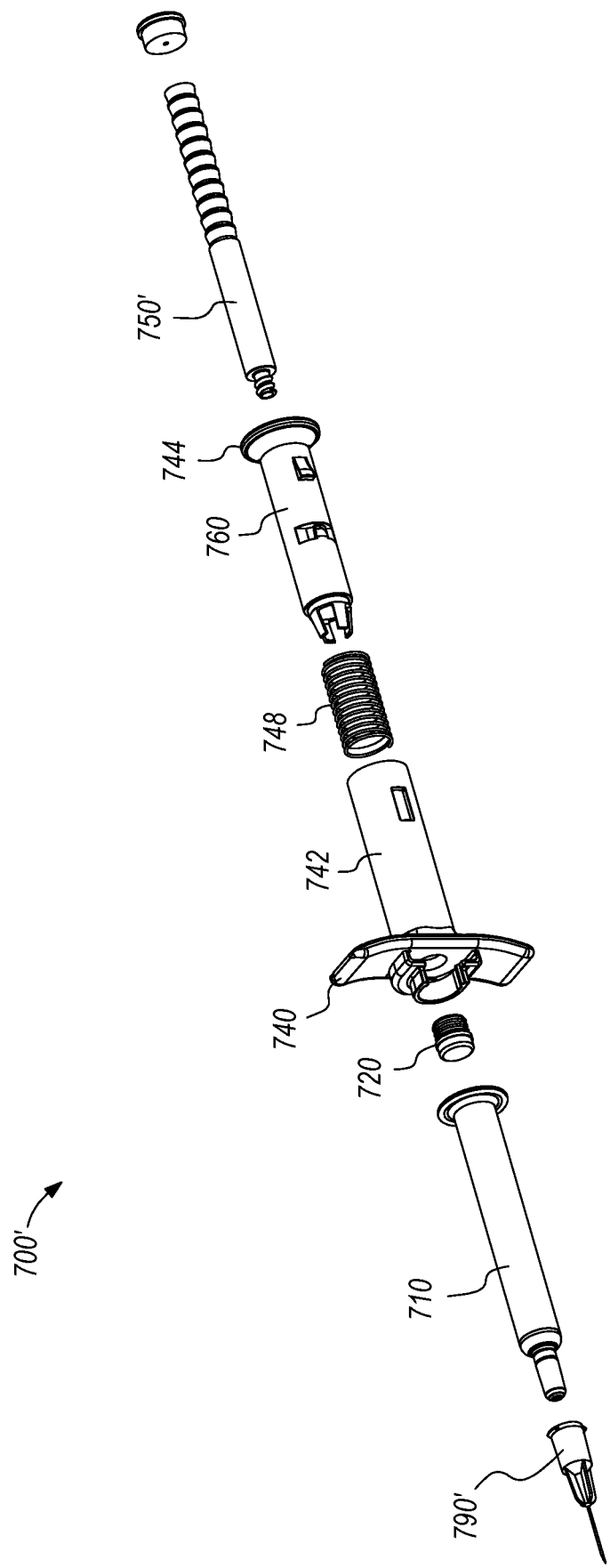
Figure 33:
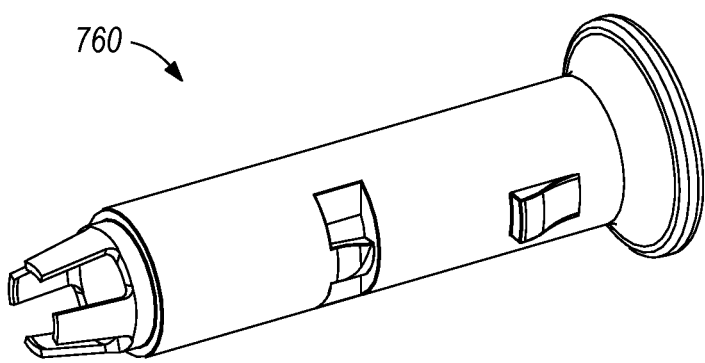
Figure 34:
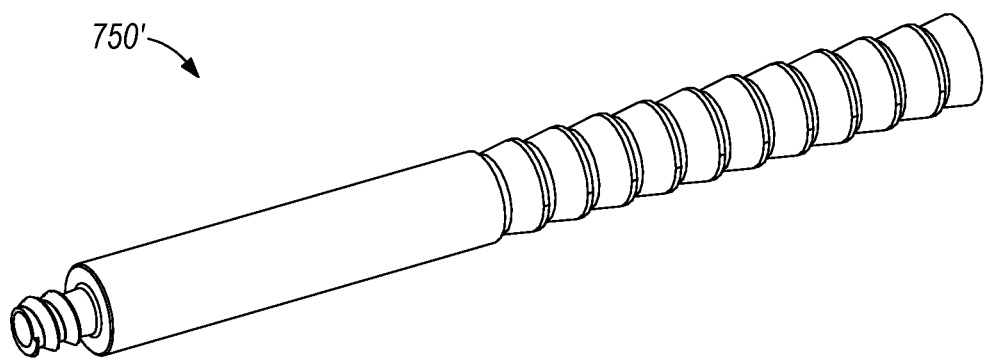

FIG. 32 depicts the system 700' in an exploded view with components identical to those in the system 700 depicted in FIGS. 16-28 labeled with the same reference numerals. FIG. 33 depicts the ratchet tube 760, which is identical to the ratchet tube 760 in the system 700 depicted in FIGS. 16-28. FIG. 34 depicts the solid plunger member 750'.

Figure 35:
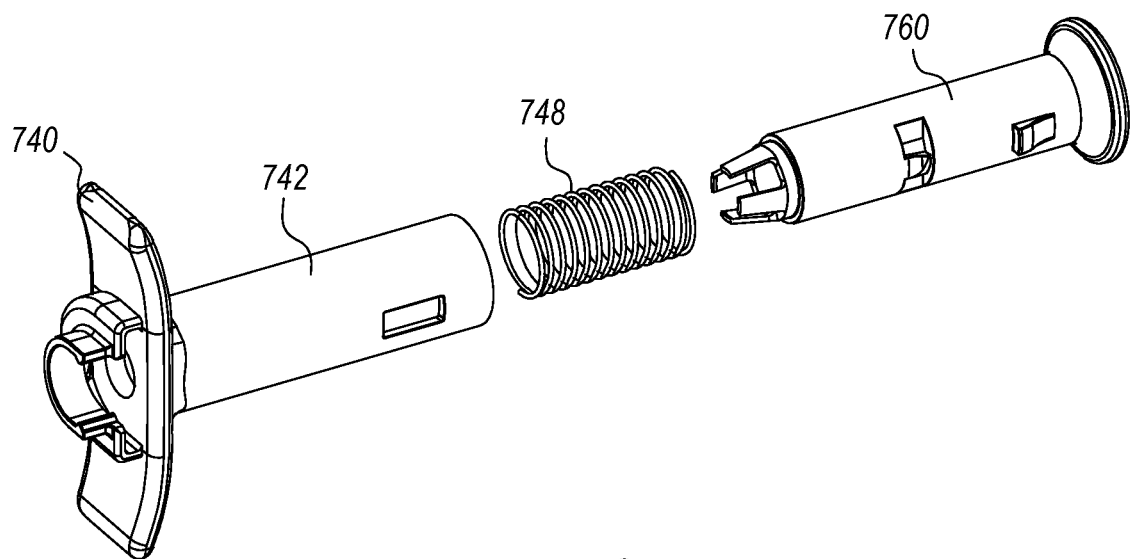
Figure 36:
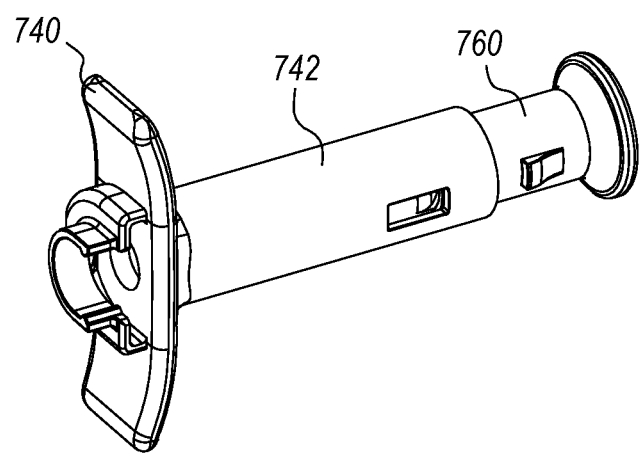

FIGS. 35 and 36 depict partial assembly of a finger flange 740/ratchet tube 760 unit according to some embodiments. A return spring 748 is first inserted the proximal tube 742 of the finger flange 740. Then the ratchet tube 760 is inserted into the proximal tube 742 of the finger flange 740. The finger flange 740/ratchet tube 760 unit can then be mounted onto the glass/syringe flange of a syringe body and the plunger member 750' can then be inserted through the ratchet tube 760 and coupled to a stopper member in the syringe body. Optionally, the proximal end of the ratchet tube 760 can be closed/sealed.

Figure 37:
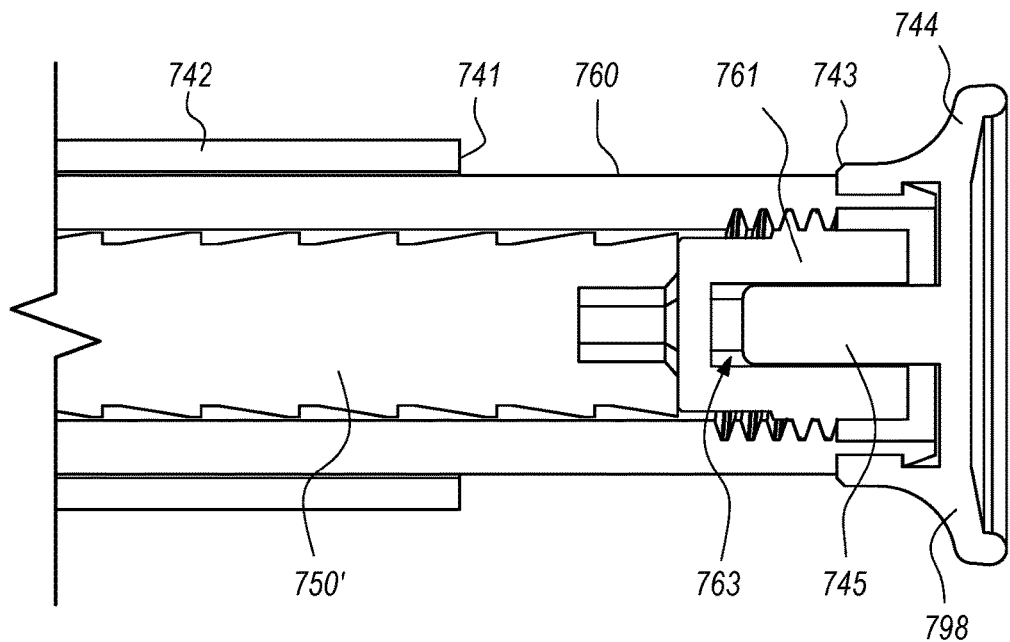
FIGS. 37-42B illustrate various aspects of a multiple site injection system and a multiple site injection method according to some embodiments.
Figure 38:
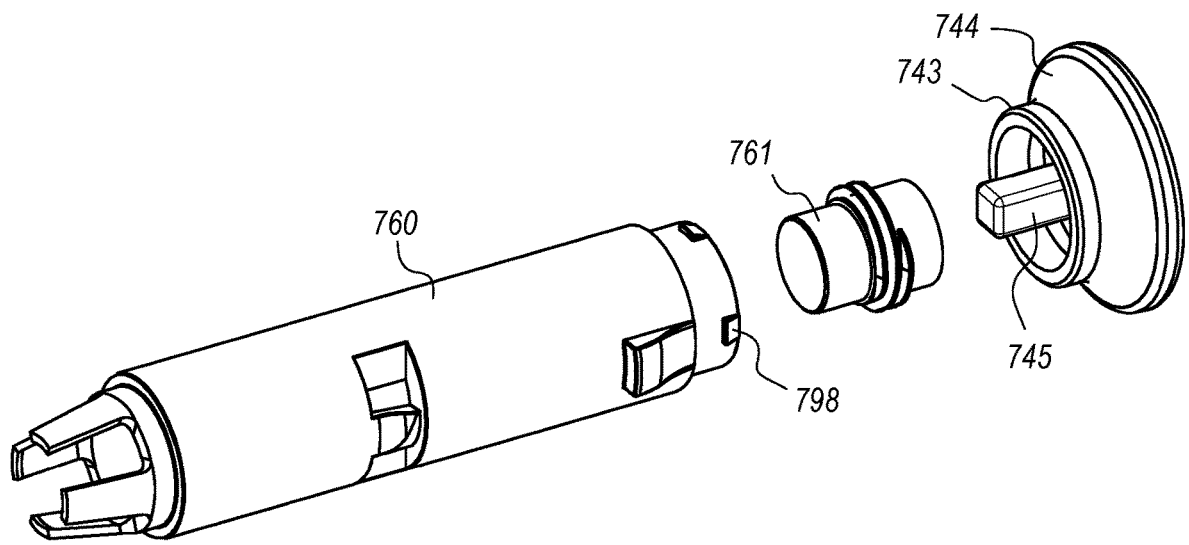
Figure 39:
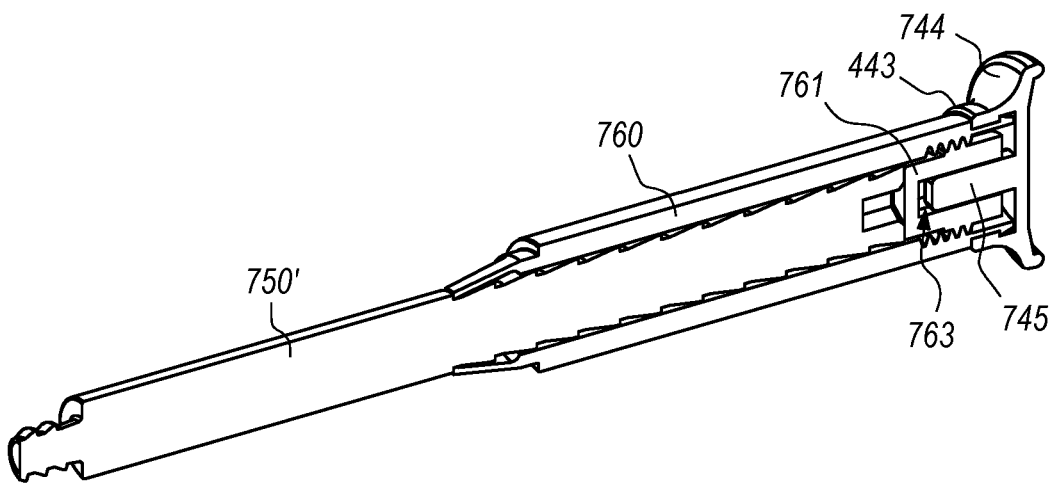
Figure 40:
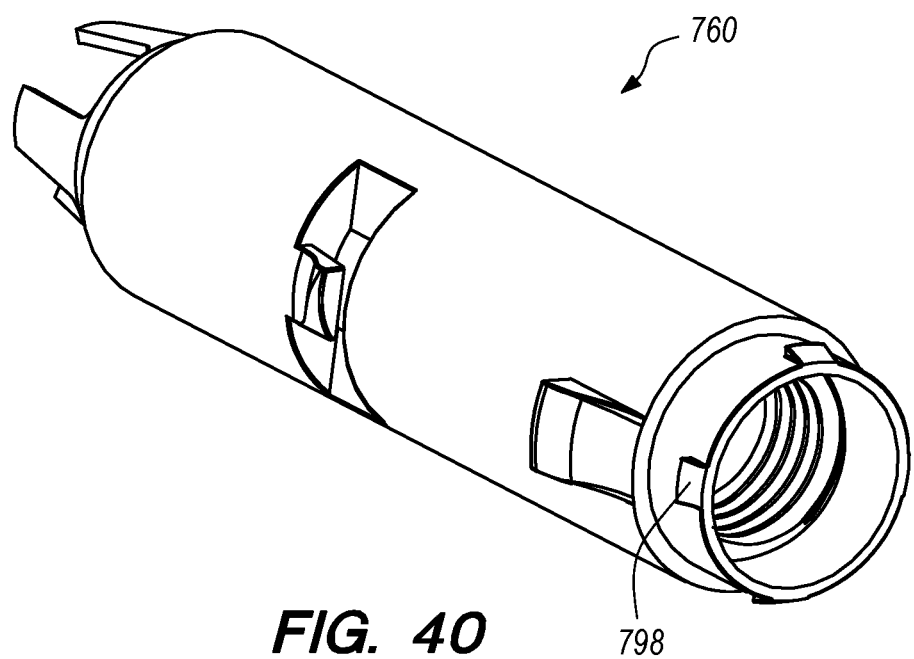
Figure 41A:
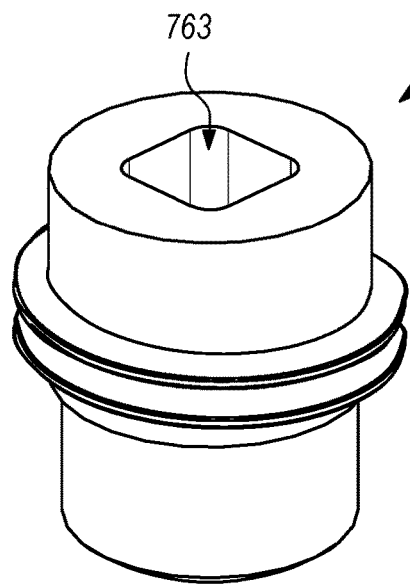
Figure 41B:
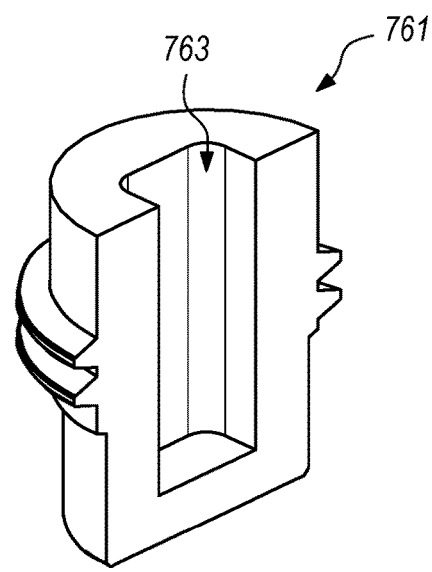
Figure 42A:
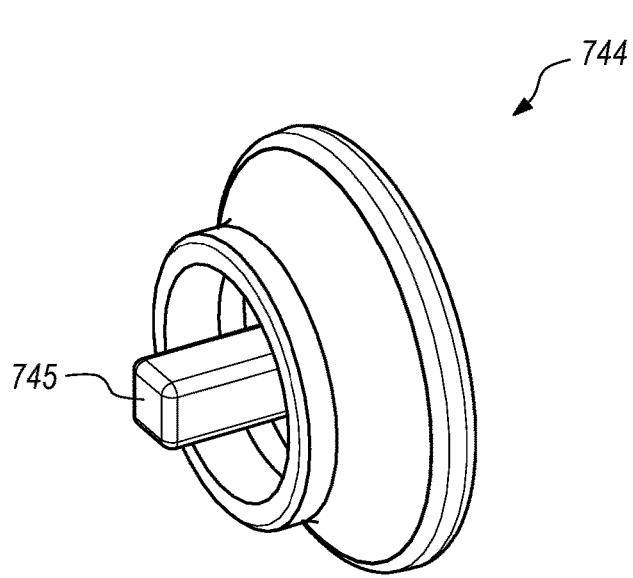
Figure 42B:
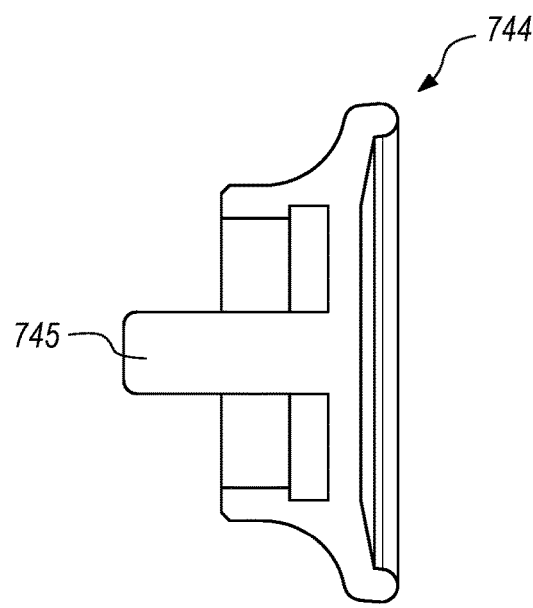
Figure 43:
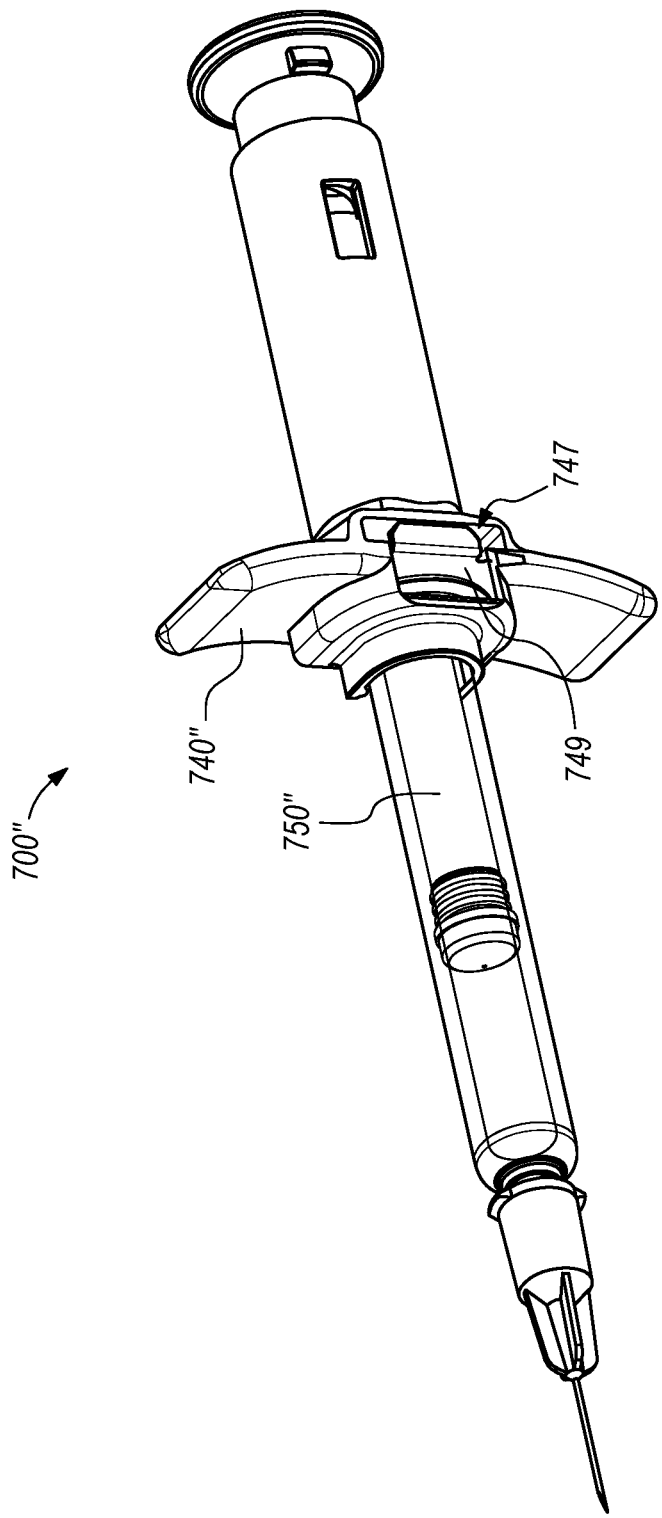
FIGS. 43-47C illustrate various aspects of a multiple site injection system and a multiple site injection method according to some embodiments.
Figure 44:
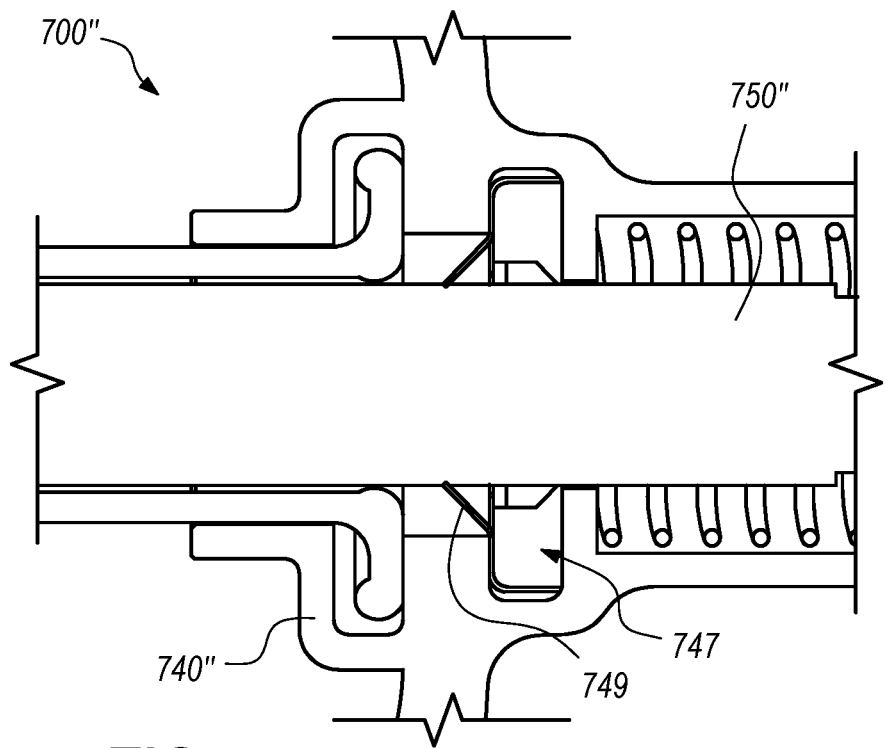
Figure 45:
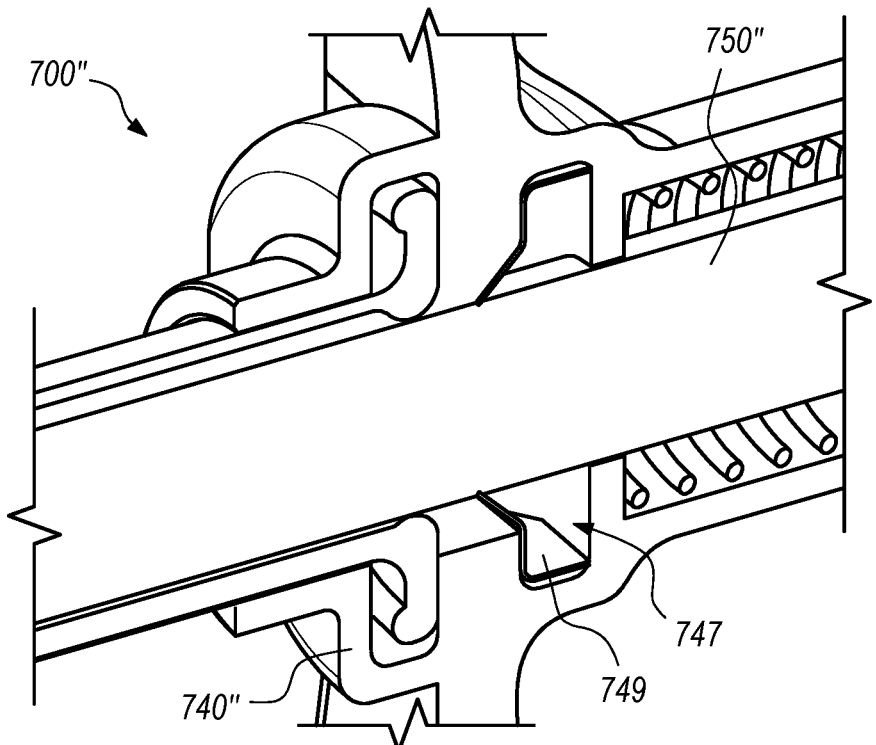
Figure 46:
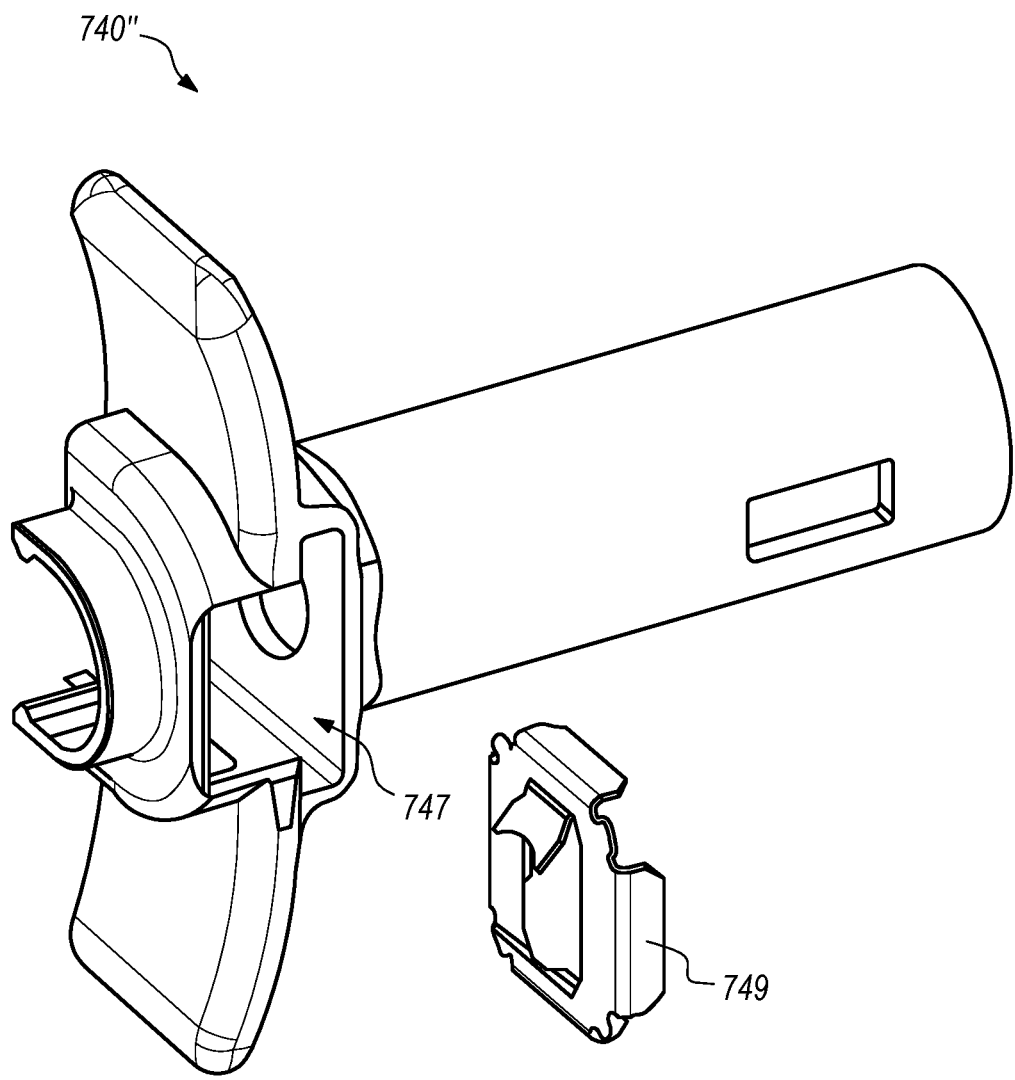

FIGS. 37-42B depict some components for removing air from a syringe body ("de-bubbling" or "priming") and moving some of the injectable fluid into the needle by controllably advancing a plunger member 750' of a multiple site injection system 700' according to some embodiments. This process ("priming") is especially useful for microdose multi-site injection systems. As shown in FIGS. 37-39 and 41A-41B, the system 700' includes a priming screw 761, which is coupled to the ratchet tube 760 by a threaded connection, which translates rotation of the priming screw 761 to distal movement thereof. The priming screw 761 rests against a proximal end of the plunger member 750' such that distal movement of the priming screw 761 moves the plunger member 750' distally. The sealing priming screw 761 defines a rectangular drive recess 763 (FIGS. 41A-41B). The thumb pad 744 includes a rectangular drive boss 745 (FIGS. 42A-42B), which is configured to fit in and interfere with the rectangular drive recess 763 to rotate the sealing member 761 to advance the priming screw 761 distally to drive the plunger member 750' and coupled stopper member distally to expel air and fluid from the needle of the system 700'. As shown in FIGS. 37, 38, and 40, the ratchet tube 760 includes a plurality (e.g. four) of latches 798 configured to couple the thumb pad 744 to the ratchet tube 760.

Figure 47A:
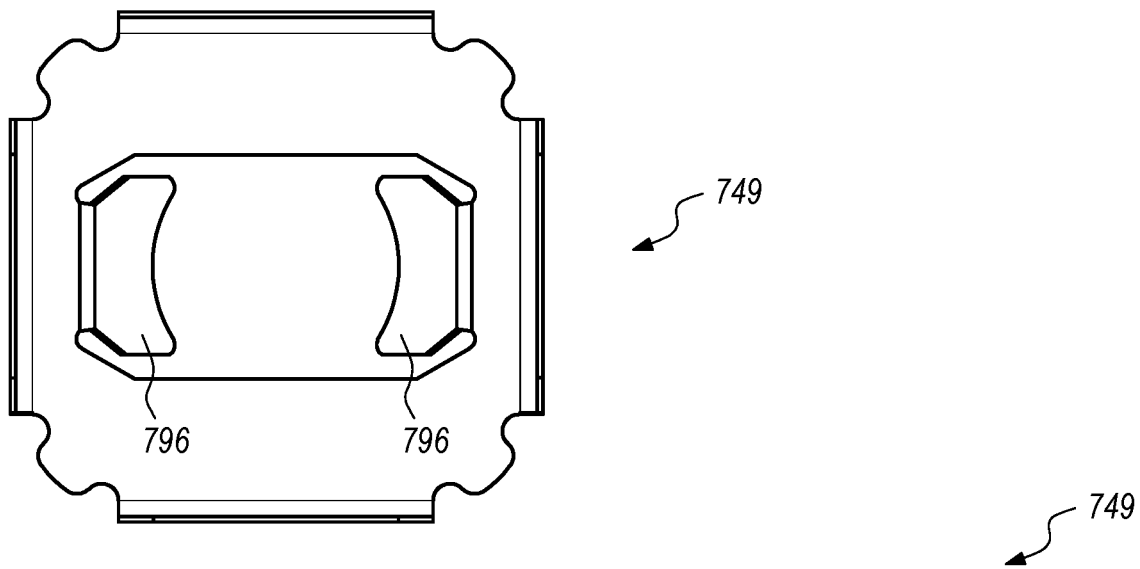
Figure 47B:
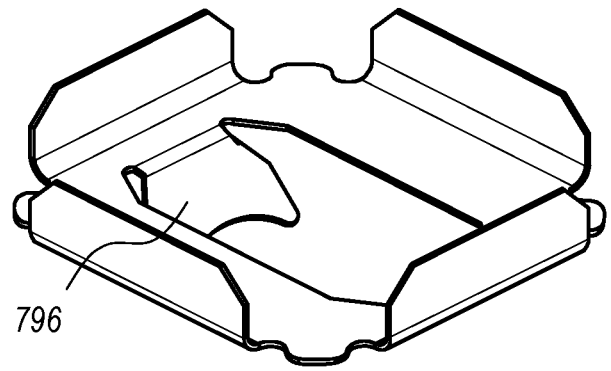
Figure 47C:
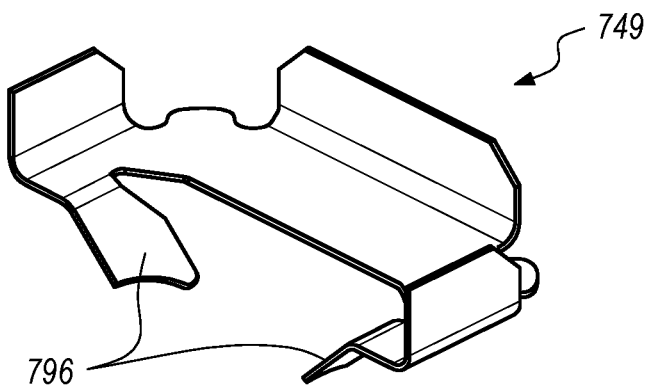
Figure 48:
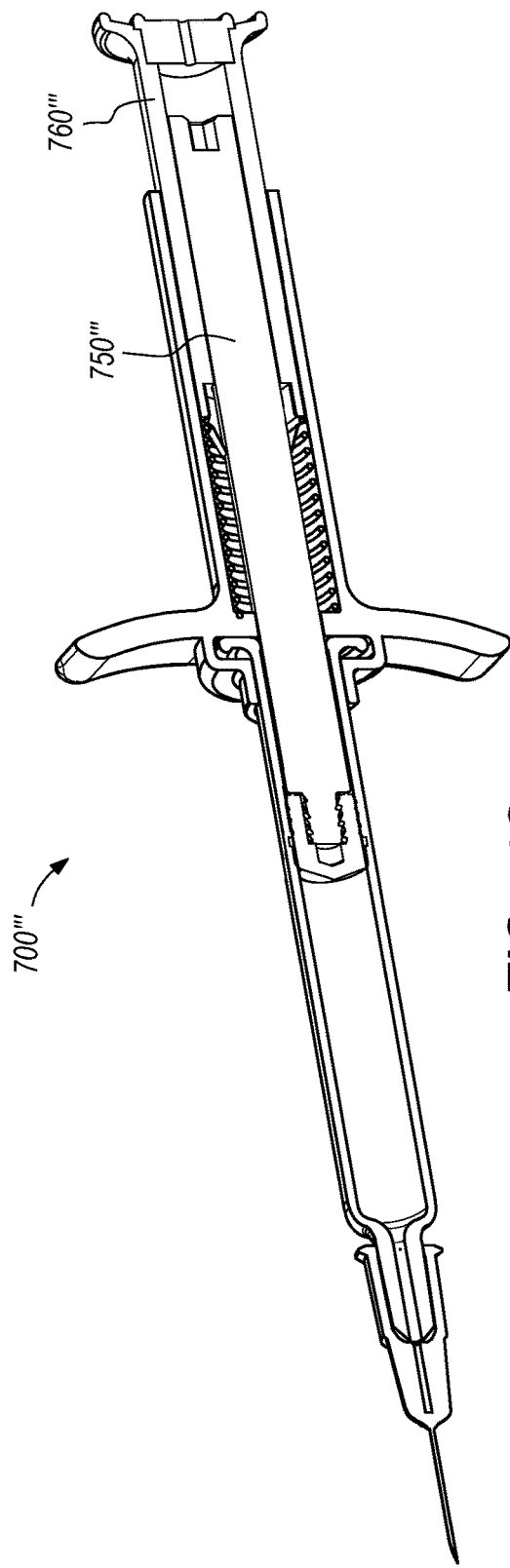
FIGS. 48-54 illustrate various aspects of a multiple site injection system and a multiple site injection method according to some embodiments.
Figure 49:
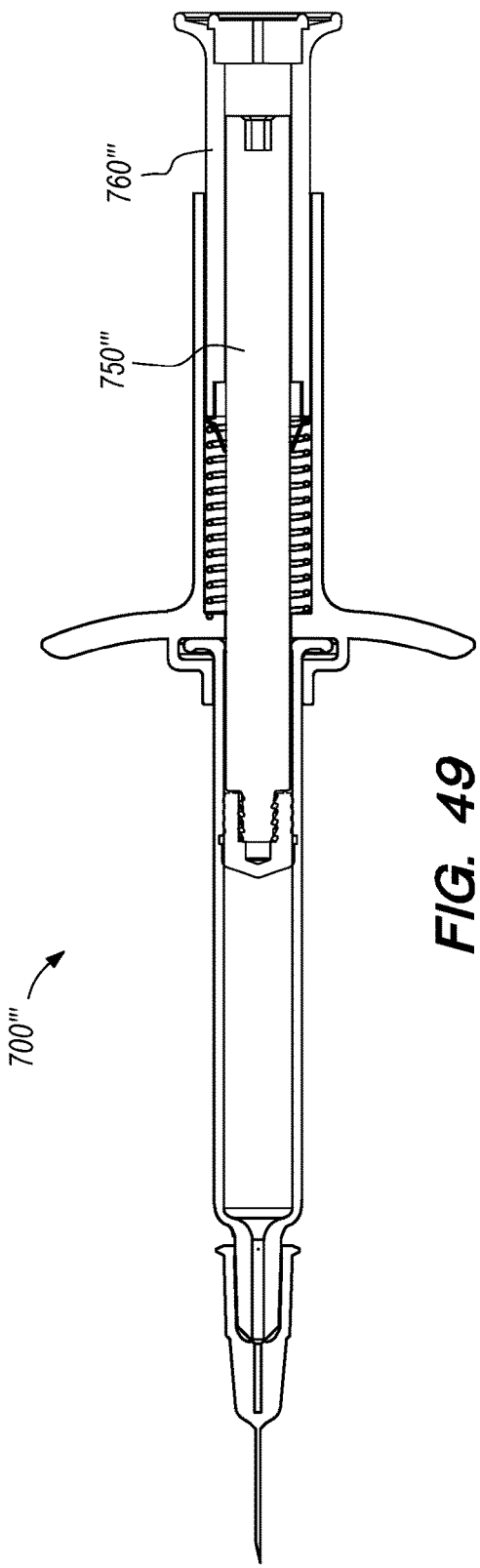
Figure 50:
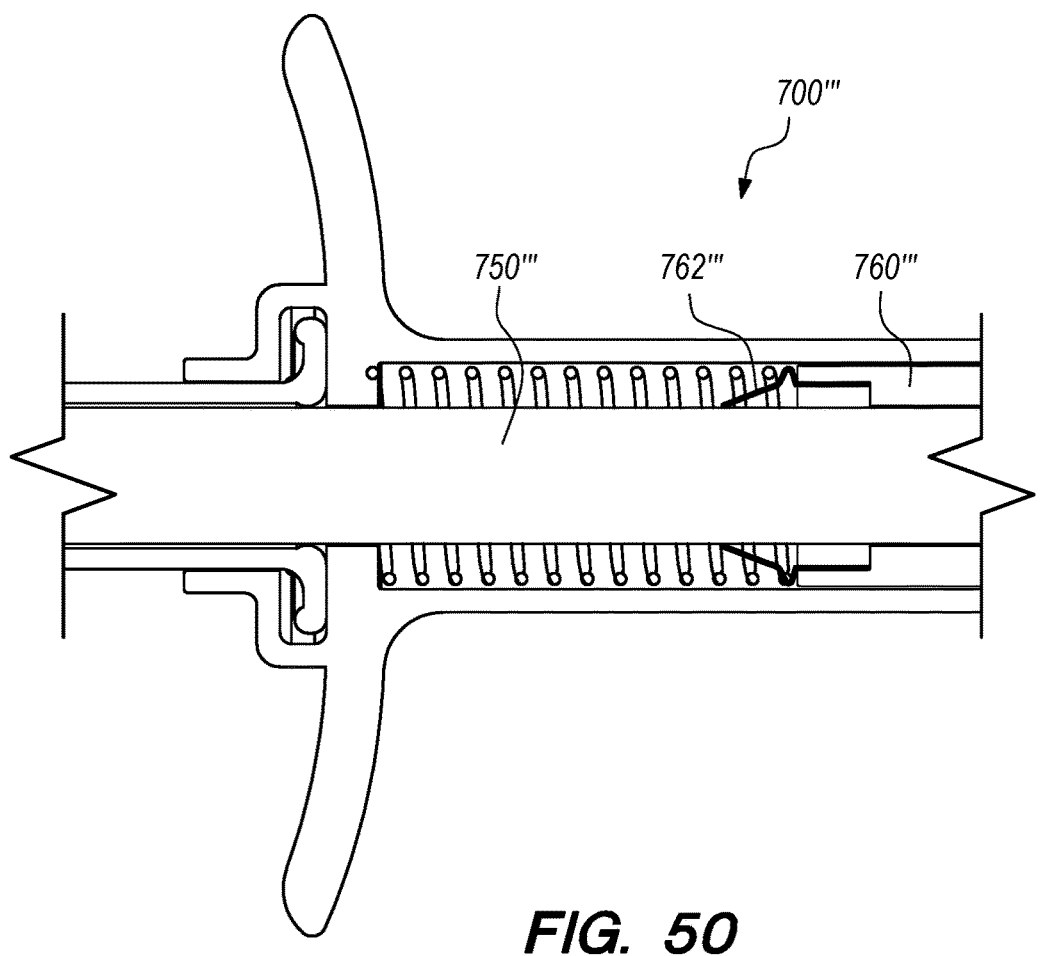
Figure 51:
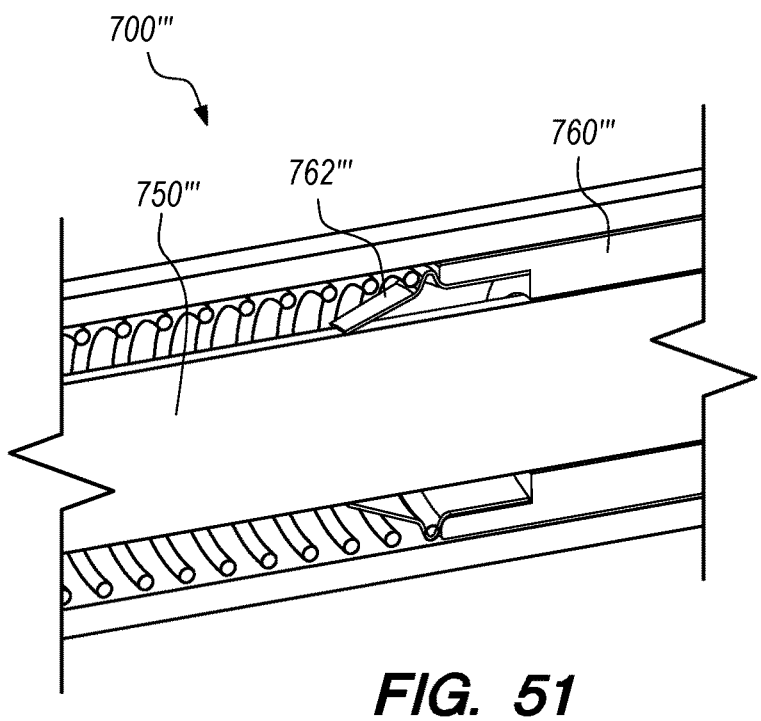

FIGS. 43-47C depict some components for limiting proximal movement of a plunger member 750" of a multiple site injection system 700" according to some embodiments. As shown in FIGS. 43-46, the finger flange 740" of the system 700" defines a chamber 747 configured to hold an anti-retraction mechanism 749. As shown in FIGS. 47A-47C, the anti-retraction mechanism 749 includes a pair of brake tabs 796 configured to allow the plunger tube 750" to move distally relative to the anti-retraction mechanism 749, while limiting proximal movement relative to the anti-retraction mechanism 749. Other aspects of the anti-retraction mechanism 749 are described in co-owned U.S. patent application Ser. No. 62/864,509, the contents of which are fully incorporated herein by reference as though set forth in full.

FIGS. 48-54 depict a multiple site injection system 700''' according to some embodiments. The system 700''' depicted in FIGS. 48-54 is similar to the system 700 depicted in FIGS. 16-28, and identical components are described above. The difference between the system 700''' depicted in FIGS. 48-54 and the system 700 depicted in FIGS. 16-28 is that the system 700''' depicted in FIGS. 48-54 includes a plunger member 750''' without any teeth (compare to plunger member 750 the system 700 depicted in FIGS. 16-28). Instead of using teeth to ratchet the plunger member 750''' forward, the ratchet tube 760''' includes a pair of the elastically deformable leaves 762''' that are made of metal and configured to deform the softer surface of the plunger member 750''', which may be made of a polymer.

Figure 52A:
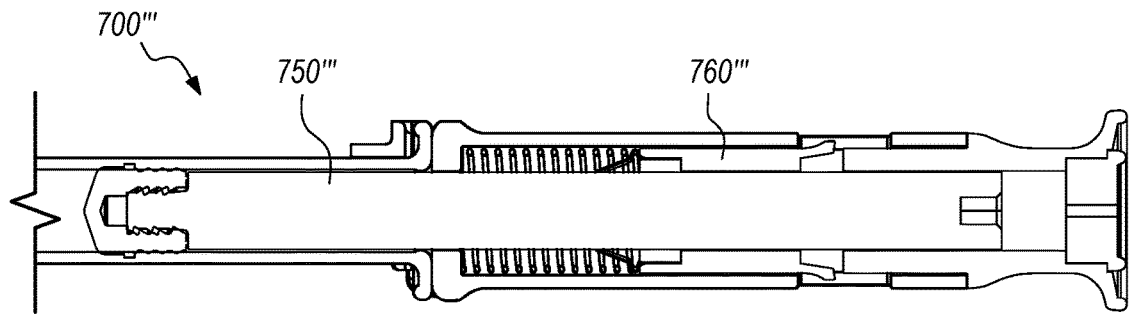
Figure 52B:
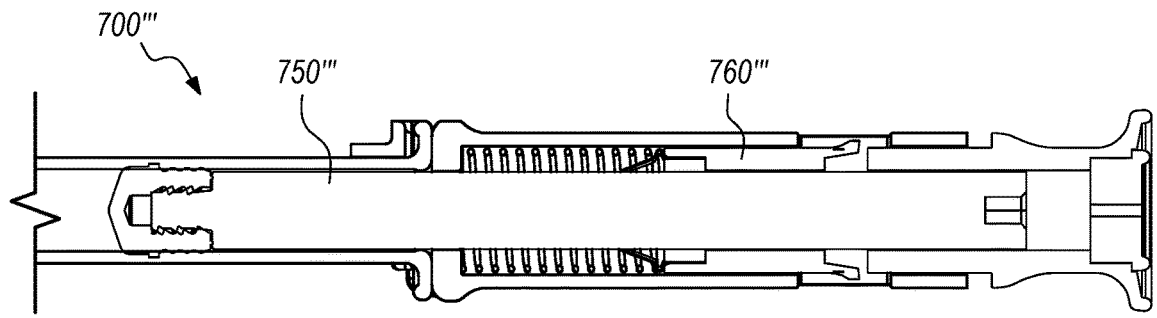
Figure 52C:
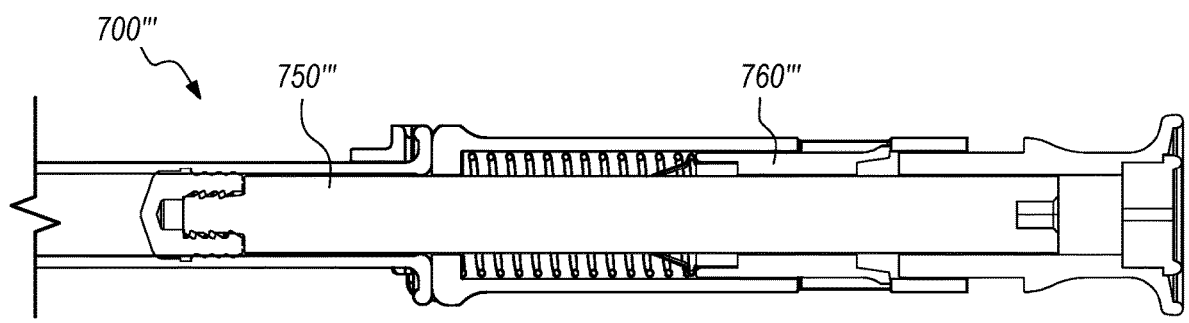
Figure 53:
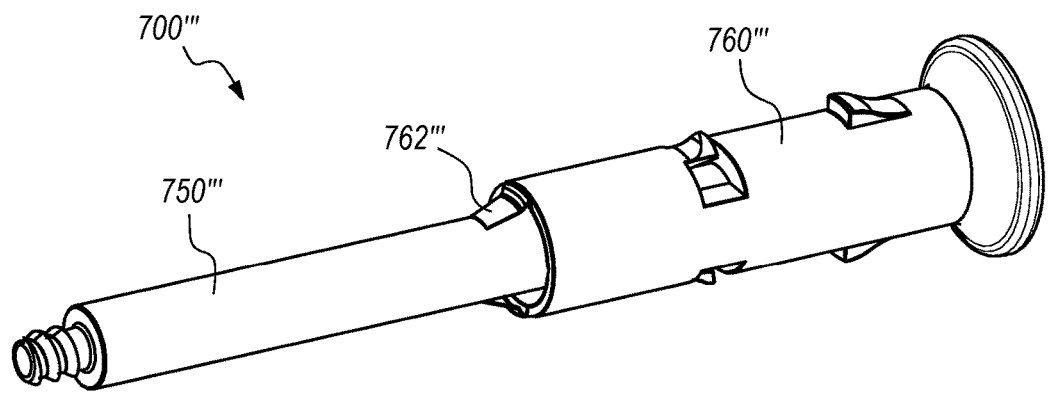
Figure 54:
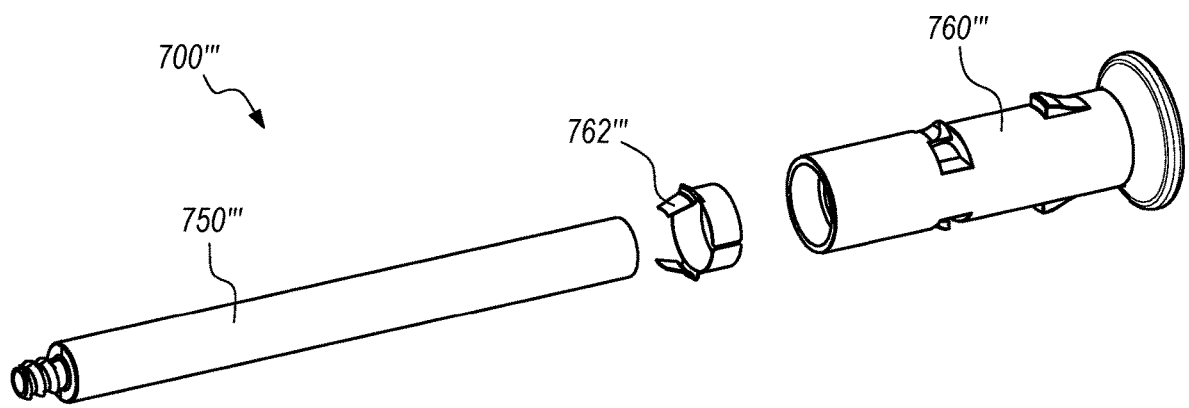
Figure 55:
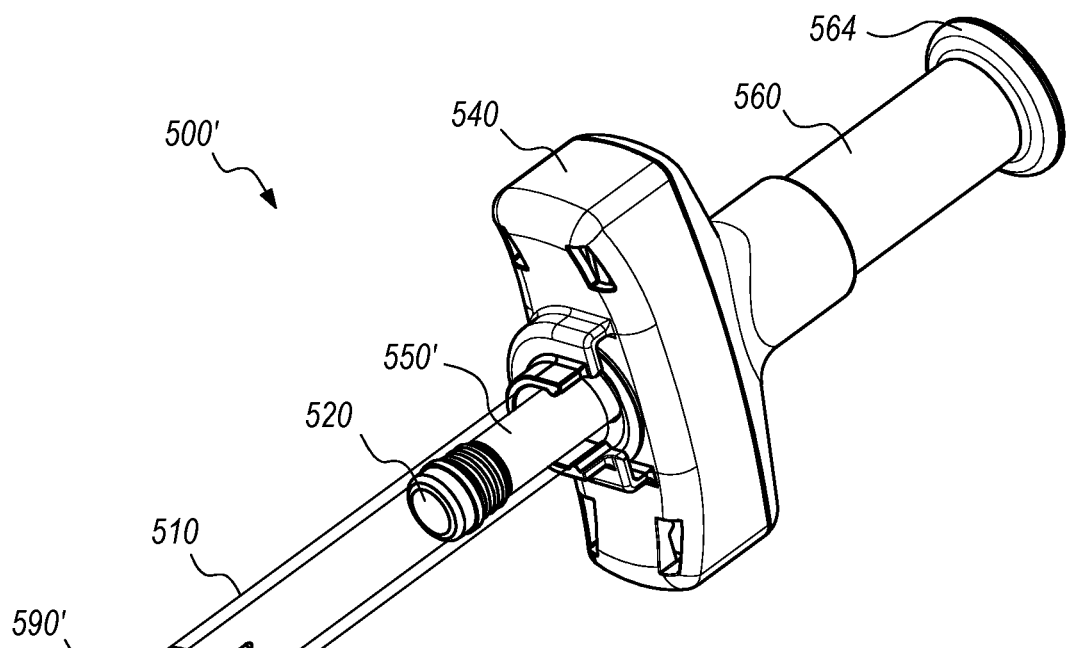
FIGS. 55-67 illustrate various aspects of a multiple site injection system and a multiple site injection method according to some embodiments.
Figure 56:
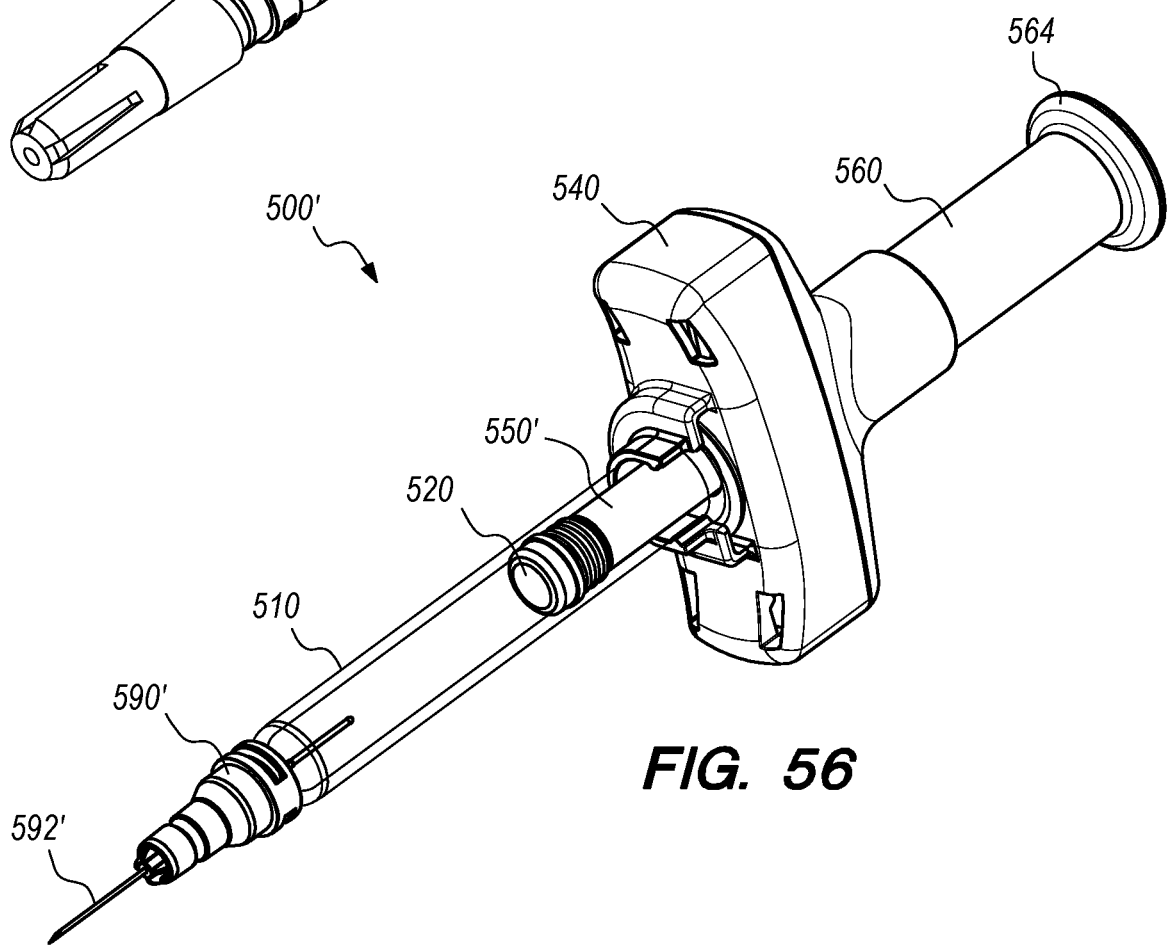

FIGS. 52A-52C depict one injection in a multiple site injection method using the system 700'''. When the ratchet tube 760''' is pushed distally, the elastically deformable leaves 762''' dig into the surface of the plunger member 750''' and move the plunger member 750''' distally. At the end of an injection, a return spring pushes the ratchet tube 760''' proximally while the plunger member 750''' is held in place by friction or by an anti-retraction mechanism as described above. Because the plunger member 750''' has no teeth, the multiple site injection system 700''' can be used to deliver less than a full dose without disrupting the dosage of the following injection by advancing the ratchet tube 760''' less than a full stroke before releasing the ratchet tube 760'''.

FIGS. 55-67 depict a multiple site injection system 500' according to some embodiments. The system 500' depicted in FIGS. 55-67 is similar to the system 500 depicted in FIGS. 6-15C, and identical components are described above. The difference between the system 500' depicted in FIGS. 55-67 and the system 500 depicted in FIGS. 6-15C is that the system 500' depicted in FIGS. 55-67 includes a needle retraction mechanism similar to the ones depicted and described in co-owned U.S. patent application Ser. Nos. 14/696,342, 14/543,787, 14/321,706, 62/416,102, 62/431,382, 62/480,276, 62/508,508, 62/542,230, 15/801,239, 15/801,259, 15/801,281, 15/801,304, the contents of which were previously fully incorporated herein by reference as though set forth in full.

Figure 60:
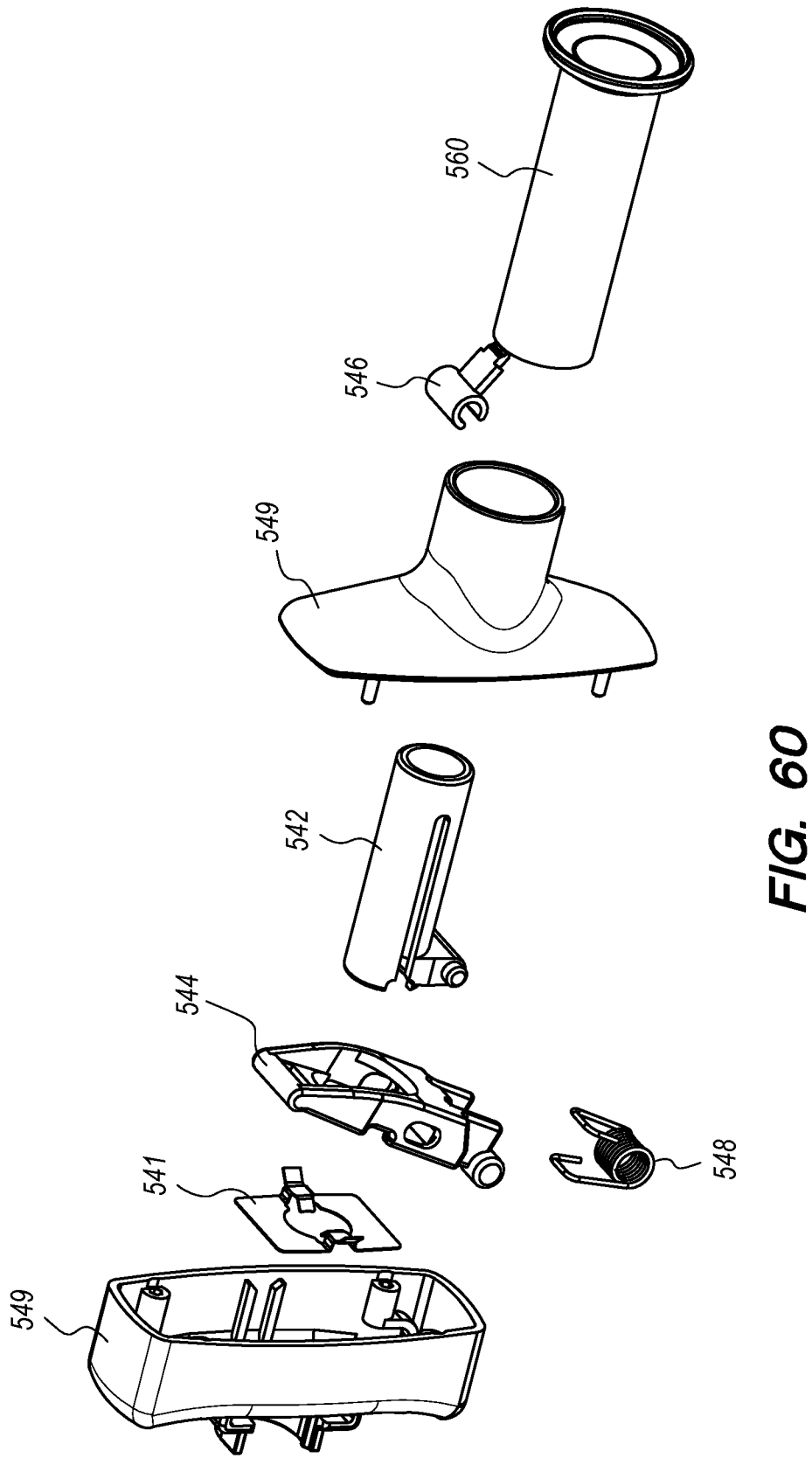
Figure 61:
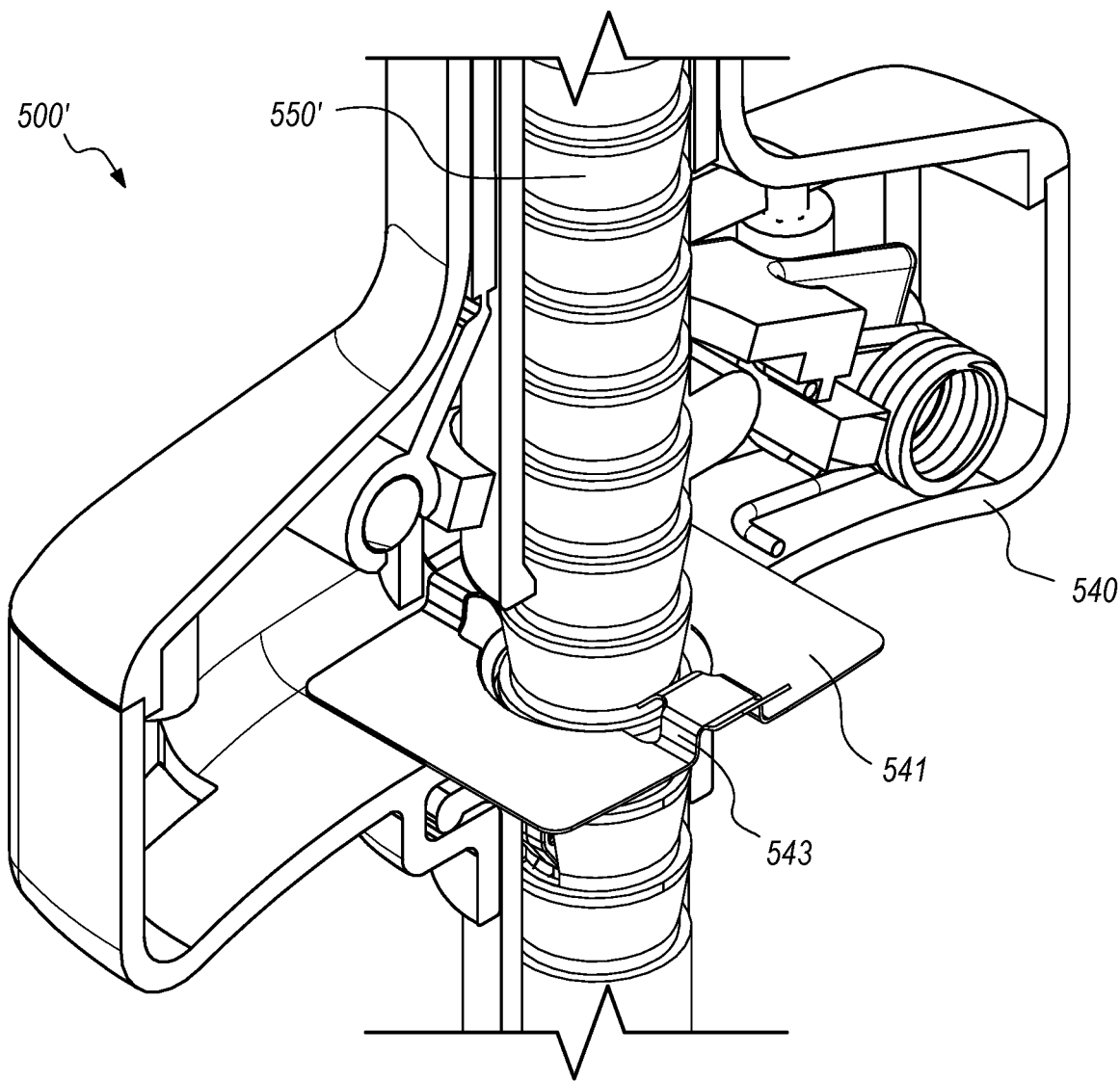
Figure 62A:
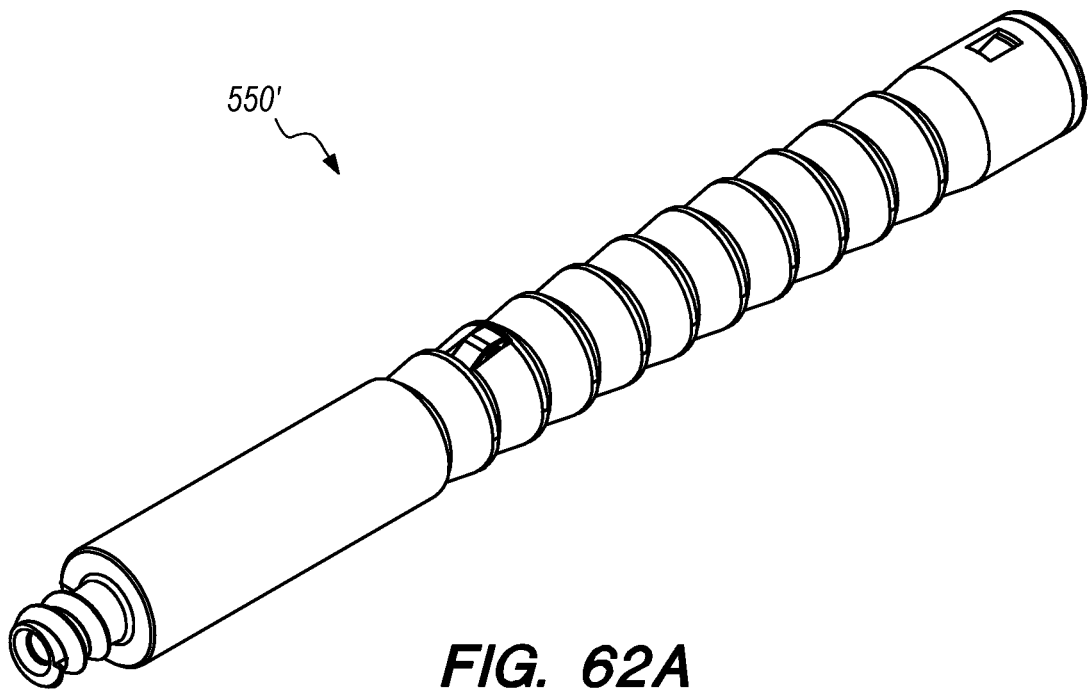
Figure 62B:
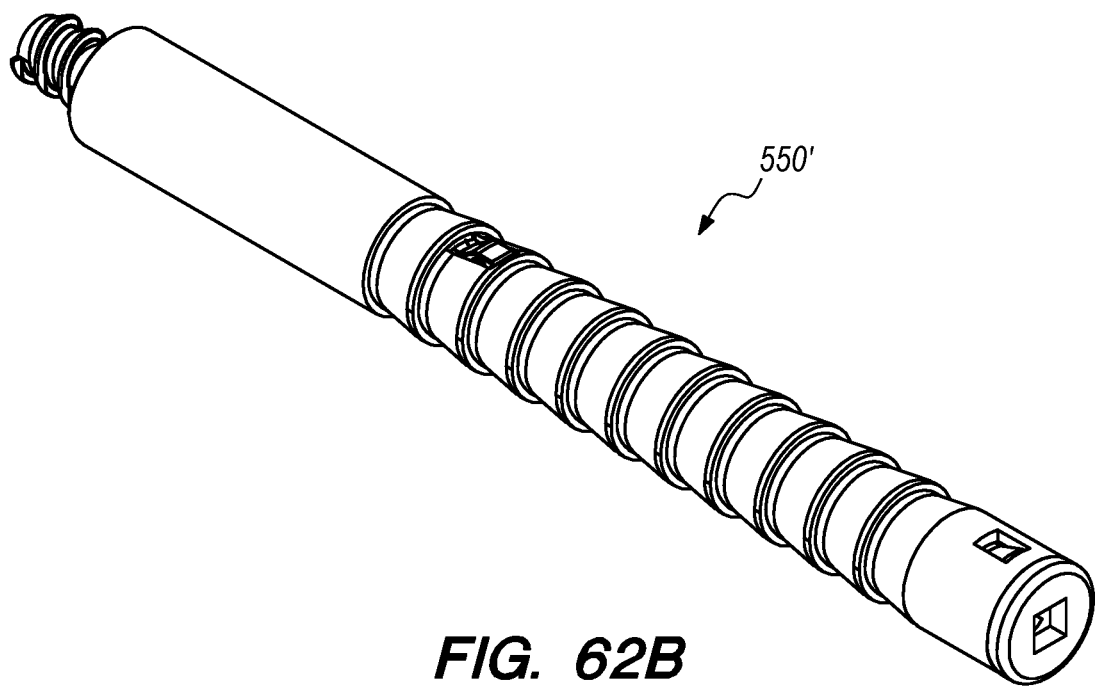

In order to facilitate needle retraction, the needle assembly 590' includes a removably coupled needle 592', and the plunger member 550' includes needle retraction components similar to those in the patent application as described above. As shown in FIGS. 60 and 61, the finger flange 540 also includes an anti-retraction mechanism 541 is configured to allow the plunger tube 550' to move distally relative to the anti-retraction mechanism 541, while limiting proximal movement relative to the anti-retraction mechanism 541. The anti-retraction mechanism 541 includes a pair of brake tabs 543 as shown in FIG. 61. Other aspects of the anti-retraction mechanism 749 are described in co-owned U.S. patent application Ser. No. 62/864,509, the contents of which were previously fully incorporated herein by reference as though set forth in full.

Figure 64:
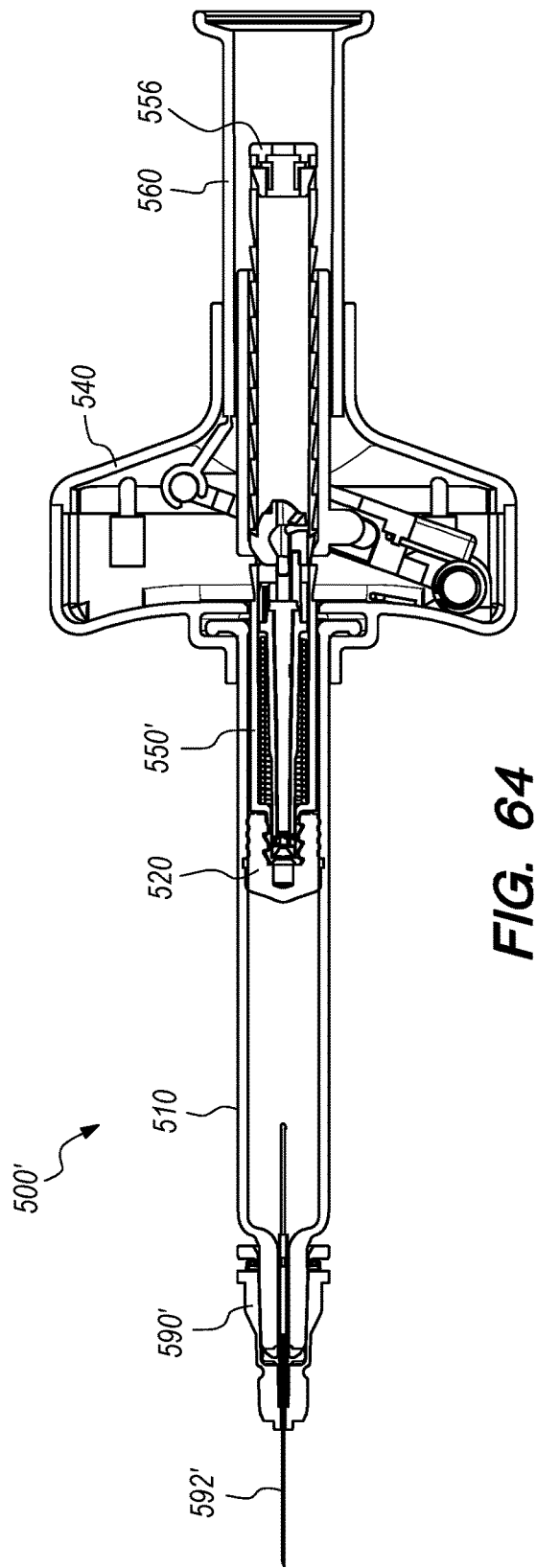
Figure 65:
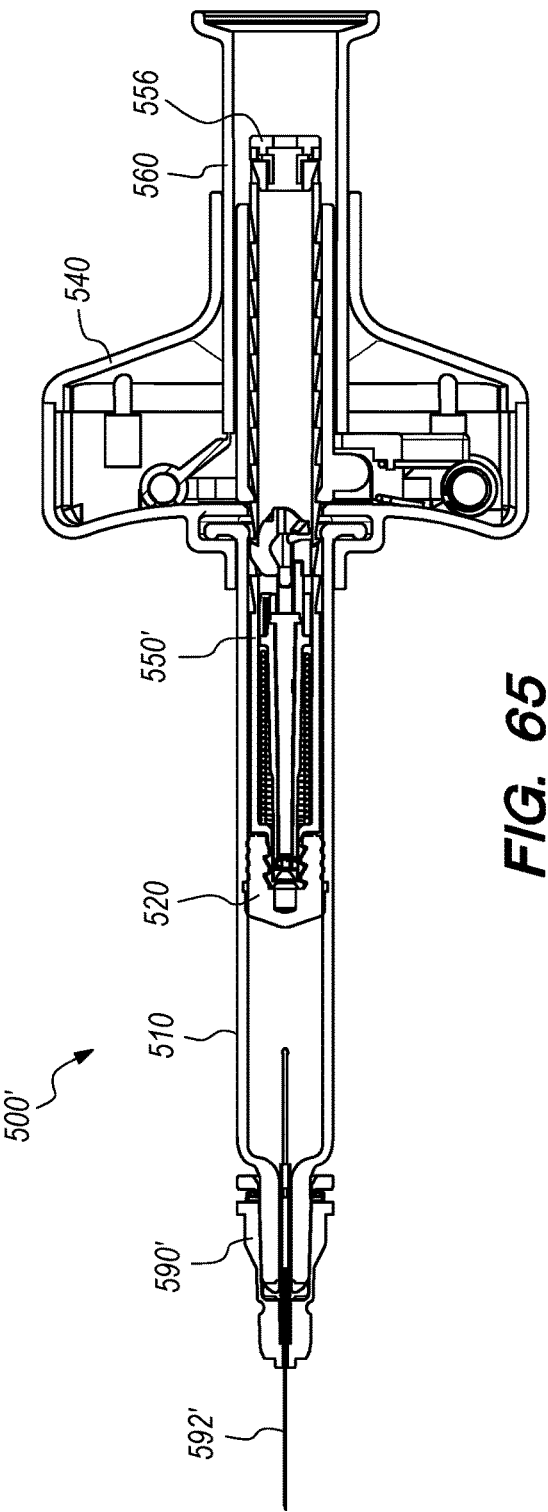
Figure 66:
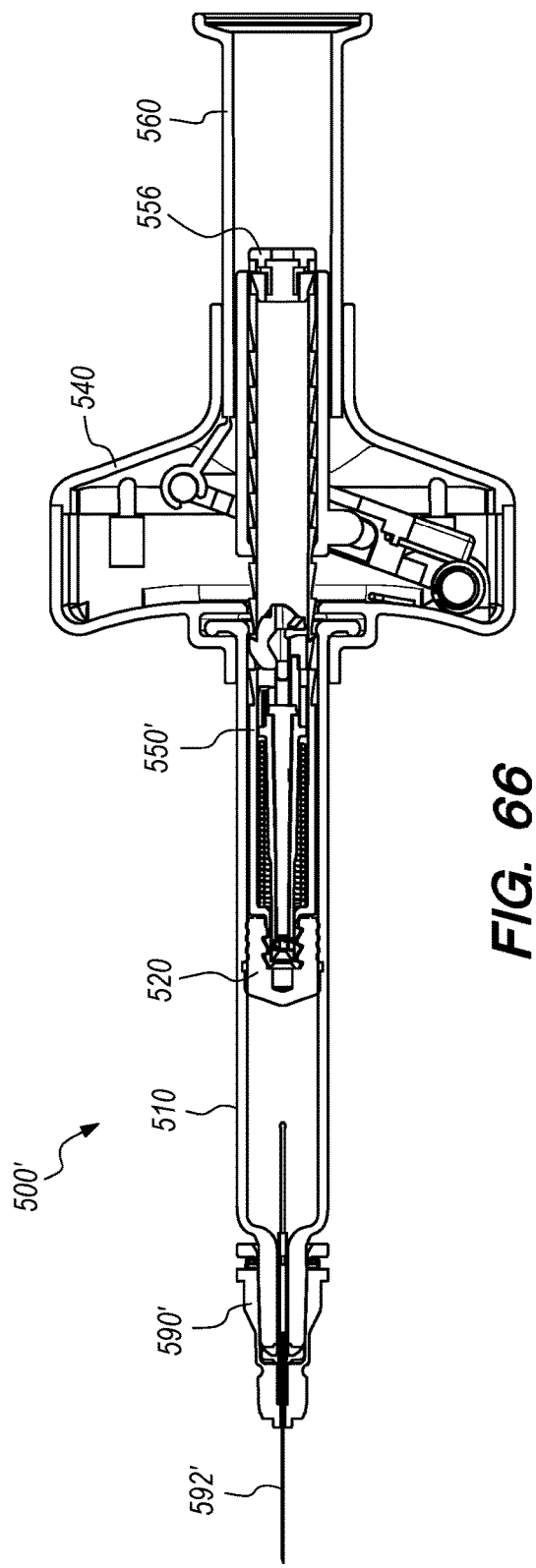

FIGS. 64-66 depict one injection cycle in a multiple site injection method using the system 500'. When the ratchet tube 560 is moved distally from FIG. 64 to FIG. 65, the plunger member 550' is moved distally to eject a single dose from and teary or of the syringe body 510. When the user removes pressure from the thumb pad, a spring in the finger flange restores the ratchet tube 560 proximally to ready the system 500' for the next injection/dose.

Figure 57:
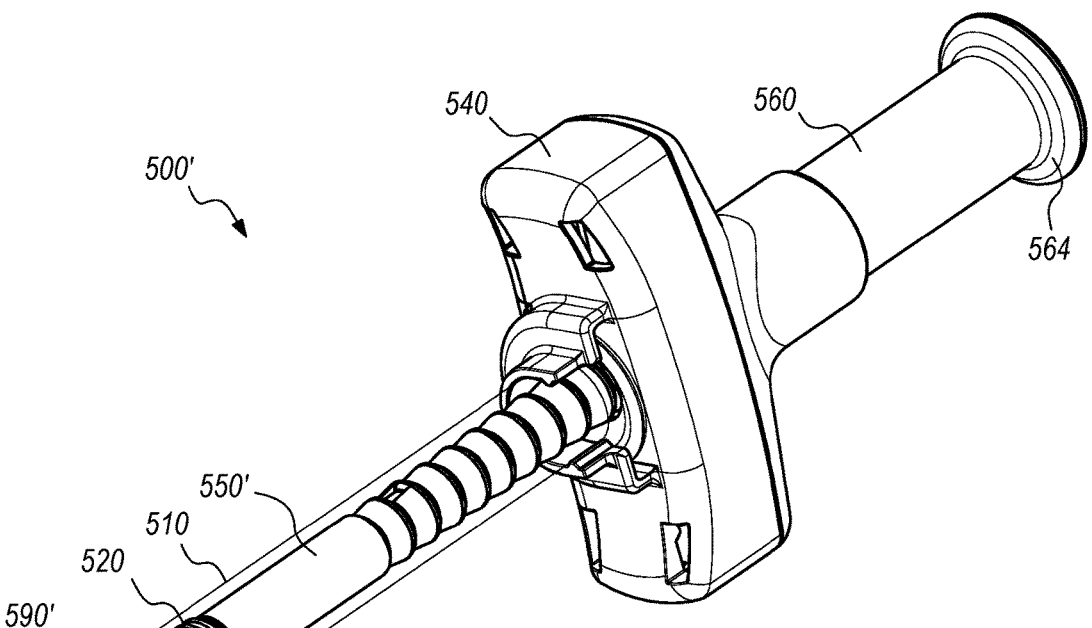
Figure 58:
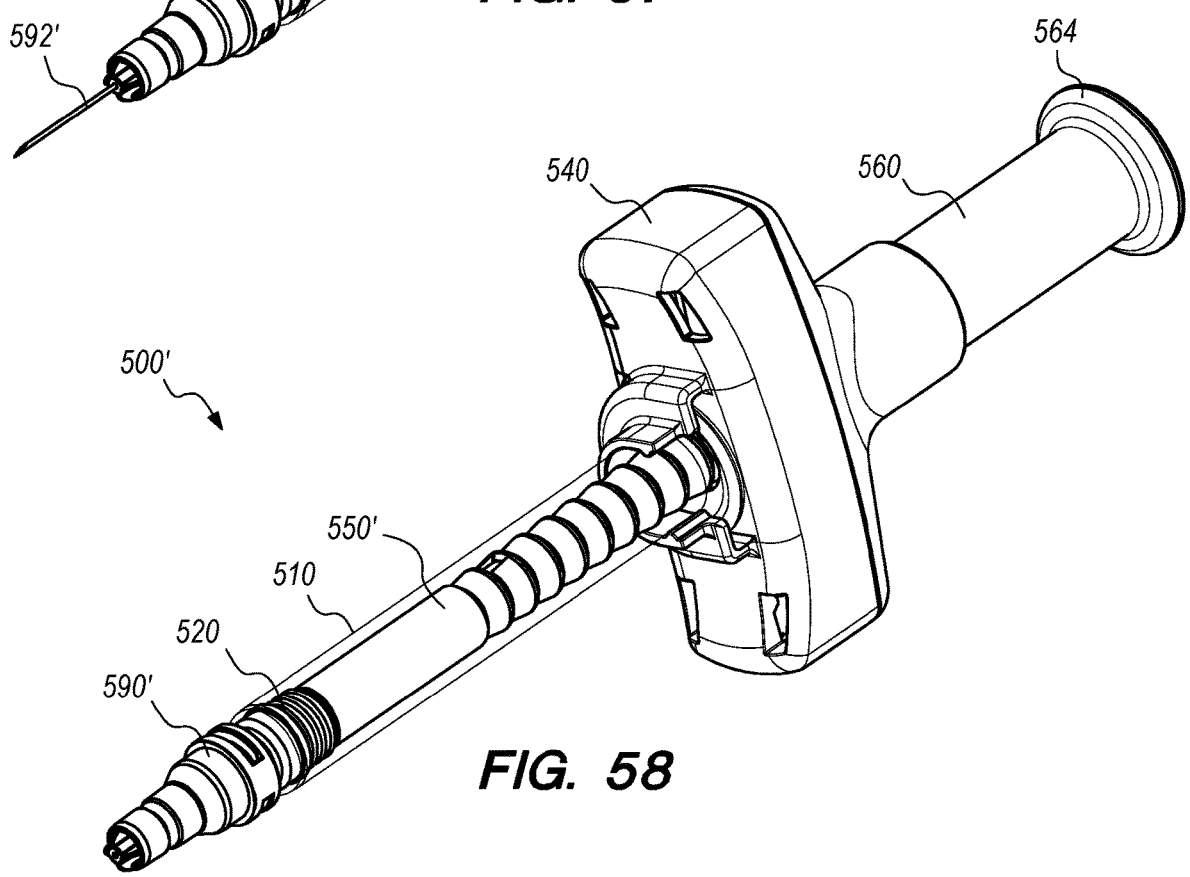
Figure 67:
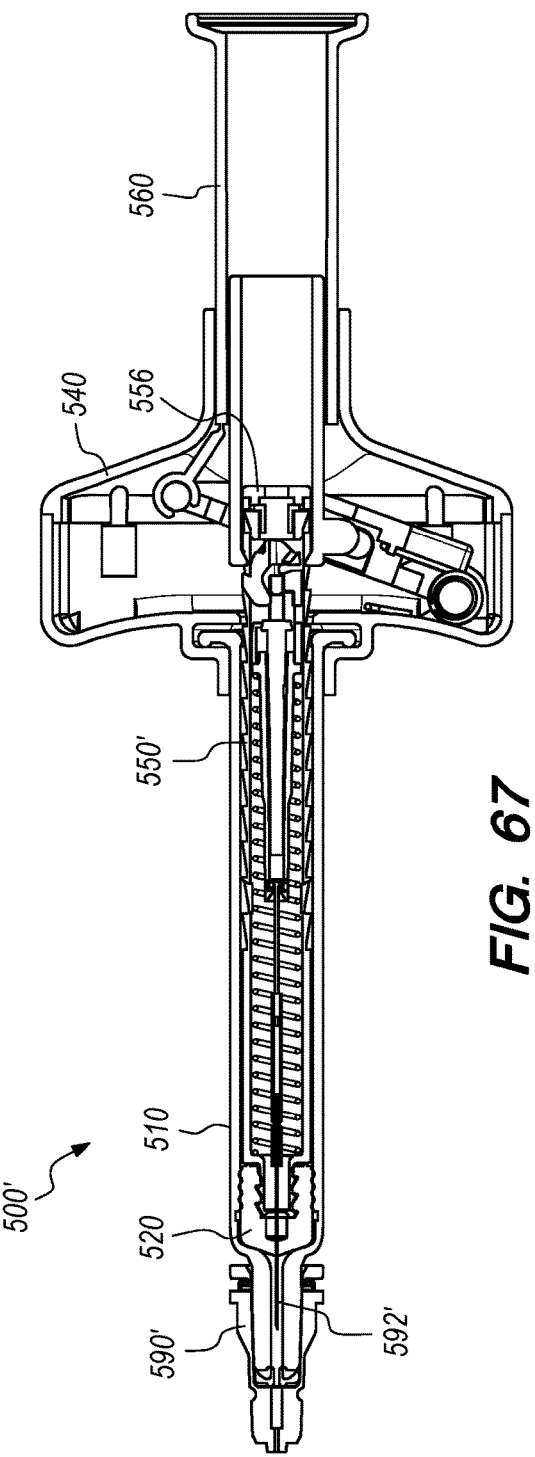

FIG. 57 depicts when the plunger member 550' and the stopper member 520 have advanced almost to a distal end of the syringe body 510 leaving only a single dose in the interior of the syringe body 510. After the last dose in the interior of the syringe body 510 is delivered, as shown in FIGS. 58 and 67 the retraction mechanism pulls the needle 592' inside of the plunger member 550' to minimize the risk of an accidental needle stick.

Figure 59A:
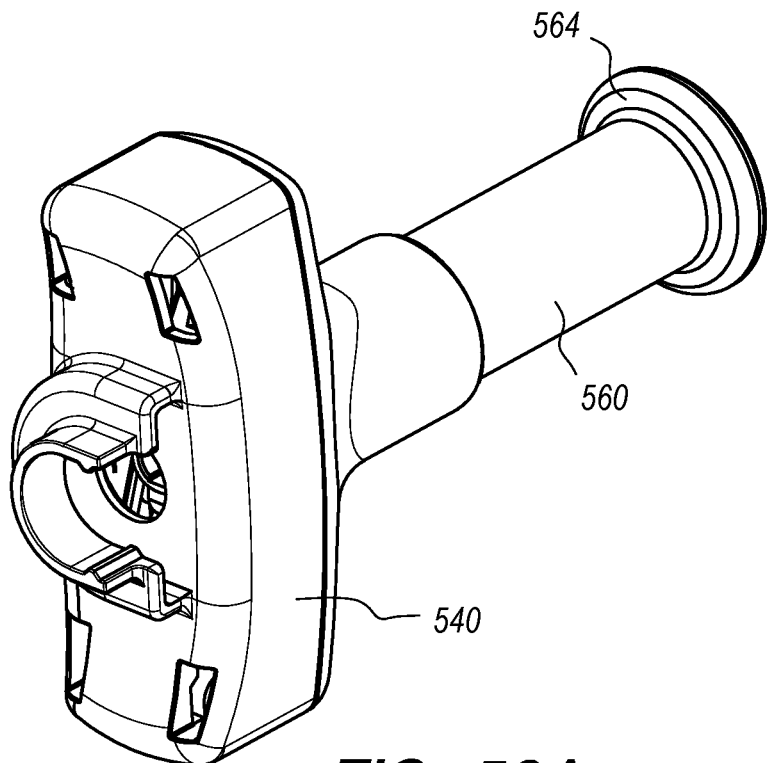
Figure 59B:
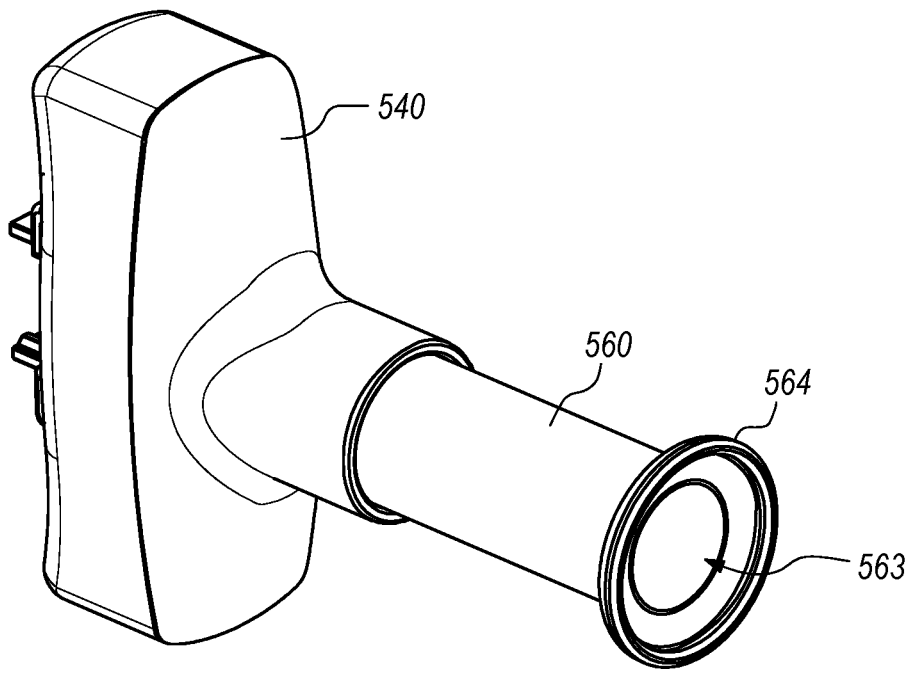

FIGS. 59A and 59B depict a finger flange assembly 540 prior to being snapped onto a syringe body. This finger flange assembly 540 is installed onto the syringe body in a similar fashion to the finger flange described in FIG. 12-13. The finger flange assembly 540 includes a plunger tube 560, which has an integral thumbpad 564 that has an open proximal end 563 for insertion of the plunger member for coupling to the stopper. The proximal end of the integral thumbpad 564 may be sealed with a plug after insertion of the plunger member.

Figure 63:
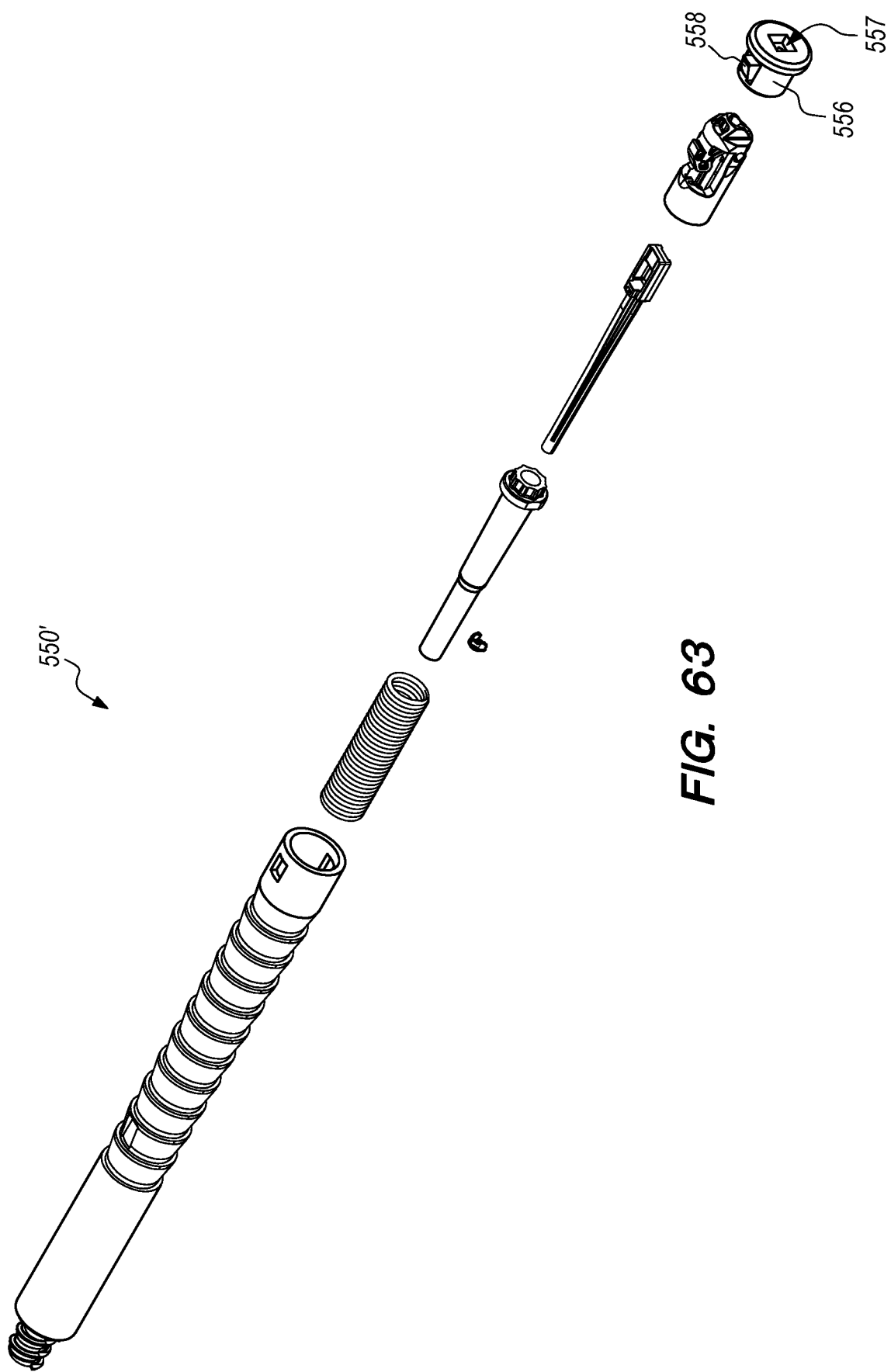

FIG. 63 depicts the plunger member 550' and its components in an exploded view. In particular, a plunger cap 556 is disposed at the proximal end of the plunger member 550'. The plunger cap 556 includes a drive recess 557 configured to facilitate rotation of the plunger member 550' to threaded coupling of the plunger member 550' to a stopper member. The plunger cap 556 also includes a pair of latches 558 configured interfere with corresponding openings in the plunger member 550' to secure the plunger cap 556 thereto. Securing the plunger cap 556 to the plunger member 550' contains the needle retraction components (e.g., needle, spring, spring latch, and needle receiving member) inside of the plunger member 550' after needle retraction. The needle retraction components in the plunger member 550' are similar to the ones depicted and described in co-owned U.S. patent application Ser. Nos. 14/696,342, 14/543,787, 14/321,706, 62/416,102, 62/431,382, 62/480,276, 62/508, 508, 62/542,230, 15/801,239, 15/801,259, 15/801,281, 15/801,304, the contents of which were previously fully incorporated herein by reference as though set forth in full.

Figure 68:
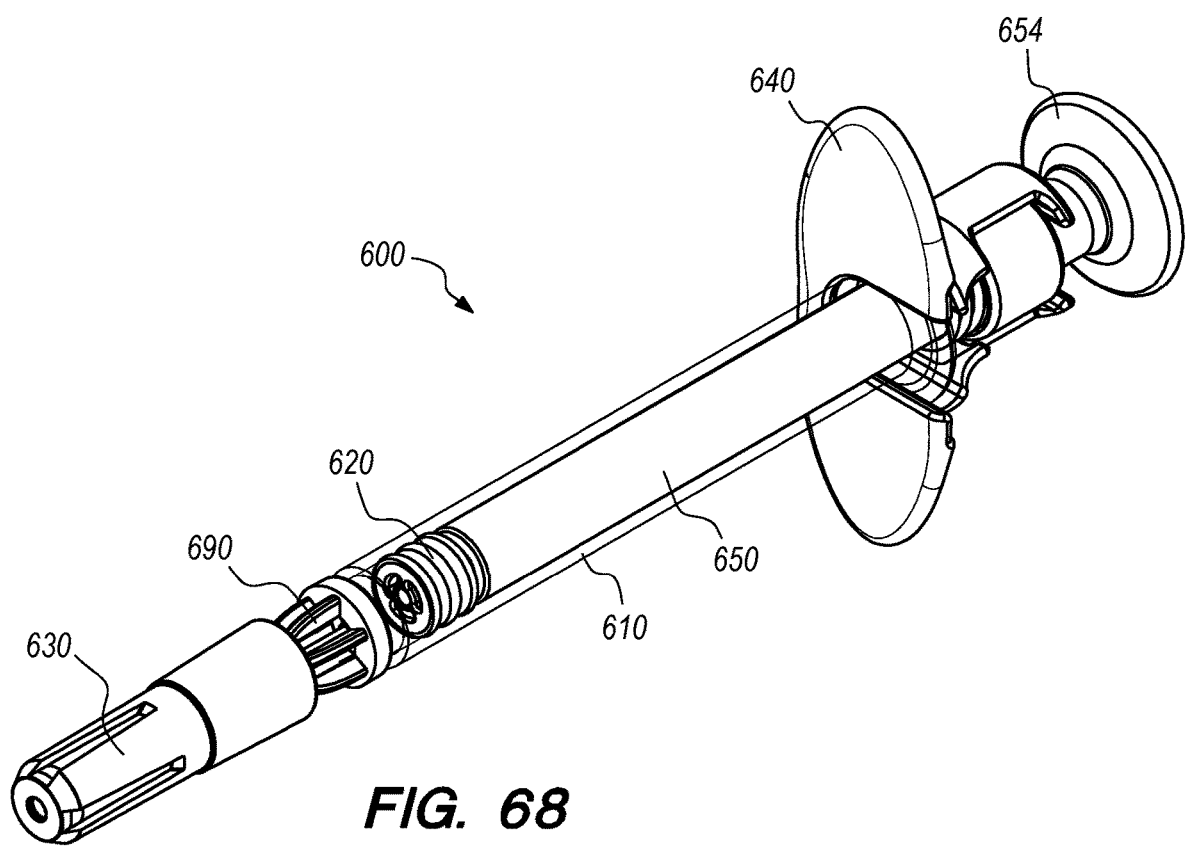
Figure 69:
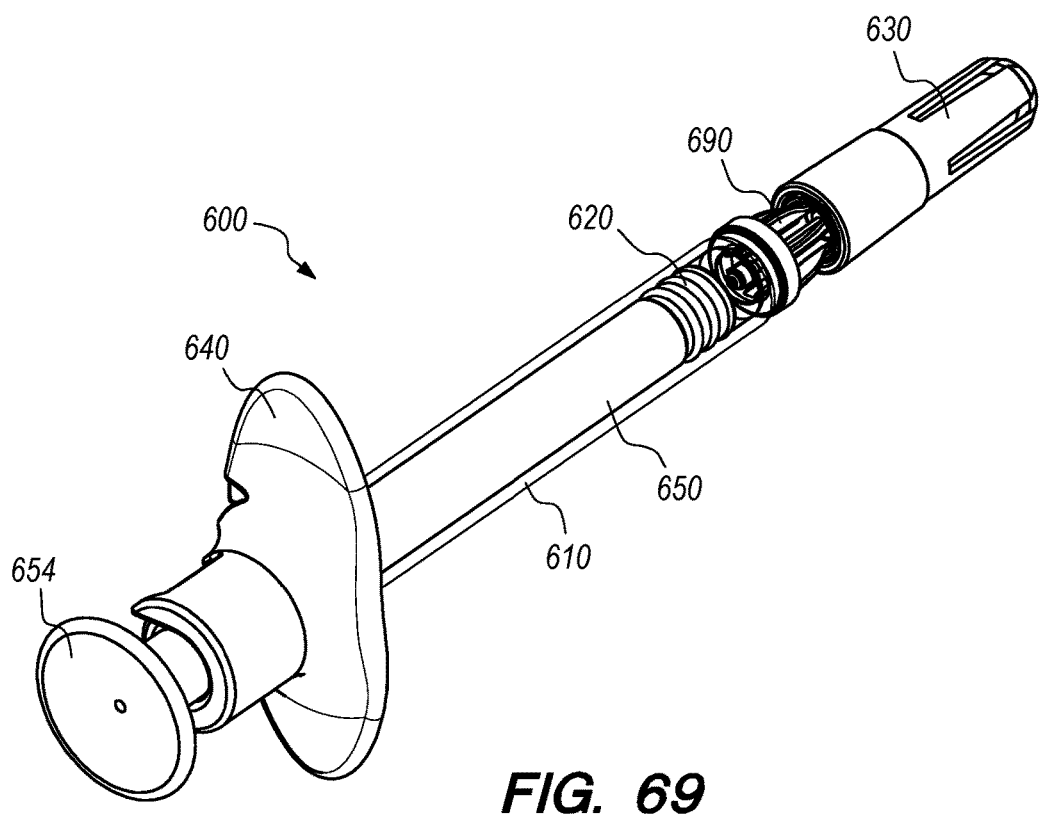

FIGS. 68-74 depict a multiple site injection system 600 according to some embodiments. As shown in FIGS. 68 and 69, the system 600 includes a syringe body 610, a needle assembly 690, a needle cover 630, a stopper member 620, a plunger member 650, and a finger flange 640. Many of these system components (e.g., the syringe body 610, the stopper member 620, and the needle cover 630) may be off-the-shelf components to utilize the existing and relatively well-controlled supply chain, and the corresponding assembly machinery and personnel. The plunger member 650 includes a thumb pad 654, coupled to a proximal end thereof to facilitate user application of a distally directed force to the plunger member 650 and the stopper member 620 coupled thereto. As explained below, the system 600 also includes an injectable fluid (e.g., medications) disposed in a chamber in the plunger member 650.

Figure 70:
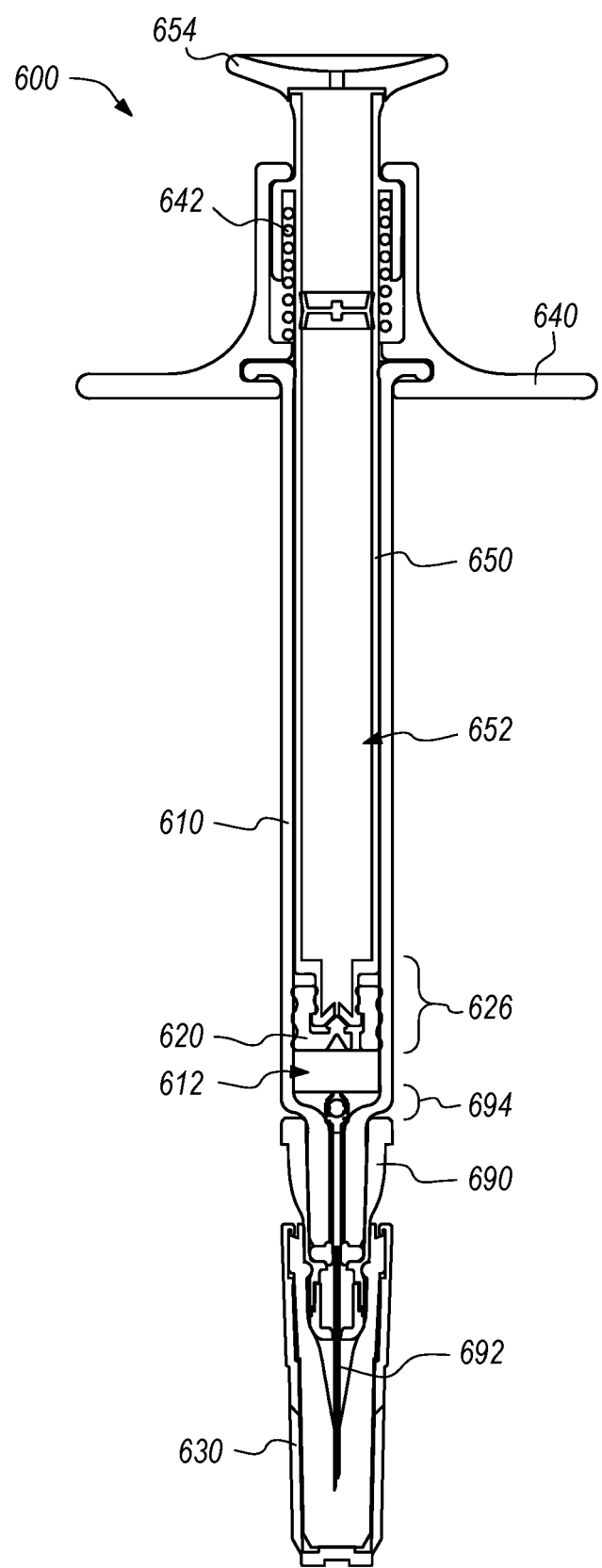

FIGS. 70 and 71 depict the multiple site injection system 600 with and without the needle cover 630 attached. With the needle cover 630 removed, as shown in FIG. 71, the system 600 is ready for use. As shown in FIGS. 70 and 71, the plunger member 650 also includes a proximal chamber 652 in which can be stored the injectable fluid. The proximal chamber 652 is open at a distal end 656 of the plunger member 650.

As shown in FIG. 72, the distal end 656 of the plunger member 650 defines a distally directed cone with an opening bid approximately the center thereof. The stopper member 620 includes an internal cavity 622 in which the distal end 656 of the plunger member 650 is movably disposed. The stopper member 620 also includes a proximally directed protrusion 624 and an opening 628. Together, the distal end 656 of the plunger member 650, and the internal cavity 622 and the proximally directed protrusion 624 of the stopper member 620 form a proximal one-way valve 626. The proximal one-way valve 626 is fluidly coupled between the proximal chamber 652 in the plunger member 650 and a distal chamber 612 defined by the stopper member 620 and a distal end of the syringe body 610. In the configuration depicted in FIG. 72, the proximal one-way valve 626 is open because the distal end 656 of the plunger member 650 is pulled proximally away from the proximally directed protrusion 624 while the stopper member 620 is pulled distally by glide friction between the stopper member 620 and the syringe body 610 and vacuum in the distal chamber 612, thereby forming a flow path between the opening in the distal end 656 of the plunger member 650 and the opening 628 in the stopper member 620. The proximal one-way valve 626 can be placed in this close configuration by applying a proximally directed force to the plunger member 650 to pull the distal end 656 of the plunger member 650 away from the proximally directed protrusion 624 of the stopper member 620 as explained below.

Figure 73:
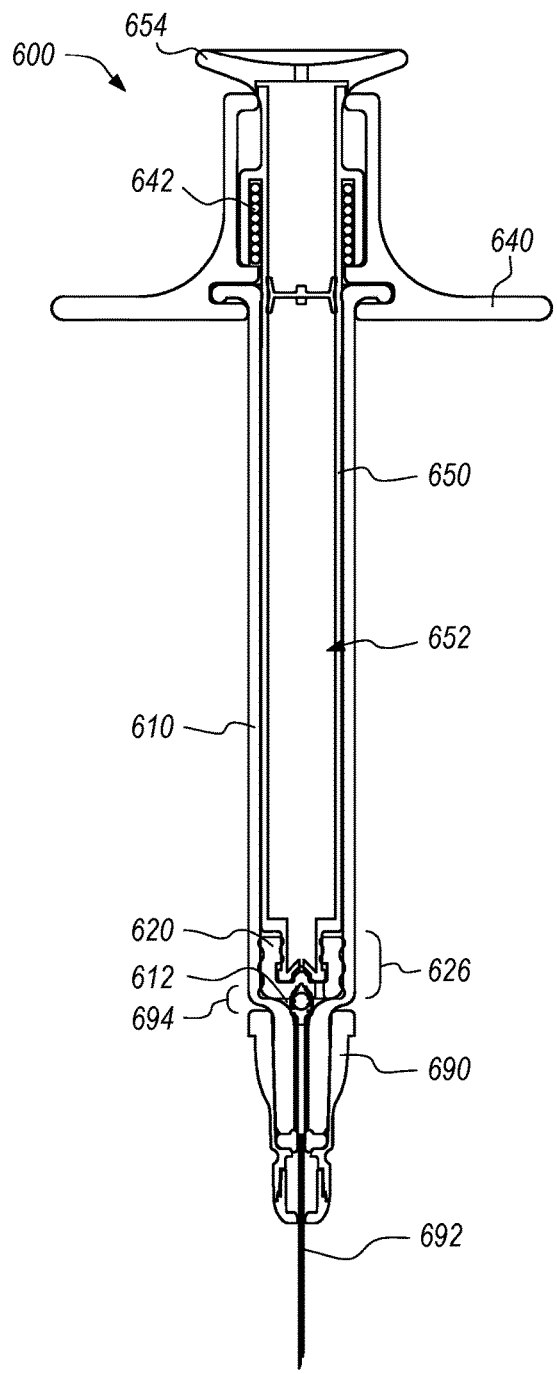
Figure 74:
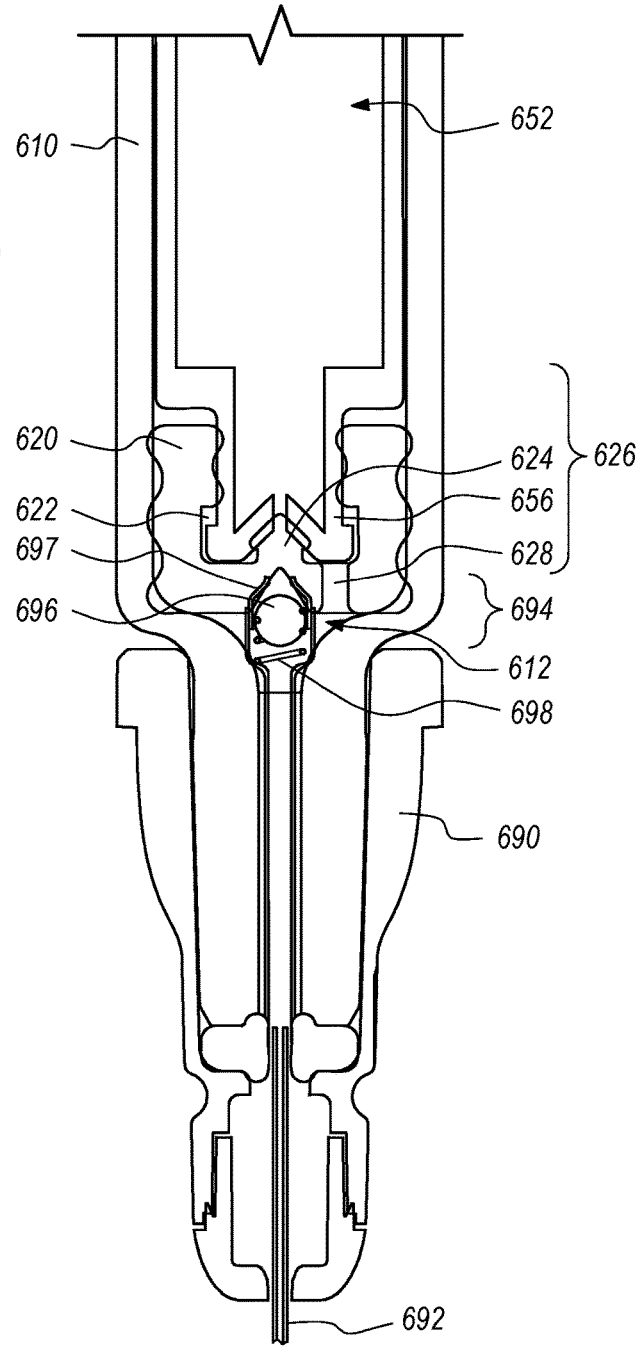

As also shown in FIG. 72, the proximal end of the needle assembly 690 includes a distal one-way valve 694. The distal one-way valve 694 includes a spherical member 696 inside of a valve body 697, and a valve spring 698, which biases the spherical member 696 proximally to close a proximal opening in the valve body 697. In FIG. 72, the distal one-way valve 694 is in the close configuration. With continued application of distally directed force to the plunger member 650 and the stopper member 620 as shown in FIGS. 73 and 74, any incompressible fluid in the distal chamber 612 will transmit the force to the spherical member 696 and overcome the force of the valve spring 698 to move the spherical member 696 distally and opened the distal one-way valve 694. Opening the distal one-way valve 694 fluidly couples the distal chamber 612 and the needle 692 for injection. The specific valves in this embodiment are exemplary. Other types of one-way valves are within the scope of the disclosure.

As shown in FIGS. 71 and 73, the finger flange 640 includes a return spring 642, which biases the plunger member 650 in a proximal position (see e.g., FIG. 71). When a user applies a distally directed force to the thumb pad 654 to perform an injection, the distally directed force overcomes the proximally directed force exerted by the return spring 642 on the thumb pad 654 and advances the plunger member 650 a predetermined distance to a distal position (see e.g. FIG. 73). Moving the plunger member 650 at the stopper member 620 from the proximal position to the distal position ejects a known volume (e.g., 0.1 ml, microdose) from the distal chamber 612 through the needle 692. A spectrum of volumes (e.g., up to 0.1 ml) may also be ejected from the distal chamber 612 by moving the plunger member 650 only a portion of the distance to the distal position.

When the plunger member 650 is advanced to perform an injection, the proximal one-way valve 626 is closed to prevent retrograde travel of fluid from the distal chamber 612 to the proximal chamber 652. In the configuration depicted in FIG. 74, the proximal one-way valve 626 is closed because the cone at the distal end 656 of the plunger member 650 is pressed into the proximally directed protrusion 624, thereby closing the opening in the distal end 656 of the plunger member 650. The proximal one-way valve 626 can be placed in this close configuration by applying a distally directed force to the plunger member 650 to push the distal end 656 of the plunger member 650 into the proximally directed protrusion 624 of the stopper member 620. The stopper member 620 and the proximally directed protrusion 624 held in place by friction between the stopper member 620 and the syringe body 610 and positive pressure in the distal chamber 612. At the same time, the distal one-way valve 694 is opened by the increased pressure in the distal chamber 612 to allow injection of fluid from the distal chamber 612 through the needle 692.

When the user releases the thumb pad 654, the return spring 642 moves the plunger member 650 proximally to return to its proximal position (see e.g., FIG. 71). When the plunger member 650 returns to its proximal position (see e.g., FIG. 72), the distal one-way valve 694 is in its closed configuration because of the vacuum generated in the distal chamber 612 and biasing by the valve spring 698. At the same time, the proximal one-way valve 626 is in its open because the distal end 656 of the plunger member 650 moves proximally and the internal cavity 622 of the stopper member 620 to open the proximally directed protrusion 624. This allows the injectable fluid in the proximal chamber 652 in the plunger member 650 to be drawn into the distal chamber 612 by the vacuum therein generated by the proximal movement of the stopper member 620. Movement of injectable fluid from the proximal chamber 652 to the distal chamber 612 readies the multiple site injection system 600 for another injection. The injection process shown in FIGS. 71-74 can be repeated to give a series of injections having a fixed volume (e.g., 0.1 ml, microdose).

Accordingly, a user may perform a series of injections by alternately depressing and releasing the thumb pad 654. With the embodiment depicted in FIGS. 68-74, the user may optionally depress the plunger member 650 less than its complete travel distance (e.g., to deliver a half or quarter dose). Regardless of the distance that the plunger member 650 is depressed, the return stroke will draw a sufficient amount of injectable fluid from the proximal chamber 652 to the distal chamber 612 to prepare for the next injection.

While various embodiments have been described with specific connectors (e.g., slip and Luer), these embodiments can be used with any known injection system connectors. While various embodiments have been described with staked needles and needle connectors, these embodiments can be used with any known permanently coupled needle or needle connector system.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, PTFE, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A system for injecting, comprising:
    a syringe body having proximal and distal ends, a syringe interior, and a syringe flange at the proximal end thereof;
    a finger flange coupled to the syringe flange;
    a stopper member disposed in the syringe interior;
    a plunger member coupled to the stopper member;
    a thumb pad configured to apply a distally directed force to the plunger member;
    a plunger tube disposed coaxially around at least a portion of the plunger member and operatively coupled thereto; and
    a needle hub assembly coupled to the syringe body at its distal end, the needle assembly including,
        a needle having a needle proximal end feature,
        a hub, and
        a needle latching member configured to selectively prevent the needle from moving proximally relative to the hub,
    wherein the thumb pad is movable relative to the plunger member along a longitudinal axis,
    wherein the plunger member comprises
        a needle retention feature disposed in a plunger interior,
        an energy-storage member disposed in the plunger interior, and
        an energy-storage member latching member disposed in the plunger interior, and
    wherein the needle is at least partially retractable into the plunger interior upon manipulation of the plunger tube to transform the energy-storage member latching member from a latched state to an unlatched state.

2. The system of claim 1, further comprising an anti-retraction mechanism configured to limit proximal movement of the plunger member relative to the syringe body.

3. The system of claim 2, wherein the finger flange defines a chamber therein, and
    wherein the anti-retraction mechanism is disposed in the chamber in the finger flange.

4. The system of claim 2, wherein the anti-retraction mechanism comprises a pair of tabs configured to allow the plunger member to move distally relative to the anti-retraction mechanism, the finger flange, and the syringe body while limiting movement of the plunger member relative to the anti-retraction mechanism, the finger flange, and the syringe body.

5. The system of claim 4, wherein the anti-retraction mechanism defines a plane normal to a longitudinal axis of the plunger member.

6. The system of claim 5, wherein each of the pair of tabs extends from the plane in a distal direction.

7. The system of claim 1, further comprising:
a plunger tube return spring operatively coupled to the plunger tube.

8. The system of claim 7, wherein the plunger member comprises a plurality of teeth disposed on an outside surface thereof,
wherein a distal end of the plunger tube comprises a reduced diameter portion configured to interfere with each tooth of the plurality to prevent proximal movement of the plunger member relative to the plunger tube.

9. The system of claim 7, wherein the plunger tube has a proximal position and a distal position, and
wherein the plunger tube return spring biases the plunger tube in the proximal position.

10. The system of claim 7, wherein moving the plunger tube from its proximal position to its distal position ejects a fixed volume of the fluid from the syringe interior.

11. The system of claim 10, the finger flange comprising a distal stopping surface configured to limit distal movement of the plunger tube beyond its distal position, thereby prevents ejection of more than the fixed volume of fluid from the syringe interior.

12. The system of claim 10, wherein the fixed volume is approximately 0.1 ml.

13. The system of claim 7, wherein the needle is selected from the group consisting of 30 g needles, 32 g needles, 34 g needles, and sub 34 g needles.

14. The system of claim 7, wherein the needle is configured to pierce entirely through the stopper member to be at least partially retracted into the plunger interior.

15. The system of claim 7, wherein the energy-storage member is intercoupled between an interior surface of the plunger member and the needle retention feature.

* * * * *